US008147817B2

(12) United States Patent
Lee

(10) Patent No.: US 8,147,817 B2
(45) Date of Patent: Apr. 3, 2012

(54) IL-33 IN THE TREATMENT AND DIAGNOSIS OF DISEASES AND DISORDERS

(75) Inventor: Richard T. Lee, Weston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 172 days.

(21) Appl. No.: 11/800,405

(22) Filed: May 4, 2007

(65) Prior Publication Data

US 2008/0003199 A1 Jan. 3, 2008

Related U.S. Application Data

(60) Provisional application No. 60/798,150, filed on May 4, 2006, provisional application No. 60/920,455, filed on Mar. 27, 2007.

(51) Int. Cl.
*A61K 38/20* (2006.01)
*A61K 45/00* (2006.01)
*A61P 9/00* (2006.01)
*C07K 14/435* (2006.01)

(52) U.S. Cl. ........ 424/85.2; 514/16.4; 530/351; 435/375
(58) Field of Classification Search ........................ None
See application file for complete search history.

(56) References Cited

U.S. PATENT DOCUMENTS

| 5,217,899 A | 6/1993 | Shapiro et al. |
| 5,348,879 A | 9/1994 | Shapiro et al. |
| 5,786,163 A | 7/1998 | Hall |
| 6,288,218 B1 | 9/2001 | Levinson |
| 6,323,333 B1 | 11/2001 | Tsui |
| 6,323,334 B1 | 11/2001 | Kingsbury et al. |
| 7,087,396 B2 | 8/2006 | Tominaga et al. |
| 7,432,060 B2 | 10/2008 | Lee |
| 7,655,415 B2 | 2/2010 | Lee |
| 7,670,769 B2 | 3/2010 | Lee |
| 2002/0072674 A1 | 6/2002 | Criton et al. |
| 2002/0115081 A1 | 8/2002 | Lee et al. |
| 2003/0124624 A1 | 7/2003 | Tominaga et al. |
| 2004/0048286 A1 | 3/2004 | Lee |
| 2005/0130136 A1 | 6/2005 | Lee |
| 2005/0203046 A1 | 9/2005 | Scmitz et al. |
| 2006/0216755 A1 | 9/2006 | Lee |
| 2007/0160579 A1 | 7/2007 | Schmitz et al. |
| 2009/0192078 A1 | 7/2009 | Lee |

FOREIGN PATENT DOCUMENTS

| JP | 6178687 | 6/1994 |
| JP | 7031479 | 2/1995 |
| WO | WO 98/07754 A1 | 2/1998 |
| WO | WO 98/38311 | 9/1998 |
| WO | WO 99/34217 A1 | 7/1999 |
| WO | WO 00/34477 A2 | 6/2000 |
| WO | WO 00/35473 A2 | 6/2000 |
| WO | WO 00/35951 A1 | 6/2000 |
| WO | WO 00/52022 A1 | 9/2000 |
| WO | WO 00/73498 A1 | 12/2000 |
| WO | WO 01/21641 A1 | 3/2001 |
| WO | WO 01/70817 A1 | 9/2001 |
| WO | WO 02/38794 A2 | 5/2002 |

OTHER PUBLICATIONS

Albert et al., Prospective study of C-reactive protein, homocysteine, and plasma lipid levels as predictors of sudden cardiac death. Circulation. Jun 4, 2002;105(22):2595-9.
Auer et al., C-reactive protein and coronary artery disease. Jpn Heart J. Nov. 2002;43(6):607-19.
Aukrust et al., Cytokine network in congestive heart failure secondary to ischemic or idiopathic dilated cardiomyopathy. Am J Cardiol. Feb. 1, 1999;83(3):376-82.
Baumgarten et al., Cytokines as emerging targets in the treatment of heart failure. Trends Cardiovasc Med. Jul. 2000;10(5):216-23.
Brown, Techniques for mechanical stimulation of cells in vitro: a review. J Biomech. Jan. 2000;33(1):3-14. Review.
Carter RW, et al. Regulation of ST2L expression on T helper (Th) type 2 cells. Eur J Immunol. Oct. 2000;31(10):2979-85 Abstract Only.
Chan WL, et al. Human IL-18 receptor and ST2L are stable and selective markers for the respective type 1 and type 2 circulating lymphocytes. J Immunol. Aug. 1, 2001;167(3):1238-44 Abstract Only.
Cheng et al., Mechanical strain tightly controls fibroblast growth factor-2 release from cultured human vascular smooth muscle cells. Circ Res. Jan. 1997;80(1):28-36.
Coyle et al., Crucial role of the interleukin 1 receptor family member T1/ST2 in T helper cell type 2-mediated lung mucosal immune responses. J Exp Med. Oct. 4, 1999;190(7):895-902.
Dinarello, An IL-1 family member requires Caspase-1 processing and signals through the ST2 receptor, Immunity, Nov. 2005; 23(5):461-2.
De Keulenaer et al., Identification of IEX-1 as a biomechanically controlled nuclear factor-kappaB target gene that inhibits cardiomyocyte hypertrophy. Circ Res. Apr. 5, 2002;90(6):690-6.
Feldman et al., C-reactive protein is an independent predictor of mortality in women with HIV-1 infection. J Acquir Immune Defic Syndr. Feb. 1, 2003;32(2):210-4. Abstract Only.
Feng et al., Transcriptional profile of mechanically induced genes in human vascular smooth muscle cells. Circ Res. Dec, 3-17, 1999;85(12):1118-23.
Forssmann et al., The heart is the center of a new endocrine, paracrine, and neuroendocrine system. Arch Histol Cytol. 1989;52 Suppl:293-315. Review. Abstract Only.
Gayle et al., Cloning of a putative ligand for the T1/ST2 receptor, JBC, Mar. 8, 1996; 271(10):5784-5789.

(Continued)

*Primary Examiner* — Bridget E Bunner
*Assistant Examiner* — Fozia Hamud
(74) *Attorney, Agent, or Firm* — Wolf, Greenfield & Sacks, P.C.

(57) ABSTRACT

This invention relates to methods and compositions for the treatment and diagnosis of cardiac diseases and disorders, such as cardiac hypertrophy, myocardial infarction, stroke, arteriosclerosis and heart failure. The invention also relates to methods and compositions for the treatment of fibrosis-related diseases as well as methods and compositions for reducing apoptosis, increasing ST2L signaling, decreasing NF-κB activation, decreasing IκBα phosphorylation, decreasing P38MAPK phosphorylation, decreasing JNK phosphorylation, decreasing reactive oxygen species generation, decreasing macrophage infiltration and/or decreasing the expression of hypertrophic genes. More specifically, the invention relates to IL-33 and/or soluble ST2 inhibiting agents for use in the methods and compositions provided.

7 Claims, 38 Drawing Sheets

OTHER PUBLICATIONS

GenBank Submission; NIH/NCBI; Accession No. AAA67172 (ROD May 23, 1995), Bergers et al.
GenBank Submission; NIH/NCBI; Accession No. AAX86998 (PRI Nov. 21, 2005), Schmitz et al.
GenBank Submission; NIH/NCBI; Accession No. AB012701 (PRI Aug. 12, 2005), LI et al.
GenBank Submission; NIH/NCBI; Accession No. AB022176 (PRI Sep. 15, 2007), Iwahana et al.
GenBank Submission; NIH/NCBI; Accession No. AB024518 (PRI Mar. 10, 1999), Onada et al.
GenBank Submission; NIH/NCBI; Accession No. AB029084 (PRI Oct. 31, 1999), Tominaga, S.
GenBank Submission; NIH/NCBI; Accession No. AC007248 (PRI Apr. 21, 2005), Waterston et al.
GenBank Submission; NIH/NCBI; Accession No. AL117622 (PRI Feb. 18, 2000), Duesterhoeft et al.
GenBank Submission; NIH/NCBI; Accession No. AY905581 (PRI Nov. 21, 2005), Schmitiz et al.
GenBank Submission; NIH/NCBI; Accession No. AY905582 (ROD Nov. 21, 2005), Schmitiz et al.
GenBank Submission; NIH/NCBI; Accession No. BC081993 (ROD Jul. 17, 2006), Strausberg et al.
GenBank Submission; NIH/NCBI; Accession No. D12763 (PRI Jan. 23, 2003), Tominaga, S.
GenBank Submission; NIH/NCBI; Accession No. D12764 (PRI May 29, 2002), Tominaga, S.
GenBank Submission; NIH/NCBI; Accession No. D13695 (ROD Feb. 3, 1999), Yanagisawa et al.
GenBank Submission; NIH/NCBI; Accession No. E07714 (PAT Nov. 4, 2005), Tominaga, S.
GenBank Submission; NIH/NCBI; Accession No. E07716 (PAT Nov. 4, 2005), Tominaga, S.
GenBank Submission; NIH/NCBI; Accession No. E08652 (PAT Nov. 4, 2005), Yanagisawa et al.
GenBank Submission; NIH/NCBI; Accession No. NM_003856 (PRI Nov. 18, 2007), Hayakawa et al.
GenBank Submission; NIH/NCBI; Accession No. NM_013037 (ROD Nov. 17, 2006), Kwitek et al.
GenBank Submission; NIH/NCBI; Accession No. NM_016232 (PRI Nov. 18, 2007), Hayakawa et al.
GenBank Submission; NIH/NCBI; Accession No. NP_003847(PRI Nov. 18, 2007), Hayakawa et al.
GenBank Submission; NIH/NCBI; Accession No. NP_057316 (PRI Nov. 18, 2007), Hayakawa et al.
GenBank Submission; NIH/NCBI; Accession No. U04317 (ROD May 27, 1994), Bergers et al.
GenBank Submission; NIH/NCBI; Accession No. U04319 (ROD May 24, 1995), Bergers et al.
GenBank Submission; NIH/NCBI; Accession No. X60184 (ROD Nov. 14, 2006), Tominaga et al.
GenBank Submission; NIH/NCBI; Accession No. Y07519 (ROD Apr. 18, 2005), Tominaga, S.
Gutstein et al., Role of inositol 1,4,5-trisphosphate receptors in regulating apoptotic signaling and heart failure. Heart Vessels. 1997;Suppl 12:53-7.
Gwechenberger et al., Cardiac myocytes produce interleukin-6 in culture and in viable border zone of reperfused infarctions. Circulation. Feb. 2, 1999;99(4):546-51.
Hanyu T, et al. Urinary Thrombomodulin in Patients with Rheumatoid Arthritis: Relationship to Disease Subset. 1999; 18:385-9.
Heeschen et al., Predictive value of C-reactive protein and troponin T in patients with unstable angina: a comparative analysis. CAPTURE Investigators. Chimeric c7E3 AntiPlatelet Therapy in Unstable angina REfractory to standard treatment trial. J Am Coll Cardiol. May 2000;35(6):1535-42. Abstract Only.
Hirota et al., Loss of a gp130 cardiac muscle cell survival pathway is a critical event in the onset of heart failure during biomechanical stress. Cell. Apr. 16, 1999;97(2):189-98.
Information Hyperlinked Over Proteins—Symbol IL1RL1, Q01638, Tominaga et a;l. 1992.
Iwahana et al., Different promoter usage and multiple transcription initiation sites of the interleukin-1 receptor-related human ST2 gene in UT-7 and TM12 cells. Eur J Biochem. Sep. 1999;264(2):397-406.
Izakov et al., Cooperative effects due to calcium binding by troponin and their consequences for contraction and relaxation of cardiac muscle under various conditions of mechanical loading. Circ Res. Nov. 1991;69(5):1171-84.
Januzzi et al., Utility of amino-terminal pro-brain natriuretic peptide testing for prediction of 1-year mortality in patients with dyspnea treated in the emergency department. Arch Intern Med. Feb. 13, 2006;166(3):315-20.
Joyce et al., Two inhibitors of pro-inflammatory cytokine release, interleukin-10 and interleukin-4, have contrasting effects on release of soluble p75 tumor necrosis factor receptor by cultured monocytes. Eur J Immunol. Nov. 1994;24(11):2699-705.
Kida et al., Pathophysiological role of natriuretic peptides. Rinsho Byori. Aug. 1989;37(8):875-82. Abstract Only.
Kumar et al., Expression of ST2, an interleukin-1 receptor homologue, is induced by proinflammatory stimuli. Biochem Biophys Res Commun. Jun. 27, 1997;235(3):474-8.
Kuroiwa et al, Construction of ELISA system to quantify human ST2 protein in sera of patients. Hybridoma. Apr. 2000;19(2):151-9.
Kuroiwa K, et al., Identification of Human ST2 Protein in the Sera of Patients with Autoimmune Diseases. Biochemical and Biophysical Research Communications 2001; 284:1104-8.
Laine et al., Effect of ryanodine on atrial natriuretic peptide secretion by contracting and quiescent rat atrium. Pflugers Arch. Feb. 1994;426(3-4):276-83.
Lammerding et al., Mechanotransduction in cardiac myocytes. Ann N Y Acad Sci. May 2004;1015:53-70.
Löhning et al., T1/ST2 is preferentially expressed on murine Th2 cells, independent of interleukin 4, interleukin 5, and interleukin 10, and important for Th2 effector function. Proc Natl Acad Sci U S A. Jun. 9, 1998;95(12):6930-5.
MacGowan et al., Circulating interleukin-6 in severe heart failure. Am J Cardiol. Apr. 15, 1997;79(8):1128-31.
MacKenna et al., Role of mechanical factors in modulating cardiac fibroblast function and extracellular matrix synthesis. Cardiovasc Res. May 2000;46(2):257-63.
Mann et al., Stress activated cytokines and the heart. Cytokine Growth Factor Rev. Dec. 1996;7(4):341-54.
Millenium Pharmaceuticals, Inc. Millenium Pharmaceuticals Identifies a Key mediator of Allergic Immune Response. Press Release Oct. 4, 1999, 2 pages.
Mitcham et al., T1/ST2 signaling establishes it as a member of an expanding interleukin-1 receptor family. J Biol Chem. Mar. 8, 1996;271(10):5777-83.
Monoclonal Antibody: Anti-Human ST2; Medical & Biological Laboratories Co., Ltd., Aug. 23, 2000 (2 pages).
Mukoyama et al, Augmented secretion of brain natriuretic peptide in acute myocardial infarction. Biochem Biophys Res Commun. Oct. 15, 1991;180(1):431-6. Abstract Only.
Murphy et al., Signaling and transcription in T helper development. Annu Rev Immunol. 2000;18:451-94.
Murray et al., Chronic beta-adrenergic stimulation induces myocardial proinflammatory cytokine expression. Circulation. May 23, 2000;101(20):2338-41.
Nakano M, et al. Elevation of Soluble Thrombomodulin Antigen Levels in the Serum and Urine of Streptozotocin-Induced Diabetes Model Rats. Thrombosis Research 2000; 99:83-91.
Nakano M, et al. Characterization of Soluble Thrombomodulin Fragments in Human Urine. Thromb. Haemost. 1998; 79(2):331-337.
NCBI BLASTN 2.0.14 [Jun. 29, 2000], BLAST Results, Query 2065 letters, (5 pages) printed Aug. 23, 2000, Altschul et al.
NCBI BLASTN 2.0.14 [Jun. 29, 2000], BLAST Results, 2586 letters, (5 pages) printed Aug. 23, 2000, Altschul et al.
NCBI BLASTN 2.0.14 [Jun. 29, 2000], BLAST Results, Query 2065 letters, (5 pages) printed Aug. 23, 2000.
NCBI BLASTN 2.0.14 [Jun. 29, 2000], BLAST Results, 2586 letters, (5 pages) printed Aug. 23, 2000, Altschul et al.
NCBI BLASTN 2.2.2 [Dec. 14, 2001], BLAST Results (21 pages), Altschul et al.
NCBI BLASTN 2.2.2 [Dec. 14, 2001], BLAST Results (15 pages), Altschul et al.

NG et al., Diagnosis of heart failure using urinary natriuretic peptides. Clin Sci (Lond). Feb. 2004;106(2):129-33.

Nichols et al., The influence of 'diastolic' length on the contractility of isolated cat papillary muscle. J Physiol. Apr. 1985;361:269-79.

O'Neill et al., the IL-1 receptor/toll-like receptor superfamily: crucial receptors for inflammation and host defense. Immunol Today. May 2000;21(5):206-9.

Ohki R et al. Identification of mechanically induced genes in human monocytic cells by DNA microarrays. J. Hypertens., Apr. 2002; 20(4):685-691 Abstract Only.

Ohtsuka et al., Effect of beta-blockers on circulating levels of inflammatory and anti-inflammatory cytokines in patients with dilated cardiomyopathy. J Am Coll Cardiol. Feb. 2001;37(2):412-7.

Onda H, et al. Identification of Genes Differentially Expressed in Canine Vasospastic Cerebral Arteries After Subarachnoid Hemorrhage. Journal of Cerebral Blood Flow & Metabolism 1999; 19:1279-1288.

Oshikawa, K, et al. Elevated Soluble ST2 Protein Levels in Sera of Patients with Asthma with an Acute Exacerbation. Am. J. Respir. Crit. Care Med. 2001; 164:277-81.

Papapetropoulos A, et al. Nitric oxide synthase inhibitors attenuate transforming-growth-factor-beta 1-stimulated capillary organization in vitro. Am J Pathol. May 1997;150(5):1835-44.

Potter et al., Mutations in the murine fitness 1 gene result in defective hematopoiesis. Blood. Sep. 1, 1997;90(5):1850-7.

Prabhu et al., Beta-adrenergic blockade in developing heart failure: effects on myocardial inflammatory cytokines, nitric oxide, and remodeling. Circulation. May 2, 2000;101(17):2103-9.

Pulkki et al., Cytokines and cardiomyocyte death. Ann Med. Aug. 1997;29(4):339-43.

Roig et al., Serum interleukin-6 in congestive heart failure secondary to idiopathic dilated cardiomyopathy. Am J Cardiol. Sep. 1, 1998;82(5):688-90, A8.

Sanada et al., IL-33/ST2 is a critical Cardioprotective Fibroblast-cardiomyocyte signaling system activatd by mechanical overload, 2006 Session AOP.37.4, presentation 1380, Abstract only.

Sanada et al., IL-33 and ST2 comprise a critical biomechanically induced and cardioprotective signaling system, J. Clin Invest, 2007; 117:1538-49. Available online May 10, 2007.

Saccani et al., Divergent effects of LPS on expression of IL-1 receptor family members in mononuclear phagocytes in vitro and in vivo. Cytokine. Oct. 1998;10(10):773-80.

Schaffer et al., Device for the application of a dynamic biaxially uniform and isotropic strain to a flexible cell culture membrane. J Orthop Res. Sep. 1994;12(5):709-19.

Schmitz et al., IL-33, an Interleukin-1-like Cytokine that signals via the IL-1 receptor-related protein ST2 and induces T helper type 2-associated cytokines, Immunity, Nov. 2005; 23(5):479-90.

Shimpo et al., Serum levels of the interleukin-1 receptor family member ST2 predict mortality and clinical outcome in acute myocardial infarction. Circulation. May 11, 2004;109(18):2186-90.

Sims JE, IL-1 and IL-18 Receptors, and Their Extended Family. Current Opinion in Immunology. 2002; 14:117-122.

Sussman et al., Dance band on the Titanic: biomechanical signaling in cardiac hypertrophy. Circ Res. Nov. 15, 2002;91(10):888-98.

Sutton et al., Left ventricular remodeling after myocardial infarction: pathophysiology and therapy. Circulation. Jun. 27, 2000;101(25):2981-8.

Tang Z, et al. Gene Expression profiling during the transition to failure in TNF-α over-expressing mice demonstrates the development of autoimmune myocarditis. Journal of Molecular and Cellular Cardiology 2004; 36:515-30.

Tominaga et al., The existence of a growth-specific DNA binding factor for the promoter region of mouse ST2 gene. FEBS Lett. Nov. 14, 1994;354(3):311-4.

Tominaga et al., A putative protein of a growth specific cDNA from BALB/c-3T3 cells is highly similar to the extracellular portion of mouse interleukin 1 receptor. FEBS Lett. Dec. 4, 1989;258(2):301-4.

Tominaga S et al. "Nucleotide sequence of a complementary DNA for human ST2" *Biochim Biophys Acta.* Dec. 29, 1992;1171(2):215-8 Abstract Only.

Townsend et al., T1/ST2-deficient mice demonstrate the importance of T1/ST2 in developing primary T helper cell type 2 responses. J Exp Med. Mar. 20, 2000;191(6):1069-76.

Trehu et al., Phase I trial of interleukin 2 in combination with the soluble tumor necrosis factor receptor p75 IgG chimera. Clin Cancer Res. Aug. 1996;2(8):1341-51.

Tsutamoto et al., Interleukin-6 spillover in the peripheral circulation increases with the severity of heart failure, and the high plasma level of interleukin-6 is an important prognostic predictor in patients with congestive heart failure. J Am Coll Cardiol. Feb. 1998;31(2):391-8.

Tung et al., Influence of stretch on excitation threshold of single frog ventricular cells. Exp Physiol. Mar. 1995;80(2):221-35.

Vahl et al., Length dependence of calcium- and force-transients in normal and failing human myocardium. J Mol Cell Cardiol. May 1998;30(5):957-66.

Van Kimmenade et al., Utility of amino-terminal pro-brain natriuretic peptide, galectin-3, and apelin for the evaluation of patients with acute heart failure. J Am Coll Cardiol. Sep. 19, 2006;48(6):1217-24.

Weinberg EO, et al. Expression and Regulation of ST2, an Interleukin-1 Receptor Family Member, in Cardiomyocytes and Myocardial Infarction Circulation 2002; 106:2961-6; published online Nov. 11, 2002.

Weinberg et al., Identification of serum soluble ST2 receptor as a novel heart failure biomarker. Circulation. Feb. 11, 2003;107(5):721-6. Online version published Jan. 13, 2003.

Yamamoto et al., Induction of tenascin-C in cardiac myocytes by mechanical deformation. Role of reactive oxygen species. J Biol Chem. Jul. 30, 1999;274(31):21840-6.

Yamamoto et al., Mechanical strain suppresses inducible nitric-oxide synthase in cardiac myocytes. J Biol Chem. May 8, 1998;273(19):11862-6.

Yamamoto et al., Regulation of cardiomyocyte mechanotransduction by the cardiac cycle. Circulation. Mar. 13, 2001;103(10):1459-64.

Yamaoka et al., Anti-inflammatory cytokine profile in human heart failure: behavior of interleukin-10 in association with tumor necrosis factor-alpha. Jpn Circ J. Dec. 1999;63(12):951-6.

Yanagisawa et al., Presence of a novel primary response gene ST2L, encoding a product highly similar to the interleukin 1 receptor type 1. FEBS Lett. Feb. 22, 1993;318(1):83-7.

Yanagisawa et al., The expression of ST2 gene in helper T cells and the binding of ST2 protein to myeloma-derived RPMI8226 cells. J Biochem (Tokyo). Jan. 1997;121(1):95-103.

Zebrack et al., Usefulness of high-sensitivity C-reactive protein in predicting long-term risk of death or acute myocardial infarction in patients with unstable or stable angina pectoris or acute myocardial infarction. Am J Cardiol. Jan. 15, 2002;89(2):145-9.

Vidal et al., Prognostic Value of Cytokines and Neurohormones in Severe Heart Failure, Rev Esp Cardiol 2002; 55(5):481-6.

Nozaki et al., Soluble Tumor Necrosis Factor Receptors are Elevated in Relation to Severity of Congestive Heart Failure, Jpn Circ J 1997; 61:657-64.

Orus et al., Prognostic Value of Serum Cytokines in Patients with Congestive Heart Failure, J Heart Lung Transplant 2000; 19:419-25.

Belch et al., Oxygen free radicals and congestive heart failure. Br Heart J. May 1991;65(5):245-8. Abstract Only.

Blum et al., Pathophysiological role of cytokines in congestive heart failure. Annu Rev Med. 2001;52:15-27. Abstract Only.

Galvani et al., Prognostic influence of elevated values of cardiac troponin I in patients with unstable angina. Circulation. Apr. 15, 1997;95(8):2053-9. Abstract Only.

Goldstein, Plasma norepinephrine as an indicator of sympathetic neural activity in clinical cardiology. Am J Cardiol. Dec. 1981;48(6):1147-54. Abstract Only.

Oshikawa et al., Expression of ST2 in helper T lymphocytes of malignant pleural effusions. Am J Respir Crit Care Med. Apr. 1, 2002;165(7):1005-9.

Selvais et al., Direct comparison between endothelin-1, N-terminal proatrial natriuretic factor, and brain natriuretic peptide as prognostic markers of survival in congestive heart failure. J Card Fail. Sep. 2000;6(3):201-7. Abstract Only.

[No Author Listed] Cardiac Tumors: Cardiovascular Disorders: Merck Manual Professional. May 2007; 4 pages. Available at http://www.merck.com/mmpe/sec07/ch083/ch083a.html. Last accessed. May 5, 2010, Jay Goodkind.

Dunne et al., The interleukin-1 receptor/Toll-like receptor superfamily: signal transduction during inflammation and host defense. Sci STKE. Feb. 25, 2003;2003(171):re3.

Frangogiannis et al., Resident cardiac mast cells degranulate and release preformed TNF-alpha, initiating the cytokine cascade in experimental canine myocardial ischemia/reperfusion. Circulation. Aug. 18, 1998;98(7):699-710.

Kumar et al., ST2/T1 protein functionally binds to two secreted proteins from Balb/c 3T3 and human umbilical vein endothelial cells but does not bind interleukin 1. J Biol Chem. Nov. 17, 1995;270(46):27905-13.

Ninomiya-Tsuji et al., The kinase TAK1 can activate the NIK-I kappaB as well as the MAP kinase cascade in the IL-1 signalling pathway. Nature. Mar. 18, 1999;398(6724):252-6.

Ørntoft et al., Genome-wide study of gene copy numbers, transcripts, and protein levels in pairs of non-invasive and invasive human transitional cell carcinomas. Mol Cell Proteomics. Jan. 2002;1(1):37-45.

Shioi et al., Increased expression of interleukin-1 beta and monocyte chemotactic and activating factor/monocyte chemoattractant protein-1 in the hypertrophied and failing heart with pressure overload. Circ Res. Nov. 1997;81(5):664-71.

US 8,147,817 B2

IL-33 IN THE TREATMENT AND DIAGNOSIS OF DISEASES AND DISORDERS

RELATED APPLICATIONS

This application claims the benefit under 35 U.S.C. §119 of U.S. provisional application 60/798,150, filed May 4, 2006 and U.S. provisional application 60/920,455, filed Mar. 27, 2007, the contents of each of which are incorporated herein by reference in their entirety.

FIELD OF THE INVENTION

This invention relates to methods and compositions for the treatment and diagnosis of cardiac diseases and disorders, such as cardiac hypertrophy, myocardial infarction, stroke, arteriosclerosis and heart failure. The invention also relates to methods and compositions for the treatment of fibrosis-related diseases as well as other methods and compositions.

BACKGROUND OF THE INVENTION

Despite significant advances in diagnosis and therapy, cardiovascular events remain a major common cause of morbidity and mortality. Thus, prevention of cardiovascular events such as myocardial infarction and stroke is an area of major public health importance.

Screening tests for several risk factors for future cardiovascular events have been described and are in clinical use in the detection of human subjects at high risk. Such screening tests include, for example, cholesterol, low density lipoprotein cholesterol (LDLC), and, more recently, C-reactive protein (CRP) screening tests. In addition, human subjects with risk factors for cardiovascular event(s) are prescribed therapies to reduce the risk of a future cardiovascular event. For example, human subjects with abnormally high cholesterol and/or LDLC levels are frequently prescribed a class of drugs called statins to reduce cholesterol levels to reduce the risk of a future cardiovascular event.

The beneficial effects, however, of such agents in human subjects vary in magnitude among different human subjects. Additionally, a large number of cardiovascular disorders occur in subjects with apparently low to moderate risk profiles, and the ability to identify such patients is limited. At this time only a few tests are available to determine whether certain therapies with cardiovascular agents are effective or are expected to be more or less beneficial in reducing future cardiovascular event(s). Thus, there is a need for improved tests and approaches to therapy in human subjects.

SUMMARY OF THE INVENTION

It has been found that IL-33 signaling through membrane-bound ST2 has beneficial effects. The modulation of this signaling pathway can be used, for example, for the treatment of cardiac diseases and disorders as well as fibrosis-related diseases. In addition, IL-33 has been found to be induced by cardiac strain and can be used in various methods of evaluating risk of developing a disease or disorder, diagnosis, determining the prognosis (i.e., predicting the outcome; determining the onset, regression or progression) of a disease or disorder, or evaluating therapeutic efficacy.

In one aspect of the invention, a method for treating a subject having or at risk of developing a cardiac disease or disorder is provided. In one embodiment, the method includes the step of administering an effective amount of IL-33 to a subject in need of such a treatment to treat the subject. In another embodiment, the level of IL-33 in the subject is raised above a predetermined value.

In another aspect of the invention, a method for treating a subject having or at risk of developing a cardiac disease or disorder is provided, wherein the method includes the steps of selecting a subject on the basis that the subject aberrantly expresses IL-33, and administering IL-33 to the subject and/or a second agent in an effective amount to treat the subject. In one embodiment, the level of IL-33 in the subject is raised above a predetermined value.

In still another embodiment, the methods include the step of administering a second agent for treating the cardiac disease or disorder. In one embodiment, the second agent is a soluble ST2 inhibiting agent, an anti-lipemic agent, an anti-inflammatory agent, an anti-thrombotic agent, a fibrinolytic agent, an anti-platelet agent, a direct thrombin inhibitor, a glycoprotein IIb/IIIa receptor inhibitor, an alpha-adrenergic blocker, a beta-adrenergic blocker, a cyclooxygenase-2 inhibitor, an angiotensin system inhibitor, an anti-arrhythmic, a calcium channel blocker, a diuretic, an inotropic agent, a vasodilator, a vasopressor, a thiazolidinedione, a cannabinoid-1 receptor blocker or a combination thereof.

In one embodiment, the cardiac disease or disorder is myocardial infarction, stroke, arteriosclerosis or heart failure. In another embodiment, the cardiac disease or disorder is cardiac hypertrophy.

In a further embodiment, the IL-33 is administered orally, sublingually, intravenously, intramuscularly or subcutaneously. In yet another embodiment, the IL-33 is administered prophylactically. In another embodiment, the IL-33 is administered by injection or infusion.

In yet another embodiment, the subject is otherwise free of indications calling for treatment with IL-33. In a further embodiment, the subject is free of indications calling for treatment with IL-33 other than a cardiac disease or disorder. In a further embodiment, the subject is apparently healthy.

In still another embodiment, the subject has a cardiovascular condition. In one embodiment the cardiac disease or disorder is myocardial infaction, stroke, arteriosclerosis or heart failure. In a further embodiment, the cardiac disease or disorder is myocardial infaction. In another embodiment, the subject is given IL-33 as soon as the subject has been diagnosed as or is suspected of having the cardiac disease or disorder. In a further embodiment, the subject is given IL-33 as soon as the subject has been diagnosed or is suspected as having had the cardiac disease or disorder. In one embodiment, IL-33 can be administered immediately, within 15, 20, 30, 40 or 50 minutes, within 1, 2, 3, 4, 5, 6, 7, 8, 9, 10, 12, 15, 18, 20 or 22 hours, within 1, 2, 3 or 4 days or within a week of the diagnosis or suspicion of the cardiac disease or disorder. In another embodiment, IL-33 is administered to the subject upon diagnosis or admittance to a hospital. In still another embodiment, IL-33 is administered to the subject by a paramedic or emergency care provider. In still another embodiment, IL-33 can be administered for a few days, one week or a few weeks (e.g., 1, 2, 3 or 4 weeks) beginning at or shortly after the time of diagnosis or suspicion of the cardiac disease or disorder.

In still another aspect of the invention, a method for treating a subject having or at risk of developing a cardiac disease or disorder that includes the step of administering an effective amount of a soluble ST2 inhibiting agent to a subject in need of such a treatment to treat the subject, wherein the soluble ST2 inhibiting agent increases the amount of IL-33 signaling via membrane-bound ST2 in the subject, is provided. In one embodiment, the level of soluble ST2 in the subject is brought below a predetermined value. In another embodiment, the IL-33 signaling is signaling due to endogenous IL-33. In yet another embodiment, the IL-33 signaling is signaling due to exogenous IL-33 or exogenous IL-33 in combination with endogenous IL-33. The method, in one embodiment, therefore also includes the step of administering IL-33 to the subject. The IL-33 can be administered prior to, concomitantly with or subsequent to the administration of the soluble ST2 inhibiting agent.

In a further aspect of the invention, a method for treating a subject having or at risk of developing a cardiac disease or disorder that includes the steps of selecting a subject on the basis that the subject aberrantly expresses soluble ST2, and administering a soluble ST2 inhibiting agent to the subject and/or a second agent in an effective amount to treat the subject is provided. In one embodiment, the level of soluble ST2 in the subject is brought below a predetermined value.

In one embodiment of the methods, the soluble ST2 inhibiting agent is an antibody that specifically binds soluble ST2. In another embodiment, the soluble ST2 inhibiting agent is a nucleic acid molecule that specifically binds a nucleic acid molecule that encodes soluble ST2. In one embodiment, the nucleic acid molecule that specifically binds is a siRNA molecule.

In another embodiment, the methods also include the step of administering a second agent for treating the cardiac disease or disorder. In one embodiment, the second agent is IL-33, an anti-lipemic agent, an anti-inflammatory agent, an anti-thrombotic agent, a fibrinolytic agent, an anti-platelet agent, a direct thrombin inhibitor, a glycoprotein IIb/IIIa receptor inhibitor, an alpha-adrenergic blocker, a beta-adrenergic blocker, a cyclooxygenase-2 inhibitor, an angiotensin system inhibitor, an anti-arrhythmic, a calcium channel blocker, a diuretic, an inotropic agent, a vasodilator, a vasopressor, a thiazolidinedione, a cannabinoid-1 receptor blocker or a combination thereof.

In another embodiment, the cardiac disease or disorder is myocardial infarction, stroke, arteriosclerosis or heart failure. In a further embodiment, the cardiac disease or disorder is cardiac hypertrophy.

In a further embodiment, the IL-33 is administered orally, sublingually, intravenously, intramuscularly or subcutaneously. In one embodiment, the soluble ST2 inhibiting agent is administered prophylactically. In another embodiment, the soluble ST2 inhibiting agent is administered by injection or infusion.

In one embodiment, the subject is otherwise free of indications calling for treatment with the soluble ST2 inhibiting agent. In a further embodiment, the subject is free of indications calling for treatment with the soluble ST2 inhibiting agent other than a cardiac disease or disorder. In another embodiment, the subject is apparently healthy.

In still another embodiment, the subject has a cardiovascular condition. In one embodiment the cardiac disease or disorder is myocardial infaction, stroke, arteriosclerosis or heart failure. In a further embodiment, the cardiac disease or disorder is myocardial infaction. In another embodiment, the subject is given a soluble ST2 inhibiting agent as soon as the subject has been diagnosed as or is suspected of having the cardiac disease or disorder. In a further embodiment, the subject is given a soluble ST2 inhibiting agent as soon as the subject has been diagnosed as or is suspected of having had the cardiac disease or disorder. In one embodiment, a soluble ST2 inhibiting agent can be administered immediately, within 15, 20, 30, 40 or 50 minutes, within 1, 2, 3, 4, 5, 6, 7, 8, 9, 10, 12, 15, 18, 20 or 22 hours, within 1, 2, 3 or 4 days or within a week of the diagnosis or suspicion of the cardiac disease or disorder. In another embodiment, the soluble ST2 inhibiting agent is administered to the subject upon diagnosis or admittance to a hospital. In still another embodiment, the soluble ST2 inhibiting agent is administered to the subject by a paramedic or emergency care provider. In still another embodiment, the soluble ST2 inhibiting agent can be administered for a few days, one week or a few weeks (e.g., 1, 2, 3 or 4 weeks) beginning at or shortly after the time of diagnosis or suspicion of the cardiac disease or disorder.

In yet another aspect of the invention, a method for reducing apoptosis is provided. In one embodiment, the method includes the step of contacting one or more cardiac cells with IL-33 and/or a soluble ST2 inhibiting agent, wherein the IL-33 and/or the soluble ST2 inhibiting agent is in an amount effective to reduce apoptosis. In one embodiment, the soluble ST2 inhibiting agent is an antibody that specifically binds soluble ST2. In another embodiment, the soluble ST2 inhibiting agent is a nucleic acid molecule that specifically binds a nucleic acid molecule that encodes soluble ST2. In one embodiment, the nucleic acid molecule that specifically binds is a siRNA molecule.

In a further embodiment, the one or more cardiac cells are one or more cardiomyocytes.

In another embodiment, the contacting is carried out by administering IL-33 and/or the soluble ST2 inhibiting agent to a subject. In still another embodiment, the contacting is carried out in vitro.

In another aspect of the invention, a method for reducing fibrosis is provided. In one embodiment, the method includes the step of contacting one or more cells associated with fibrosis with IL-33 and/or a soluble ST2 inhibiting agent, wherein the IL-33 and/or the soluble ST2 inhibiting agent is in an amount effective to reduce fibrosis. In another embodiment, the soluble ST2 inhibiting agent is an antibody that specifically binds soluble ST2. In still another embodiment, the soluble ST2 inhibiting agent is a nucleic acid that specifically binds a nucleic acid molecule that encodes soluble ST2. In one embodiment, the nucleic acid molecule that specifically binds is a siRNA molecule.

In another embodiment, the fibrosis is fibrosis induced by adrenergic receptor and/or angiotensin receptor signaling, such as with an adrenergic receptor agonist or an angiotensin receptor agonist. In one embodiment, the adrenergic receptor agonist is phenylephrine. In another embodiment, the angiotensin receptor agonist is angiotensin II. In yet another embodiment, the fibrosis is associated with tissue injury. In one embodiment, the tissue injury is associated with cardiac strain or cardiac overload. In still another embodiment, the fibrosis is associated with a fibrosis-related disease. In one embodiment, the fibrosis-related disease is skin pathologic scarring, cirrhosis, cardiac fibrosis, liver fibrosis, kidney fibrosis, pulmonary fibrosis, bone marrow fibrosis, rheumatic heart disease, sclerosing peritonitis, glomerulosclerosis or scleroderma.

In a further embodiment, the one or more cells are one or more cardiac cells. In one embodiment, the one or more cardiac cells are one or more cardiac fibroblasts.

In another embodiment, the contacting is carried out by administering IL-33 and/or the soluble ST2 inhibiting agent to a subject. In one embodiment, the subject is also administered an anti-inflammatory or immunosuppressive agent or both. In a further embodiment, the subject is also administered IL-33. In still another embodiment, the contacting is carried out in vitro.

In still another aspect of the invention, methods are also provided whereby signaling through ST2L is increased. In one embodiment, the method includes the step of contacting one or more cardiac cells that are or have been exposed to hypertrophic stimuli with IL-33 and/or a soluble ST2 inhibiting agent, wherein the IL-33 and/or the soluble ST2 inhibiting agent is in an amount effective to increase ST2L signaling. In another embodiment, the soluble ST2 inhibiting agent is an antibody that specifically binds soluble ST2. In still another embodiment, the soluble ST2 inhibiting agent is a nucleic acid that specifically binds a nucleic acid molecule that encodes soluble ST2. In one embodiment, the nucleic acid molecule that specifically binds is a siRNA molecule.

In a further embodiment, the one or more cells are one or more cardiac cells. In one embodiment, the one or more cardiac cells are one or more cardiac myocytes. In another embodiment, the one or more cardiac cells are one or more cardiac fibroblasts.

In another embodiment, the contacting is carried out by administering IL-33 and/or the soluble ST2 inhibiting agent to a subject. In still another embodiment, the contacting is carried out in vitro.

In yet another aspect of the invention, methods are also provided whereby NF-κB activation is decreased. In one embodiment, the method includes the step of contacting one or more cardiac cells that are or have been exposed to hypertrophic stimuli with IL-33 and/or a soluble ST2 inhibiting agent, wherein the IL-33 and/or the soluble ST2 inhibiting agent is in an amount effective to decrease NF-κB activation. In another embodiment, the soluble ST2 inhibiting agent is an antibody that specifically binds soluble ST2. In still another embodiment, the soluble ST2 inhibiting agent is a nucleic acid that specifically binds a nucleic acid molecule that encodes soluble ST2. In one embodiment, the nucleic acid molecule that specifically binds is a siRNA molecule.

In a further embodiment, the one or more cells are one or more cardiac cells. In one embodiment, the one or more cardiac cells are one or more cardiac myocytes. In another embodiment, the one or more cardiac cells are one or more cardiac fibroblasts.

In another embodiment, the contacting is carried out by administering IL-33 and/or the soluble ST2 inhibiting agent to a subject. In still another embodiment, the contacting is carried out in vitro.

In still another aspect of the invention, methods are provided whereby IκBα phosphorylation, P38MAPK phosphorylation and/or JNK phosphorylation is decreased. In one embodiment, the method includes the step of contacting one or more cardiac cells that are or have been exposed to hypertrophic stimuli with IL-33 and/or a soluble ST2 inhibiting agent, wherein the IL-33 and/or the soluble ST2 inhibiting agent is in an amount effective to decrease IκBα phosphorylation, P38MAPK phosphorylation and/or JNK phosphorylation. In another embodiment, the soluble ST2 inhibiting agent is an antibody that specifically binds soluble ST2. In still another embodiment, the soluble ST2 inhibiting agent is a nucleic acid that specifically binds a nucleic acid molecule that encodes soluble ST2. In one embodiment, the nucleic acid molecule that specifically binds is a siRNA molecule.

In a further embodiment, the one or more cells are one or more cardiac cells. In one embodiment, the one or more cardiac cells are one or more cardiac myocytes. In another embodiment, the one or more cardiac cells are one or more cardiac fibroblasts.

In another embodiment, the contacting is carried out by administering IL-33 and/or the soluble ST2 inhibiting agent to a subject. In still another embodiment, the contacting is carried out in vitro.

In yet a further aspect of the invention, methods are provided whereby reactive oxygen species generation is decreased. In one embodiment, the method includes the step of contacting one or more cardiac cells that are or have been exposed to hypertrophic stimuli with IL-33 and/or a soluble ST2 inhibiting agent, wherein the IL-33 and/or the soluble ST2 inhibiting agent is in an amount effective to decrease reactive oxygen species generation. In another embodiment, the soluble ST2 inhibiting agent is an antibody that specifically binds soluble ST2. In still another embodiment, the soluble ST2 inhibiting agent is a nucleic acid that specifically binds a nucleic acid molecule that encodes soluble ST2. In one embodiment, the nucleic acid molecule that specifically binds is a siRNA molecule.

In a further embodiment, the one or more cells are one or more cardiac cells. In one embodiment, the one or more cardiac cells are one or more cardiac myocytes. In another embodiment, the one or more cardiac cells are one or more cardiac fibroblasts.

In another embodiment, the contacting is carried out by administering IL-33 and/or the soluble ST2 inhibiting agent to a subject. In still another embodiment, the contacting is carried out in vitro.

In yet another aspect of the invention, methods are provided whereby macrophage infiltration is decreased. In one embodiment, the method includes the step of contacting one or more cardiac cells that are or have been exposed to hypertrophic stimuli with IL-33 and/or a soluble ST2 inhibiting agent, wherein the IL-33 and/or the soluble ST2 inhibiting agent is in an amount effective to decrease macrophage infiltration. In another embodiment, the soluble ST2 inhibiting agent is an antibody that specifically binds soluble ST2. In still another embodiment, the soluble ST2 inhibiting agent is a nucleic acid that specifically binds a nucleic acid molecule that encodes soluble ST2. In one embodiment, the nucleic acid molecule that specifically binds is a siRNA molecule.

In a further embodiment, the one or more cells are one or more cardiac cells. In one embodiment, the one or more cardiac cells are one or more cardiac myocytes. In another embodiment, the one or more cardiac cells are one or more cardiac fibroblasts.

In another embodiment, the contacting is carried out by administering IL-33 and/or the soluble ST2 inhibiting agent to a subject. In still another embodiment, the contacting is carried out in vitro.

In still another aspect of the invention, methods are provided whereby the expression of hypertrophic genes is decreased. In one embodiment, the method includes the step of contacting one or more cardiac cells that are or have been exposed to hypertrophic stimuli with IL-33 and/or a soluble ST2 inhibiting agent, wherein the IL-33 and/or the soluble ST2 inhibiting agent is in an amount effective to decrease the expression of hypertrophic genes. In another embodiment, the hypertrophic gene is BNP or ANP. In another embodiment, the soluble ST2 inhibiting agent is an antibody that specifically binds soluble ST2. In still another embodiment, the soluble ST2 inhibiting agent is a nucleic acid that specifically binds a nucleic acid molecule that encodes soluble ST2. In one embodiment, the nucleic acid molecule that specifically binds is a siRNA molecule.

In a further embodiment, the one or more cells are one or more cardiac cells. In one embodiment, the one or more cardiac cells are one or more cardiac myocytes. In another embodiment, the one or more cardiac cells are one or more cardiac fibroblasts.

In another embodiment, the contacting is carried out by administering IL-33 and/or the soluble ST2 inhibiting agent to a subject. In still another embodiment, the contacting is carried out in vitro.

In a further embodiment, the contacting of IL-33 and/or the soluble ST2 inhibiting agent of any of the methods provided herein can be to one or more cardiac cells that are undergoing or have undergone hypertrophy rather than or in addition to the one or more cardiac cells that are or have been exposed to hypertrophic stimuli.

Also provided are compositions for use in the methods provided herein. In one aspect of the invention compositions of IL-33 are provided. In one embodiment, the composition comprises IL-33 and a second agent for treating a cardiac disease or disorder. In one embodiment, the second agent is a soluble ST2 inhibiting agent, an anti-lipemic agent, an anti-inflammatory agent, an anti-thrombotic agent, a fibrinolytic agent, an anti-platelet agent, a direct thrombin inhibitor, a glycoprotein IIb/IIIa receptor inhibitor, an alpha-adrenergic blocker, a beta-adrenergic blocker, a cyclooxygenase-2 inhibitor, an angiotensin system inhibitor, an anti-arrhythmic, a calcium channel blocker, a diuretic, an inotropic agent, a vasodilator, a vasopressor, a thiazolidinedione, a cannabinoid-1 receptor blocker or a combination thereof. In another embodiment, the composition also comprises a pharmaceutically acceptable carrier.

In another aspect of the invention, a composition is provided, which includes IL-33 and a second agent for treating a fibrosis-related disease. In one embodiment, the second agent is an anti-inflammatory agent or an immunosuppressive agent. In another embodiment, the second agent is a soluble ST2 inhibiting agent. In yet another embodiment, the composition also comprises a pharmaceutically acceptable carrier.

In yet another aspect of the invention compositions comprising a soluble ST2 inhibiting agent are provided. In one embodiment, the composition also comprises a pharmaceutically acceptable carrier. In another embodiment, the soluble ST2 inhibiting agent is an antibody that specifically binds soluble ST2. In another embodiment, the soluble ST2 inhibiting agent is a nucleic acid molecule that specifically binds a nucleic acid molecule that encodes soluble ST2. In a further embodiment, the nucleic acid molecule that specifically binds is a siRNA molecule.

In yet another embodiment, the composition also comprises a second agent for treating a cardiac disease or disorder. In one embodiment, the second agent is IL-33, an anti-lipemic agent, an anti-inflammatory agent, an anti-thrombotic agent, a fibrinolytic agent, an anti-platelet agent, a direct thrombin inhibitor, a glycoprotein IIb/IIIa receptor inhibitor, an alpha-adrenergic blocker, a beta-adrenergic blocker, a cyclooxygenase-2 inhibitor, an angiotensin system inhibitor, an anti-arrhythmic, a calcium channel blocker, a diuretic, an inotropic agent, a vasodilator, a vasopressor, a thiazolidinedione, a cannabinoid-1 receptor blocker or a combination thereof. In a further embodiment, the composition also comprises a second agent for treating a fibrosis-related disease. In one embodiment, the second agent is an anti-inflammatory agent or an immunosuppressive agent. In another embodiment, the second agent is IL-33.

Methods of evaluating risk, diagnosis, determining the progression of a cardiac disease or disorder or evaluating therapeutic efficacy are also provided.

In one aspect of the invention, a method for characterizing a subject's risk profile of developing a cardiac disease or disorder is provided. In one embodiment, the method includes the steps of determining the level of IL-33 in a subject (e.g., in a sample obtained from the subject), comparing the level of IL-33 to a predetermined value, and characterizing the subject's risk of developing the cardiac disease or disorder based upon the level of IL-33 in comparison to the predetermined value. In one embodiment, a level of IL-33 at or above the predetermined value is indicative that the subject is at an elevated risk of developing the cardiac disease or disorder. In another embodiment, a level of IL-33 below the predetermined value is indicative that the subject is not at an elevated risk of developing the cardiac disease or disorder. In a further embodiment, one or more of the steps of the method are repeated so as to characterize the subject's risk profile over time.

In still a further embodiment, the method also includes the step of performing one or more additional tests to evaluate the risk of cardiac disease or disorder. In one embodiment, the one or more additional tests is measuring a level of another marker of cardiac disease or disorder in the subject. In another embodiment, the other marker of cardiac disease or disorder is cholesterol, low density lipoprotein cholesterol (LDLC), soluble ST2 or a marker of systemic inflammation. In yet another embodiment, the marker of systemic inflammation is C-reactive protein (CRP), a cytokine or a cellular adhesion molecule. In a further embodiment, the cytokine is any one of human interleukins 1-17. In still a further embodiment, the cellular adhesion molecule is an integrin, a soluble intercellular adhesion molecule (sICAM-1), ICAM-3, BL-CAM, LFA-2, VCAM-1, NCAM, PECAM, fibrinogen, serum amyloid A (SAA), lipoprotein associated phospholipase A2 (Lp-PlA2), sCD40 ligand, myeloperoxidase, interleukin-6 (IL-6) or interleukin-8 (IL-8). In one embodiment, a level of soluble ST2 below a predetermined value is indicative that the subject is not at an elevated risk of developing the cardiac disease or disorder.

In another embodiment, the cardiac disease or disorder is myocardial infarction, stroke, arteriosclerosis or heart failure. In yet another embodiment, the cardiac disease or disorder is cardiac hypertrophy.

The sample can be, in one embodiment, a body fluid sample. In one embodiment, the body fluid sample is a blood, plasma, serum or a urine sample. In another embodiment, the sample is a body tissue sample. In one embodiment, the body tissue sample is a cardiac tissue sample.

In one embodiment, the subject is an apparently healthy subject.

In another aspect of the invention, a method for diagnosing a cardiac disease or disorder is provided. In one embodiment, the method includes the step of determining the level of IL-33 in a subject (e.g., in a sample obtained from the subject), comparing the level of IL-33 to a predetermined value, and diagnosing the cardiac disease or disorder based upon the comparison. In another embodiment, a level of IL-33 at or above the predetermined value is indicative that the subject has the cardiac disease or disorder. In another embodiment, a level of IL-33 below the predetermined value is indicative that the subject does not have the cardiac disease or disorder. In a further embodiment, the level of IL-33 is indicative that one or more additional tests is needed to reach a diagnosis.

In still another embodiment, therefore, the method includes the step of performing one or more additional tests to diagnose the cardiac disease or disorder. In one embodiment, the one or more additional tests is measuring a level of another marker of cardiac disease or disorder in the subject. In another embodiment, the other marker of cardiac disease or disorder is cholesterol, low density lipoprotein cholesterol (LDLC), soluble ST2 or a marker of systemic inflammation. In yet another embodiment, the marker of systemic inflammation is C-reactive protein (CRP), a cytokine or a cellular adhesion molecule. In another embodiment, the cytokine is any one of human interleukins 1-17. In a further embodiment, the cellular adhesion molecule is an integrin, a soluble intercellular adhesion molecule (sICAM-1), ICAM-3, BL-CAM, LFA-2, VCAM-1, NCAM, PECAM, fibrinogen, serum amyloid A (SAA), lipoprotein associated phospholipase A2 (LpPlA2), sCD40 ligand, myeloperoxidase, interleukin-6 (IL-6) or interleukin-8 (IL-8). In another embodiment, a level of soluble ST2 below a predetermined value is indicative that the subject does not have the cardiac disease or disorder.

In one embodiment, the cardiac disease or disorder is myocardial infarction, stroke, arteriosclerosis or heart failure. In another embodiment, the cardiac disease or disorder is cardiac hypertrophy.

In yet another embodiment, the sample is a body fluid sample. In one embodiment, the body fluid sample is a blood, plasma, serum or a urine sample. In a further embodiment, the sample is a body tissue sample. In still a further embodiment, the body tissue sample is a cardiac tissue sample.

In one embodiment, the subject is an apparently healthy subject.

In yet another aspect of the invention, a method for determining the prognosis of a cardiac disease or disorder is provided. In one embodiment, the method includes the steps of determining the level of IL-33 in a subject (e.g., in a sample obtained from the subject), and comparing the level of IL-33 to a predetermined value, wherein a level of IL-33 at or above the predetermined value is indicative of the prognosis of the cardiac disease or disorder in the subject. In another embodiment, the prognosis is that a positive outcome is expected. In a further embodiment, one or more of the steps are repeated so as to monitor the subject's prognosis over time.

In still another embodiment, the method includes the step of performing one or more additional tests to determine the prognosis of the cardiac disease or disorder in the subject. In one embodiment, the one or more additional tests is measuring a level of another marker of cardiac disease or disorder in the subject. In another embodiment, the other marker of cardiac disease or disorder is cholesterol, low density lipoprotein cholesterol (LDLC), soluble ST2 or a marker of systemic inflammation. In yet another embodiment, the marker of systemic inflammation is C-reactive protein (CRP), a cytokine or a cellular adhesion molecule. In another embodiment, the cytokine is any one of human interleukins 1-17. In a further embodiment, the cellular adhesion molecule is an integrin, a soluble intercellular adhesion molecule (sICAM-1), ICAM-3, BL-CAM, LFA-2, VCAM-1, NCAM, PECAM, fibrinogen, serum amyloid A (SAA), lipoprotein associated phospholipase A2 (LpPlA2), sCD40 ligand, myeloperoxidase, interleukin-6 (IL-6) or interleukin-8 (IL-8). In another embodiment, a level of soluble ST2 below a predetermined value is indicative of a positive prognosis of the cardiac disease or disorder in the subject.

In one embodiment, the cardiac disease or disorder is myocardial infarction, stroke, arteriosclerosis or heart failure. In another embodiment, the cardiac disease or disorder is cardiac hypertrophy.

In another embodiment, the sample is a body fluid sample. In one embodiment, the body fluid sample is a blood, plasma, serum or a urine sample. In a further embodiment, the sample is a body tissue sample. In yet a further embodiment, the body tissue sample is a cardiac tissue sample.

In a further aspect of the invention, a method for evaluating the efficacy of a therapy for treating or reducing the risk of a cardiac disease or disorder in a subject is provided. The method in one embodiment includes the step of determining the level of IL-33 in a subject (e.g., in a sample obtained from the subject) undergoing therapy with an agent to treat or reduce the risk of the cardiac disease or disorder, comparing the level of IL-33 that is determined to a predetermined value, and determining whether the level of IL-33 is at, below or above the predetermined value, said determination being indicative of whether the therapy is efficacious. In a further embodiment, a level of IL-33 that is at or above a predetermined value is indicative that the treatment is efficacious. In another embodiment, one or more of the steps are repeated so as to monitor the subject's levels of IL-33 over time and to monitor the efficacy of therapy over time.

In still another embodiment, therefore, the method includes the step of performing one or more additional tests to evaluate the efficacy of the therapy. In one embodiment, the one or more additional tests is measuring a level of another marker of cardiac disease or disorder in the subject. In another embodiment, the other marker of cardiac disease or disorder is cholesterol, low density lipoprotein cholesterol (LDLC), soluble ST2 or a marker of systemic inflammation. In yet another embodiment, the marker of systemic inflammation is C-reactive protein (CRP), a cytokine or a cellular adhesion molecule. In another embodiment, the cytokine is any one of human interleukins 1-17. In a further embodiment, the cellular adhesion molecule is an integrin, a soluble intercellular adhesion molecule (sICAM-1), ICAM-3, BL-CAM, LFA-2, VCAM-1, NCAM, PECAM, fibrinogen, serum amyloid A (SAA), lipoprotein associated phospholipase A2 (LpPlA2), sCD40 ligand, myeloperoxidase, interleukin-6 (IL-6) or interleukin-8 (IL-8). In one embodiment, determining whether the level of soluble ST2 is at, below or above a predetermined value is indicative of whether the therapy is efficacious. In another embodiment, a level of soluble ST2 that is at or below a predetermined value is indicative that the treatment is efficacious.

In one embodiment, the agent is IL-33, a soluble ST2 inhibiting agent, an anti-lipemic agent, an anti-inflammatory agent, an anti-thrombotic agent, a fibrinolytic agent, an anti-platelet agent, a direct thrombin inhibitor, a glycoprotein IIb/IIIa receptor inhibitor, an alpha-adrenergic blocker, a beta-adrenergic blocker, a cyclooxygenase-2 inhibitor, an angiotensin system inhibitor, an anti-arrhythmic, a calcium channel blocker, a diuretic, an inotropic agent, a vasodilator, a vasopressor, a thiazolidinedione, a cannabinoid-1 receptor blocker or a combination thereof.

In another aspect of the invention, a method for deciding on the course of a therapy in a subject is provided. In one embodiment, the method includes the step of determining the level of IL-33 in a subject (e.g., in a sample obtained from the subject) undergoing or about to undergo a therapy to treat or reduce the risk of a cardiac disease or disorder, comparing the level of IL-33 that is determined to a predetermined value, determining whether the level of IL-33 obtained is at, below or above the predetermined value, and deciding on the course of the therapy based on such determination. In another embodiment, one or more of the steps of the method are repeated so as to monitor the subject's level of IL-33 over time.

In still another embodiment, the method includes the step of performing one or more additional tests to decide on the course of therapy. In one embodiment, the one or more additional tests is measuring a level of another marker of cardiac disease or disorder in the subject. In another embodiment, the other marker of cardiac disease or disorder is cholesterol, low density lipoprotein cholesterol (LDLC), soluble ST2 or a marker of systemic inflammation. In yet another embodiment, the marker of systemic inflammation is C-reactive protein (CRP), a cytokine or a cellular adhesion molecule. In another embodiment, the cytokine is any one of human interleukins 1-17. In a further embodiment, the cellular adhesion molecule is an integrin, a soluble intercellular adhesion molecule (sICAM-1), ICAM-3, BL-CAM, LFA-2, VCAM-1, NCAM, PECAM, fibrinogen, serum amyloid A (SAA), lipoprotein associated phospholipase A2 (LpPlA2), sCD40 ligand, myeloperoxidase, interleukin-6 (IL-6) or interleukin-8 (IL-8). In one embodiment, determining whether the level of soluble ST2 is at, below or above a predetermined value is useful in deciding on the course of therapy.

In a further aspect of the invention, a method for identifying a candidate agent useful in the treatment of a cardiac disease or disorder is provided. In another aspect of the invention, a method for identifying a candidate agent useful in the treatment of a fibrosis-related disease is provided. In one embodiment, the method includes the steps of determining the level of IL-33 in a subject (e.g., in a sample obtained from the subject) in the absence of the candidate agent, administering to the subject or contacting the sample with the candidate agent, and determining the level of IL-33 after the administering or contacting, wherein an increase in the level of IL-33 indicates that the candidate agent is useful in the treatment of a cardiac disease or disorder or, in another embodiment, is useful in the treatment of a fibrosis-related disease.

In one embodiment, the sample is a body fluid sample from the subject. In another embodiment, the sample is a sample of cardiac cells or tissue from the subject.

In yet a further aspect of the invention, a method for identifying a candidate agent useful in the treatment of a cardiac disease or disorder is provided. In another aspect of the invention, a method for identifying a candidate agent useful in the treatment of a fibrosis-related disease is provided. In one embodiment, the method includes the step of determining the level of soluble ST2 in a subject (e.g., in a sample obtained from the subject) in the absence of the candidate agent, administering to the subject or contacting the sample (or another sample from the subject) with the candidate agent, and determining the level of soluble ST2 after the administering or contacting, wherein a decrease in the level of soluble ST2 indicates that the candidate agent is useful in the treatment of the cardiac disease or disorder or, in another embodiment, is useful in the treatment of a fibrosis-related disease.

In one embodiment, the sample is a body fluid sample from the subject. In another embodiment, the sample is a sample of cardiac cells or tissue from the subject.

In still a further aspect, forms are provided wherein values for the amount of IL-33 and/or soluble ST2 found in a subject are listed. In one embodiment, the form provides values for the relative ratio of soluble ST2 and IL-33. In one embodiment, the values are relative values. The values can be absolute values, in another embodiment. In still another embodiment, the form is in written or electronic form. In a further embodiment, the form can be viewed by a doctor or other medical person involved in treating a subject. In still a further embodiment, the form can be viewed by a subject. In one embodiment the form is in written form and can be sent to the subject. In another embodiment, the subject is one who has or is at risk of having a cardiovascular condition. In still another embodiment, the subject is one who is apparently healthy.

Each of the limitations of the invention can encompass various embodiments of the invention. It is, therefore, anticipated that each of the limitations of the invention involving any one element or combinations of elements can be included in each aspect of the invention. These and other aspects of the invention will be described in further detail in connection with the detailed description of the invention.

DETAILED DESCRIPTION OF THE INVENTION

Figure 1A:
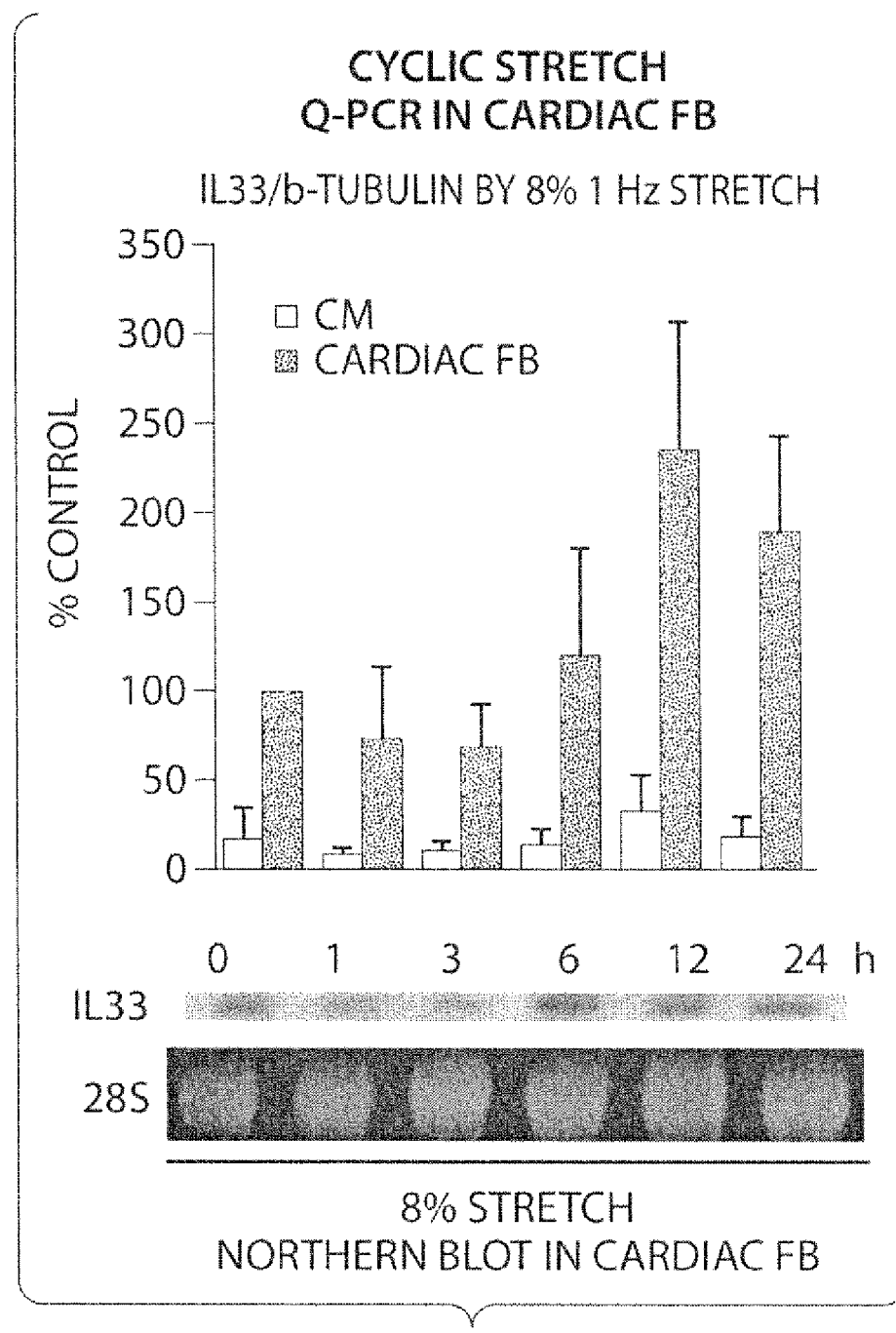
FIGS. 1A and 1B show that in cultured neonatal cardiac myocytes (CM) and cultured neonatal cardiac fibroblasts (FB), the gene for IL-33 is induced by cyclic mechanical stretch. In addition, in cardiac fibroblasts, the phorbol ester PMA is a powerful inducer.

It has been found that interleukin-33 (IL-33) signaling through membrane-bound ST2 has beneficial effects. For example, it has been found that signaling through membrane-bound ST2 is protective to the myocardium, and IL-33 as the ligand for ST2 is cardioprotective. In fact, purified IL-33 has been shown to prevent cardiac hypertrophy from known pathogens and to reduce cardiomyocyte apoptosis in culture. In addition, IL-33 can also prevent fibroblast proliferation in culture. Based on the results described herein, IL-33 can be used to treat or prevent cardiac diseases and disorders, such as cardiac hypertrophy, myocardial infarction, stroke, arteriosclerosis and heart failure, as well as fibrosis-related diseases, and methods for doing so are provided. Methods for using IL-33 in evaluating risk, diagnosing, determining the prognosis of a cardiac disease or disorder, and in evaluating therapeutic efficacy are also provided. Additionally, methods for reducing apoptosis or fibrosis with IL-33 are provided as are methods for increasing ST2L signaling, decreasing NF-κB activation, decreasing IκBα phosphorylation, decreasing P38MAPK phosphorylation, decreasing JNK phosphorylation, decreasing reactive oxygen species generation, decreasing macrophage infiltration and/or decreasing the expression of hypertrophic genes. Furthermore, compositions for use in the treatment or diagnosis of cardiac diseases and disorders as well as fibrosis-related diseases are also provided. It has also been found that soluble ST2 can decrease IL-33 signaling through membrane-bound ST2. An increase in signaling of endogenous IL-33 and/or exogenous IL-33 (i.e., IL-33 administered to a subject) through membrane-bound ST2 can be accomplished using soluble ST2 inhibiting agents. Therefore, soluble ST2 inhibiting agents can be used in addition to or in place of IL-33 in the compositions and methods provided.

As used herein, a "subject" is a human or a non-human mammal. In some embodiments, human subjects are preferred.

As used herein, a "cardiac disease or disorder" (also referred to herein as cardiovascular disease, disorder or condition) is any disease or disorder that negatively affects the cardiovascular system. The term is also intended to refer to cardiovascular events. "Cardiovascular events", as used herein, include acute coronary syndrome, myocardial infarction, myocardial ischemia, chronic stable angina pectoris, unstable angina pectoris, angioplasty, stroke, transient ischemic attack, claudication(s) and vascular occlusion(s). Cardiac diseases and disorders, therefore, include acute coronary syndrome, myocardial infarction, myocardial ischemia, chronic stable angina pectoris, unstable angina pectoris, angioplasty, stroke, transient ischemic attack, claudication(s), vascular occlusion(s), arteriosclerosis, heart failure and cardiac hypertrophy.

A "cardiac cell", as used herein, refers to a cardiomyocyte or a cardiac fibroblast. As used herein, "cardiomyocyte" and "cardiac myocyte" are used interchangeably.

As used herein, a "fibrosis-related disease" (i.e., a fibrotic disease) refers to any disease or disorder in which fibrosis is a pathologic basis, result or symptom. Fibrosis-related diseases include, for example, skin pathologic scarring, such as colloid and hypertrophic scarring; cirrhosis, such as cirrhosis of the liver or gallbladder; cardiac fibrosis; liver fibrosis; kidney fibrosis; pulmonary fibrosis; bone-marrow fibrosis; rheumatic heart disease; sclerosing peritonitis; glomerulosclerosis and scleroderma. Fibrosis can be the result of a number of factors. For instance, fibrosis can be induced by adrenergic and/or angiotensin receptor signaling, and, therefore, can be induced by agonists of adrenergic or angiotensin receptors. Such agonists include, for example, angiotensin II and phenylephrine. Fibrosis can also be induced by tissue injury. As used herein, "tissue injury" refers to any damage of or strain placed on a tissue such that there is a change that occurs in or to the tissue. Tissue injuries include cardiac tissue injury. One of ordinary skill in the art will readily recognize that cardiac tissue injury can result from cardiac strain or cardiac overload. Generally, the subjects in need of the methods and compositions provided herein, therefore, include those in which there is increased cardiac strain, such that there is an increased risk of developing a cardiac disease or disorder or a fibrosis-related disease.

"Cells associated with fibrosis" are cells that are involved with the fibrotic process or are affected by the fibrotic process. Cells associated with fibrosis include fibroblasts, such as cardiac fibroblasts.

An "IL-33 molecule" or "IL-33" refers to either a nucleic acid molecule encoding an IL-33 polypeptide or an IL-33 polypeptide itself. It can be human IL-33 but can also be IL-33 of another species (e.g., rat or mouse). Sequences for human, rat and mouse IL-33 are provided elsewhere herein by the recitation of GenBank Accession numbers. The IL-33 can, therefore, be the nucleic acid molecule encoding an IL-33 polypeptide or the IL-33 polypeptide itself represented by any of the sequences provided. In one embodiment, IL-33 is human IL-33.

As used herein, "ST2" and "membrane-bound ST2" or "ST2L" refers to the membrane-bound form of ST2, while "soluble ST2" refers to the soluble form. A nucleic acid and amino acid sequence of membrane-bound ST2 are provided by GenBank™ accession numbers NM_016232 and NP_057316, respectively. A nucleic acid and amino acid sequence of soluble ST2 are provided by GenBank™ accession numbers NM_003856 and NP_003847, respectively.

Subjects that have or are at risk of developing a cardiac disease or disorder can be treated by increasing IL-33 signaling through membrane-bound ST2. Methods for doing so can include the step of administering an effective amount of IL-33 and/or a soluble ST2 inhibiting agent to a subject in need thereof. As used herein, subjects that have or are at risk of developing a cardiac disease or disorder include subjects who have already been diagnosed (with the methods provided herein and/or those known in the art) as having a cardiac disease or disorder as well as subjects who would be regarded as being at risk of suffering from a cardiac disease or disorder at some point in the future. This latter group of subjects includes those at risk of suffering a cardiovascular event.

Methods are also provided for reducing apoptosis or fibrosis using IL-33 and/or a soluble ST2 inhibiting agent. Such methods include the step of contacting one or more cells associated with fibrosis with IL-33 and/or a soluble ST2 inhibiting agent in an effective amount to reduce apoptosis or fibrosis. Such methods can be carried out in vitro or in vivo. As used herein, "contacting" refers to placing an agent such that it interacts directly with one or more cells or indirectly such that the one or more cells are affected in some way as a result. When the methods are carried out in vivo, a subject is administered IL-33 and/or a soluble ST2 inhibiting agent in an amount effective to reduce apoptosis or fibrosis. Methods for assessing apoptotic or fibrotic reduction will be readily apparent to one of ordinary skill in the art. Examples of such methods are also provided herein below in the Examples. Subjects that have or are at risk of developing a fibrosis-related disease, therefore, can also be treated by increasing IL-33 signaling through membrane-bound ST2. Methods for doing so can include the step of administering an effective amount of IL-33 and/or a soluble ST2 inhibiting agent to a subject in need thereof.

Further methods are also provided herein that each produce a specific result (e.g., a decrease in activation of another molecule, a decrease in phosphorylation of another molecule, etc.). In one embodiment, this can be accomplished by increasing ST2L signaling, such as by contacting one or more cardiac cells with IL-33 and/or a soluble ST2 inhibiting agent. Experimental techniques for assessing or testing for these specific results are provided below in the Examples. Others will also be apparent to one of ordinary skill in the art.

In one embodiment, the cells that are contacted are or have been exposed to hypertrophic stimuli or are undergoing or have undergone hypertrophy. As used herein, "hypertrophic stimuli" is any agent or condition that causes or increases the risk of hypertrophy. Examples are provided herein of such agents or conditions and others would be known to those of ordinary skill in the art. Methods provided herein can also be used to decrease the expression of hypertrophic genes. A "hypertrophic gene" is any gene whose expression is altered as a response to hypertrophic stimuli. Hypertrophic genes include, for example, ANP and BNP.

The compositions and methods of treatment provided herein, in some embodiments, include IL-33 or the administration of IL-33, respectively. The IL-33 can be administered as an IL-33 polypeptide or as a nucleic acid encoding an IL-33 polypeptide. When a nucleic acid encoding an IL-33 polypeptide is administered, the administration of the nucleic acid results in the expression of the encoded IL-33 polypeptide in the subject. A nucleic acid and amino acid sequence of human IL-33 are provided by GenBank™ Accession No. AY905581 and AAX86998, respectively.

As used herein, an "IL-33 polypeptide" is intended to include the full-length IL-33 protein, functional fragments thereof and conservatively substituted versions thereof. As used herein, the functional fragments retain a distinct functional capability as found with the full-length protein. The functional capability can be interaction with antibodies, interaction with other polypeptides or molecules, etc. Preferably, the functional capability is an activity of the full-length IL-33 protein (e.g., its ability to act as an agonist of membrane-bound ST2, its ability to inhibit cardiac hypertrophy, to inhibit apoptosis, to inhibit fibrosis, etc.). Methods for measuring a functional capability of IL-33 are well known in the art, and some examples are provided herein below in the Examples. In some embodiments, the fragment is 8, 10, 12, 15, 20, 25, 30, 35, 40, 45, 50, 55, 60, 65, 70, 75, 100, 125, 150, 200, 225, 250 or 269 amino acids long. In other embodiments, the fragment is of any integer length between 8 and 269 amino acids.

The skilled artisan will realize that conservative amino acid substitutions may be made in any of the foregoing polypeptides. As used herein, a "conservative amino acid substitution" refers to an amino acid substitution which does not significantly alter the tertiary structure and/or activity of the polypeptide. Conservatively substituted versions of the foregoing polypeptides can be prepared according to methods for altering polypeptide sequences known to one of ordinary skill in the art, and include those that are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Conservatively substituted versions of the polypeptides can also be made by alteration of a nucleic acid encoding the polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a polypeptide.

The polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Those skilled in the art also can readily follow known methods for isolating polypeptides. These include, but are not limited to, immunochromatography, HPLC, size-exclusion chromatography, ion-exchange chromatography and immune-affinity chromatography. Polypeptides can also be synthesized chemically using well-established methods of peptide synthesis.

The polypeptides can be, in some embodiments, isolated polypeptides. As used herein with respect to polypeptides, the term "isolated" means separated from its native environment in sufficiently pure form so that it can be manipulated or used for any of the purposes of the invention. Thus, isolated means sufficiently pure to be used, for example, to raise and/or isolate antibodies, as a therapeutic agent, etc.

IL-33 can be administered in the form of a nucleic acid encoding an IL-33 polypeptide. In some embodiments, the nucleic acid encoding an IL-33 polypeptide is part of an expression vector, and the expression vector is administered to the subject. In another embodiment, the nucleic acid encoding an IL-33 polypeptide is part of an expression vector within a host cell, and the host cell is administered to the subject.

The nucleic acids, in some embodiments, are isolated nucleic acids. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulated by recombinant DNA techniques well known in the art. Thus, a nucleotide sequence contained in a vector in which 5' and 3' restriction sites are known or for which polymerase chain reaction (PCR) primer sequences have been disclosed is considered isolated, but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulated by standard techniques known to those of ordinary skill in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art, and genes which visibly affect the phenotype of transformed or transfected cells, hosts, colonies or plaques. Preferred vectors are those capable of autonomous replication and expression of the structural gene products present in the DNA segments to which they are operably joined.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Such 5' non-transcribed regulatory sequences will often include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art. Expression vectors containing all the necessary elements for expression are commercially available and known to those skilled in the art.

As mentioned above, soluble ST2 inhibiting agents can be used in the methods provided herein in place of or in addition to IL-33. This is due to the discovery that IL-33 beneficially signals through membrane-bound ST2 and that this signaling can be inhibited by the soluble form of ST2. The compositions and methods of treatment provided herein, therefore, in some embodiments, include the administration of a soluble ST2 inhibiting agent. As used herein, a "soluble ST2 inhibiting agent" is an agent that reduces or eliminates the expression of soluble ST2 or somehow interferes with its binding to IL-33. These agents are not intended to significantly reduce or eliminate the expression of membrane-bound ST2 or significantly interfere with the binding of membrane-bound ST2 to IL-33.

As an example, a soluble ST2 inhibiting agent, can be an antibody or antigen-binding fragment thereof that specifically binds soluble ST2 protein but not membrane-bound ST2 protein. Again, one of ordinary skill in the art will readily recognize that antibodies can be produced that specifically bind soluble ST2 but not membrane-bound ST2 and interfere with soluble ST2 binding of IL-33. In some embodiments, the antibodies are monoclonal, polyclonal or a mixture thereof. In other embodiments, the antibodies are chimeric, human or humanized. In still other embodiments, the antibody is a single chain antibody. In yet other embodiments, the soluble ST2 inhibiting agent is an intrabody.

Antibodies and methods of their production are well known to those of ordinary skill in the art. As used herein, the term "antibody" means not only intact antibody molecules but also fragments of antibody molecules retaining specific binding ability. Such fragments are also well known in the art and are regularly employed both in vitro and in vivo. In particular, as used herein, the term "antibody" means not only intact immunoglobulin molecules but also the well-known active fragments $F(ab')_2$, and Fab.

According to one embodiment, the molecule is an intact soluble monoclonal antibody in an isolated form or in a pharmaceutical preparation. An intact soluble monoclonal antibody, as is well known in the art, is an assembly of polypeptide chains linked by disulfide bridges. Two principle polypeptide chains, referred to as the light chain and heavy chain, make up all major structural classes (isotypes) of antibody. Both heavy chains and light chains are further divided into subregions referred to as variable regions and constant regions. As used herein the term "monoclonal antibody" refers to a homogenous population of immunoglobulins which specifically bind to an epitope (i.e., antigenic determinant).

Significantly, as is well-known in the art, only a small portion of an antibody molecule, the paratope, is involved in the binding of the antibody to its epitope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-know in the art, there are complementarity determining regions (CDRs), which directly interact with the epitope of the antigen, and framework regions (Frs), which maintain the tertiary structure of the paratope (see, in general, Clar, 1986; Roitt, 1991). In both the heavy chain Fd fragment and the light chain of IgG immunoglobulins, there are four framework regions (FR1 through FR4) separated, respectively, by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also encompasses F(ab')$_2$, Fab, Fv and Fd fragments; chimeric antibodies in which the Fc and/or Fr and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences.

Human monoclonal antibodies may be made by any of the methods known in the art, such as those disclosed in U.S. Pat. No. 5,567,610, issued to Borrebaeck et al., U.S. Pat. No. 5,565,354, issued to Ostberg, U.S. Pat. No. 5,571,893, issued to Baker et al, Kozber, J. Immunol. 133: 3001 (1984), Brodeur, et al., Monoclonal Antibody Production Techniques and Applications, p. 51-63 (Marcel Dekker, Inc, new York, 1987), and Boerner et al., J. Immunol., 147: 86-95 (1991). In addition to the conventional methods for preparing human monoclonal antibodies, such antibodies may also be prepared by immunizing transgenic animals that are capable of producing human antibodies (e.g., Jakobovits et al., PNAS USA, 90: 2551 (1993), Jakobovits et al., Nature, 362: 255-258 (1993), Bruggermann et al., Year in Immuno., 7:33 (1993) and U.S. Pat. No. 5,569,825 issued to Lonberg).

The antibodies of the invention may be single chain antibodies or may be single domain antibodies (intrabodies or intracellular antibodies). Intrabodies are generally known in the art as single chain Fv fragments with domains of the immunoglobulin heavy (VH) and light chains (VL). Single-chain antibodies can be constructed in accordance with the methods described in U.S. Pat. No. 4,946,778 to Ladner et al. Such single-chain antibodies include the variable regions of the light and heavy chains joined by a flexible linker moiety.

Soluble ST2 inhibiting agents also include, for example, isolated nucleic acid molecules that specifically bind mRNA transcripts encoding soluble ST2 but not mRNA transcripts encoding membrane-bound ST2. One of ordinary skill in the art will readily recognize that, as the 5' untranslated region (UTR) and 3' region of soluble ST2 mRNA are different from the mRNA of the membrane-bound form, nucleic acid molecules can be designed to target soluble ST2 mRNA but not membrane-bound ST2 mRNA and reduce or eliminate soluble ST2 expression.

RNAi and antisense molecules, therefore, are included as part of the invention. The use of RNA interference or "RNAi" involves the use of double-stranded RNA (dsRNA) to block gene expression (see, e.g. Sui, G, et al, Proc Natl. Acad. Sci. U.S.A. 99:5515-5520, 2002). Methods of applying RNAi strategies in embodiments of the invention will be known to one of ordinary skill in the art.

As used herein, a "siRNA molecule" is a double stranded RNA molecule (dsRNA) consisting of a sense and an antisense strand, which are complementary (Tuschl, T. et al., 1999, Genes & Dev., 13:3191-3197; Elbashir, S. M. et al., 2001, EMBO J., 20:6877-6888). In one embodiment the last nucleotide at the 3' end of the antisense strand may be any nucleotide and is not required to be complementary to the region of the target gene. The siRNA molecule may be 19-23 nucleotides in length in some embodiments. In other embodiments, the siRNA is longer but forms a hairpin structure of 19-23 nucleotides in length. In still other embodiments, the siRNA is formed in the cell by digestion of double stranded RNA molecule that is longer than 19-23 nucleotides. The siRNA molecule preferably includes an overhang on one or both ends, preferably a 3' overhang, and more preferably a two nucleotide 3' overhang on the sense strand. In another preferred embodiment, the two nucleotide overhang is thymidine-thymidine (TT). The siRNA molecule corresponds to at least a portion of a target gene. In one embodiment the siRNA molecule corresponds to a region selected from a cDNA target gene beginning between 50 to 100 nucleotides downstream of the start codon. In a preferred embodiment the first nucleotide of the siRNA molecule is a purine. Many variations of siRNA and other double stranded RNA molecules useful for RNAi inhibition of gene expression will be known to one of ordinary skill in the art.

The siRNA molecules can be plasmid-based. In a preferred method, a polypeptide encoding sequence of soluble ST2 is amplified using the well known technique of polymerase chain reaction (PCR). The use of the entire polypeptide encoding sequence is not necessary; as is well known in the art, a portion of the polypeptide encoding sequence is sufficient for RNA interference. For example, the PCR fragment can be inserted into a vector using routine techniques well known to those of skill in the art. The insert can be placed between two promoters oriented in opposite directions, such that two complementary RNA molecules are produced that hybridize to form the siRNA molecule. Alternatively, the siRNA molecule is synthesized as a single RNA molecule that self-hybridizes to form a siRNA duplex, preferably with a non-hybridizing sequence that forms a "loop" between the hybridizing sequences. In one embodiment the siRNA is synthesized with plasmids that are controlled by a tissue-specific promoter.

In one aspect of the invention a vector comprising a nucleotide coding for soluble ST2 (e.g., human ST2) is provided, preferably one that includes promoters active in mammalian cells. Non-limiting examples of vectors are the pSUPER RNAi series of vectors (Brummelkamp, T. R. et al., 2002, Science, 296:550-553; available commercially from OligoEngine, Inc., Seattle, Wash.). In one embodiment a partially self-complementary nucleotide coding sequence can be inserted into the mammalian vector using restriction sites, creating a stem-loop structure. In a preferred embodiment, the mammalian vector comprises the polymerase-III H1-RNA gene promoter. The polymerase-III H1-RNA promoter produces a RNA transcript lacking a polyadenosine tail and has a well-defined start of transcription and a termination signal consisting of five thymidines (T5) in a row. The cleavage of the transcript at the termination site occurs after the second uridine and yields a transcript resembling the ends of synthetic siRNAs containing two 3' overhanging T or U nucleotides. Other promoters useful in siRNA vectors will be known to one of ordinary skill in the art.

Vector systems for siRNA expression in mammalian cells include pSUPER RNAi system described above. Other examples include but are not limited to pSUPER.neo, pSUPER.neo+gfp and pSUPER.puro (OligoEngine, Inc.); BLOCK-iT T7-TOPO linker, pcDNA1.2/V5-GW/lacZ, pENTR/U6, pLenti6-GW/U6-laminshrna and pLenti6/BLOCK-iT-DEST (Invitrogen). These vectors and others are available from commercial suppliers.

In some embodiments, the antisense oligonucleotides correspond to N-terminal or 5' upstream sites such as translation initiation, transcription initiation or promoter sites. In addition, 3'-untranslated regions may be targeted. In addition, the antisense is targeted, preferably, to sites in which mRNA secondary structure is not expected (see, e.g., Sainio et al., *Cell Mol. Neurobiol.* 14(5):439-457, 1994) and at which proteins are not expected to bind. The present invention also provides for antisense oligonucleotides which are complementary to the genomic DNA.

The methods and compositions of the invention are useful in both acute and prophylactic treatment of any of the diseases or disorders as described herein. As used herein, an acute treatment refers to the treatment of subjects having a particular disease or disorder. Prophylactic treatment refers to the treatment of subjects at risk of having the disease or disorder, but not presently having or experiencing the symptoms of the disease or disorder. In its broadest sense, the terms "treatment" or "to treat" refer to both acute and prophylactic treatments. If the subject in need of treatment has a particular disease or disorder, then treating the disease or disorder refers to ameliorating, reducing or eliminating the disease or disorder or one or more symptoms arising from the disease or disorder. In some preferred embodiments, treating the disease or disorder refers to ameliorating, reducing or eliminating a specific symptom or a specific subset of symptoms associated with the disease or disorder. If the subject in need of treatment is one who is at risk of developing a disease or disorder, then treating the subject refers to reducing the risk of the subject developing the disease or disorder.

Subjects who would benefit from the methods and compositions of the invention, therefore, include those who are undergoing therapy (i.e., a subject "on therapy"). A subject on therapy is a subject who already has been diagnosed and is in the course of treatment with a therapy for treating a cardiac disease or disorder or a fibrosis-related disease or reducing the risk of developing a cardiac disease or disorder or a fibrosis-related disease. The therapy can be any that includes the use of the therapeutic agents referred to herein or otherwise known in the art. The therapy also can be non-drug treatments such as diet and/or exercise. In some embodiments, the therapy (for a cardiac disease or disorder) includes the use of a therapeutic agent which lowers levels of CRP. In other embodiments, the therapy (for a cardiac disease or disorder) includes the use of a statin. In further embodiments, the subject is a subject on therapy (for a cardiac disease or disorder) and who has a CRP level above 1 mg/L. The therapy for a fibrosis-related disease, for example, can be the use of an anti-inflammatory agent or an immunosuppressive agent.

In some embodiments, the subject already has had a primary (first) cardiovascular event, such as, for example, a myocardial infarct or has had an angioplasty. A subject who has had a primary cardiovascular event is at an elevated risk of a secondary (second) cardiovascular event. In some embodiments, the subject has not had a primary cardiovascular event, but is at an elevated risk of having a cardiovascular event because the subject has one or more risk factors. Examples of risk factors for a primary cardiovascular event include: hyperlipidemia, obesity, diabetes mellitus, hypertension, pre-hypertension, elevated level(s) of a marker of systemic inflammation, age, a family history of cardiovascular events and cigarette smoking. The degree of risk of a cardiovascular event depends on the multitude and the severity or the magnitude of the risk factors that the subject has. Risk charts and prediction algorithms are available for assessing the risk of cardiovascular events in a subject based on the presence and severity of risk factors. One such example is the Framingham Heart Study risk prediction score. The subject is at an elevated risk of having a cardiovascular event if the subject's 10-year calculated Framingham Heart Study risk score is greater than 5%, 6%, 7%, 8%, 9%, 10%, 11%, 12%, 13%, 14%, 15%, 16%, 17%, 18%, 19%, 20% or more. Another method for assessing the risk of a cardiovascular event in a subject is a global risk score that incorporates a measurement of a level of a marker of systemic inflammation, such as CRP, into the Framingham Heart Study risk prediction score. Other methods of assessing the risk of a cardiovascular event in a subject include coronary calcium scanning, cardiac magnetic resonance imaging and/or magnetic resonance angiography.

In still other embodiments, the subject has had a primary cardiovascular event and has one or more other risk factors. In one embodiment, the subject is on statin therapy to reduce lipid levels. In another embodiment, the subject has healthy lipid levels (i.e., the subject is not hyperlipidemic).

In some embodiments, the subject is having or has had a stroke. Stroke (also referred to herein as ischemic stroke and/or cerebrovascular ischemia) is often cited as the third most common cause of death in the industrial world, ranking behind ischemic heart disease and cancer. Strokes are responsible for about 300,000 deaths annually in the United States and are a leading cause of hospital admissions and long-term disabilities. Accordingly, the socioeconomic impact of stroke and its attendant burden on society is practically immeasurable. "Stroke" is defined by the World Health Organization as a rapidly developing clinical sign of focal or global disturbance of cerebral function with symptoms lasting at least 24 hours. Strokes are also implicated in deaths where there is no apparent cause other than an effect of vascular origin.

Strokes are typically caused by blockages or occlusions of the blood vessels to the brain or within the brain. With complete occlusion, arrest of cerebral circulation causes cessation of neuronal electrical activity within seconds. Within a few minutes after the deterioration of the energy state and ion homeostasis, depletion of high energy phosphates, membrane ion pump failure, efflux of cellular potassium, influx of sodium chloride and water, and membrane depolarization occur. If the occlusion persists for more than five to ten minutes, irreversible damage results. With incomplete ischemia, however, the outcome is difficult to evaluate and depends largely on residual perfusion and the availability of oxygen. After a thrombotic occlusion of a cerebral vessel, ischemia is rarely total. Some residual perfusion usually persists in the ischemic area, depending on collateral blood flow and local perfusion pressure.

Cerebral blood flow can compensate for drops in mean arterial blood pressure from 90 to 60 mm Hg by autoregulation. This phenomenon involves dilatation of downstream resistant vessels. Below the lower level of autoregulation (about 60 mm Hg), vasodilatation is inadequate and the cerebral blood flow falls. The brain, however, has perfusion reserves that can compensate for the fall in cerebral blood flow. This reserve exists because under normal conditions only about 35% of the oxygen delivered by the blood is extracted. Therefore, increased oxygen extraction can take place, provided that normoxia and normocapnea exist. When distal blood pressure falls below approximately 30 mm Hg, the two compensatory mechanisms (autoregulation and perfusion reserve) are inadequate to prevent failure of oxygen delivery.

As blood flow drops below the ischemic threshold of 23 ml/100 g/minute, symptoms of tissue hypoxia develop. Severe ischemia may be lethal. When the ischemia is moderate, it will result in "penumbra." In the neurological context, penumbra refers to a zone of brain tissue with moderate ischemia and paralyzed neuronal function, which is reversible with restoration of adequate perfusion. The penumbra forms a zone of collaterally perfused tissue surrounding a core of severe ischemia in which an infarct has developed. In other words, the penumbra is the tissue area that can be saved, and is essentially in a state between life and death.

Although an ischemic event can occur anywhere in the vascular system, the carotid artery bifurcation and the origin of the internal carotid artery are the most frequent sites for thrombotic occlusions of cerebral blood vessels, which result in cerebral ischemia. The symptoms of reduced blood flow due to stenosis or thrombosis are similar to those caused by middle cerebral artery disease. Flow through the ophthalmic artery is often affected sufficiently to produce amaurosis fugax or transient monocular blindness. Severe bilateral internal carotid artery stenosis may result in cerebral hemispheric hypoperfusion. This manifests with acute headache ipsilateral to the acutely ischemic hemisphere. Occlusions or decrease of the blood flow with resulting ischemia of one anterior cerebral artery distal to the anterior communicating artery produces motor and cortical sensory symptoms in the contralateral leg and, less often, proximal arm. Other manifestations of occlusions or underperfusion of the anterior cerebral artery include gait ataxia and sometimes urinary incontinence due to damage to the parasagittal frontal lobe. Language disturbances manifested as decreased spontaneous speech may accompany generalized depression of psychomotor activity.

Most ischemic strokes involve portions or all of the territory of the middle cerebral artery with emboli from the heart or extracranial carotid arteries accounting for most cases. Emboli may occlude the main stem of the middle cerebral artery, but more frequently produce distal occlusion of either the superior or the inferior branch. Occlusions of the superior branch cause weakness and sensory loss that are greatest in the face and arm. Occlusions of the posterior cerebral artery distal to its penetrating branches cause complete contralateral loss of vision. Difficulty in reading (dyslexia) and in performing calculations (dyscalculia) may follow ischemia of the dominant posterior cerebral artery. Proximal occlusion of the posterior cerebral artery causes ischemia of the branches penetrating to calamic and limbic structures. The clinical results are hemisensory disturbances that may chronically change to intractable pain of the defective side (thalamic pain).

A subject having a stroke is so diagnosed by symptoms experienced and/or by a physical examination including interventional and non-interventional diagnostic tools such as CT and MR imaging. A subject having a stroke may present with one or more of the following symptoms: paralysis, weakness, decreased sensation and/or vision, numbness, tingling, aphasia (e.g., inability to speak or slurred speech, difficulty reading or writing), agnosia (i.e., inability to recognize or identify sensory stimuli), loss of memory, co-ordination difficulties, lethargy, sleepiness or unconsciousness, lack of bladder or bowel control and cognitive decline (e.g., dementia, limited attention span, inability to concentrate). Using medical imaging techniques, it may be possible to identify a subject having a stroke as one having an infarct or one having hemorrhage in the brain.

In other embodiments, the subject is at risk of suffering from an ischemic stroke. As used herein, subjects at risk of an ischemic stroke are a category determined according to conventional medical practice. Subjects at risk include, for example, subjects who are having elective vascular surgery. Subjects at risk also include those who exhibit risk factors, such as hypertension, hypercholesterolemia and smoking. Atrial fibrillation or recent myocardial infarction are also important risk factors. Additionally, subjects at risk of an ischemic stroke also include subjects undergoing surgical or diagnostic procedures which risk release of emboli, lowering of blood pressure or decrease in blood flow to the brain, such as carotid endarterectomy, brain angiography, neurosurgical procedures in which blood vessels are compressed or occluded, cardiac catheterization, angioplasty, including balloon angioplasty, coronary by-pass surgery or similar procedures. Subjects at risk of an ischemic stroke also include subjects having any cardiac condition (disease or disorder) that may lead to decreased blood flow to the brain, such as atrial fibrillation, ventricular tachycardia, dilated cardiomyopathy and other cardiac conditions requiring anticoagulation. Subjects at risk of an ischemic stroke also include subjects having conditions including arteriopathy or brain vasculitis, such as that caused by lupus, congenital diseases of blood vessels, such as CADASIL syndrome, or migraine, especially prolonged episodes.

The treatment of stroke with the compositions and methods provided can be for patients who have experienced a stroke or can be a prophylactic treatment. Short term prophylactic treatment is indicated for subjects having surgical or diagnostic procedures which risk release of emboli, lowering of blood pressure or decrease in blood flow to the brain, to reduce the injury due to any ischemic event that occurs as a consequence of the procedure. Longer term or chronic prophylactic treatment is indicated for subjects having cardiac conditions that may lead to decreased blood flow to the brain, or conditions directly affecting brain vasculature. If prophylactic, then the treatment is for subjects at risk of an ischemic stroke, as described above. If the subject has experienced a stroke, then the treatment can include acute treatment. Acute treatment for stroke subjects means administration of a composition of the invention at the onset of symptoms of the condition or within 48 hours of the onset, preferably within 24 hours, more preferably within 12 hours, more preferably within 6 hours, and even more preferably within 1, 2 or 3 hours of the onset of symptoms of the condition or immediately at the time of diagnosis or at the time medical personnel suspects a stroke has occurred.

In still other embodiments, the subject can be one that has a myocardial infarction or is at risk of having a myocardial infarction. By "having a myocardial infarction" it is meant that the subject is currently having or has suffered a myocardial infarction. It is believed that immediate administration of the compositions of the invention could greatly benefit the subject.

By "immediate" it is meant that administration occurs before (if it is suspected or diagnosed in time), or within 48 hours, although administration later, such as, for example, within 14 days, after a cardiovascular event or diagnosis or suspicion of cardiac disease or disorder may also be beneficial to the subject. Immediate administration can also include administration within 15, 20, 30, 40 or 50 minutes, within 1, 2, 3, 4, 5, 6, 7, 8, 9, 10, 12, 15, 18, 20 or 22 hours or within 1 or 2 days of the diagnosis or suspicion of a cardiovascular event or cardiac disease or disorder. In still another embodiment, IL-33 can be administered for a few days, one week or a few weeks (e.g., 1, 2, 3 or 4 weeks) beginning at or shortly after the time of diagnosis or suspicion of the cardiovascular event or cardiac disease or disorder.

"Myocardial infarction" is a focus of necrosis resulting from inadequate perfusion of the cardiac tissue. Myocardial infarction generally occurs with the abrupt decrease in coronary blood flow that follows a thrombotic occlusion of a coronary artery previously narrowed by atherosclerosis. Generally, infarction occurs when an atherosclerotic plaque fissures, ruptures, or ulcerates, and a mural thrombus forms leading to coronary artery occlusion.

A number of laboratory tests for the diagnosis of myocardial infarction are well known in the art. Generally, the tests may be divided into four main categories: (1) nonspecific indexes of tissue necrosis and inflammation, (2) electrocardiograms, (3) serum enzyme changes (e.g., creatine phosphokinase levels) and (4) cardiac imaging. A person of ordinary skill in the art could easily apply any of the foregoing tests to determine when a subject is at risk, is suffering, or has suffered, a myocardial infarction.

The subject can also be one who has or is at risk of arteriosclerosis. Arteriosclerosis is a term used to describe a thickening and hardening of the arterial wall. It is believed to be responsible for the majority of deaths in the United States and in most westernized societies. Atherosclerosis is one type of arteriosclerosis that is believed to be the cause of most coronary artery disease, aortic aneurysm and arterial disease of the lower extremities (including peripheral vascular arteriopathy), as well as contributing to cerebrovascular disease. Atherosclerosis is the leading cause of death in the United States.

A normal artery typically is lined on its inner-side only by a single layer of endothelial cells, the intima. The intima overlays the media, which contains only a single cell type, the smooth muscle cell. The outer-most layer of the artery is the adventitia. With aging, there is a continuous increase in the thickness of the intima, believed to result in part from migration and proliferation of smooth muscle cells from the media. A similar increase in the thickness of the intima also occurs as a result of various traumatic events or interventions, such as occurs when, for example, a balloon dilatation procedure causes injury to the vessel wall. The compositions and methods provided can be used in connection with treating ischemic injury resulting from arteriosclerotic conditions. An arteriosclerotic condition as used herein means classical atherosclerosis, accelerated atherosclerosis, atherosclerosis lesions and any other arteriosclerotic conditions characterized by undesirable endothelial and/or vascular smooth muscle cell proliferation, including vascular complications of diabetes.

The subject can also be one who has or is at risk of heart failure. Heart failure is a clinical syndrome of diverse etiologies linked by the common denominator of impaired heart pumping and is characterized by the failure of the heart to pump blood commensurate with the requirements of the metabolizing tissues, or to do so only from an elevating filling pressure.

In yet other embodiments, the subject has or is at risk of cardiac hypertrophy. This condition is typically characterized by left ventricular hypertrophy, usually of a nondilated chamber, without obvious antecedent cause. Current methods of diagnosis include the electrocardiogram and the echocardiogram. Many patients, however, are asymptomatic and may be relatives of patients with known disease. Unfortunately, the first manifestation of the disease may be sudden death, frequently occurring in children and young adults, often during or after physical exertion.

In still another embodiment, the subject is hyperlipidemic. Hyperlipidemia is hypercholesterolemia and/or hypertriglyceridemia. Hypercholesterolemic subjects and hypertriglyceridemic subjects are associated with increased incidence of cardiovascular events. A hypercholesterolemic subject is one who fits the current criteria established for a hypercholesterolemic subject. A hypertriglyceridemic subject is one who fits the current criteria established for a hypertriglyceridemic subject. A hypercholesterolemic subject has an LDL level of >160 mg/dL, or an LDL level >130 mg/dL and at least two risk factors selected from the group consisting of: male gender, family history of premature coronary heart disease, cigarette smoking, hypertension, low HDL (<35 mg/dL), diabetes mellitus, hyperinsulinemia, abdominal obesity, high lipoprotein and personal history of a cardiovascular event. A hypertriglyceridemic subject has a triglyceride (TG) level of >250 mg/dL.

In yet another embodiment, the subject is hypertensive or pre-hypertensive. Hypertension is defined as a systolic blood pressure >140 mm Hg and/or a diastolic pressure >90 mm Hg. Pre-hypertension is defined as systolic blood pressure between 115 and 140 mm Hg, and/or a diastolic pressure between 80 and 90 mm Hg.

In still another embodiment, the subject has diabetes mellitus. Diabetes mellitus is established in a human subject with a fasting plasma glucose level of 125 mg/dL or higher.

In a further embodiment, the subject has a body mass index (BMI) greater than 25 or is considered obese. Obesity is a state of excess adipose tissue mass. Although not a direct measure of adiposity, the most widely used method to gauge obesity is the body mass index (BMI), which is equal to weight/height$^2$ (in kg/m$^2$) (See, e.g., Harrison's Principles of Experimental Medicine, 15th Edition, McGraw-Hill, Inc., N.Y.—hereinafter "Harrison's"). Based on data of substantial morbidity, a BMI of 30 is most commonly used as a threshold for obesity in both men and women. A BMI between 25 and 30 should be viewed as medically significant and worthy of therapeutic intervention, especially in the presence of risk factors that are influenced by adiposity, such as hypertension and glucose intolerance. Although often viewed as equivalent to increased body weight, this need not be the case. Lean but very muscular individuals may be overweight by arbitrary standards without having increased adiposity. Other approaches to quantifying obesity include anthropometry (skin-fold thickness), densitometry (underwater weighing), computed tomography (CT) or magnetic, resonance imaging (MRI), and/or electrical impedance.

In another embodiment, the subject has an elevated level of a marker of a cardiac disease or disorder or risk thereof. The marker can be, for example, cholesterol, low density lipoprotein cholesterol (LDLC) or a marker of systemic inflammation. An elevated level(s) of a marker is a level that is above the average for a healthy subject population (e.g., human subjects who have no signs and symptoms of a cardiac disease or disorder). When the marker is CRP, a CRP level of >1 is considered to be an elevated level.

In still a further embodiment, the subject has or is at risk of having a fibrosis-related disease.

It has also been found that IL-33 is expressed in cardiac cells that are mechanically stimulated. Therefore, the level of IL-33 expressed in a subject can be indicative of whether or not the subject is in need of treatment with one or more of the compositions provided herein. Subjects, therefore, include those with aberrant expression of IL-33, and methods are provided that include the step of selecting a subject on the basis that the subject has aberrant expression of IL-33. Therefore, methods are provided that include the step of selecting a subject on the basis that the subject expresses IL-33 above a predetermined value.

It has been also found that IL-33 signaling through membrane-bound ST2 is beneficial but that this benefit can be abolished by IL-33 binding to soluble ST2. Therefore, subjects that are in need of treatment also include those that express or have increased expression of soluble ST2. Therefore, methods are provided that include the step of selecting a subject for treatment on the basis that the subject expresses soluble ST2 or expresses soluble ST2 above a predetermined value. Experimental methods for determining the expression of soluble ST2 are known to those of ordinary skill in the art and include those described below.

"Expression," as used herein, refers to nucleic acid and/or polypeptide expression. "Aberrant expression" refers to increased expression (upregulation or overexpression) or decreased expression (downregulation or underexpression) in comparison with a control (e.g., expression in a healthy or "normal" subject).

In one embodiment, a "healthy subject," refers to a subject who does not have a cardiac disease or disorder and/or a fibrosis-related disease and is not at a recognizable risk of developing the cardiac disease or disorder and/or the fibrosis-related disease. Such healthy subjects also do not otherwise exhibit symptoms of a cardiac disease or disorder and/or a fibrosis-related disease. In other words, such subjects, if examined by a medical professional, would be characterized as healthy and free of symptoms of cardiac disease or disorder and/or fibrosis-related disease. An "apparently healthy subject" is one who would be deemed to be a healthy subject (and not have a cardiac disease or disorder and/or a fibrosis-related disease) with the methods of diagnosis known in the art. In some embodiments, the apparently healthy subject would be diagnosed with a cardiac disease or disorder or being at risk thereof with the methods of diagnosis provided herein (i.e., methods which include determining the expression level of IL-33 in a subject) but not those known in the art.

In some embodiments, the subject selected for treatment is one who expresses IL-33 or soluble ST2 at any level or has above-normal expression of IL-33 or soluble ST2 (as compared to the expression level of IL-33 or soluble ST2 in a healthy subject). In other embodiments, the subject selected for treatment has below-normal expression of IL-33. In some embodiments, the level of IL-33 expression is compared to levels of IL-33 that have been found to be beneficial in treating subjects that have a cardiac disease or disorder or a fibrosis-related disease or that have been found to inhibit the development of a cardiac disease or disorder or a fibrosis-related disease. Subjects are selected for treatment, in some embodiments, if they express IL-33 at levels that are below the levels of IL-33 that have been found to be beneficial. In other embodiments, the IL-33, or soluble ST2 inhibiting agent, is administered to a subject to raise the IL-33 level, or level of endogenous IL-33 not bound to soluble ST2, to or above a predetermined value. It follows, that in some embodiments, this predetermined value is the value found to be beneficial in the treatment of subjects as described above.

The compositions and methods provided herein for treating a subject in need thereof can include the use of additional therapeutic agents. Such additional therapeutic agents include anti-lipemic agents, anti-inflammatory agents, anti-thrombotic agents, fibrinolytic agents, anti-platelet agents, direct thrombin inhibitors, glycoprotein IIb/IIIa receptor inhibitors, agents that bind to cellular adhesion molecules and inhibit the ability of white blood cells to attach to such molecules (e.g., anti-cellular adhesion molecule antibodies), alpha-adrenergic blockers, beta-adrenergic blockers, cyclooxygenase-2 inhibitors, angiotensin system inhibitor, anti-arrhythmics, calcium channel blockers, diuretics, inotropic agents, vasodilators, vasopressors, thiazolidinediones, cannabinoid-1 receptor blockers, immunosuppressive agents and any combination thereof.

Anti-lipemic agents are agents that reduce total cholesterol, reduce LDLC, reduce triglycerides, and/or increase HDLC. Anti-lipemic agents include statins, non-statin anti-lipemic agents and combinations thereof. Statins are a class of medications that have been shown to be effective in lowering human total cholesterol, LDLC and triglyceride levels. Statins act at the step of cholesterol synthesis. By reducing the amount of cholesterol synthesized by the cell, through inhibition of the HMG-CoA reductase gene, statins initiate a cycle of events that culminates in the increase of LDLC uptake by liver cells. As LDLC uptake is increased, total cholesterol and LDLC levels in the blood decrease. Lower blood levels of both factors are associated with lower risk of atherosclerosis and heart disease, and the statins are widely used to reduce atherosclerotic morbidity and mortality.

Examples of statins include, but are not limited to, simvastatin (Zocor), lovastatin (Mevacor), pravastatin (Pravachol), fluvastatin (Lescol), atorvastatin (Lipitor), cerivastatin (Baycol), rosuvastatin (Crestor), pitivastatin and numerous others described in U.S. Pat. No. 4,444,784, U.S. Pat. No. 4,231,938, U.S. Pat. No. 4,346,227, U.S. Pat. No. 4,739,073, U.S. Pat. No. 5,273,995, U.S. Pat. No. 5,622,985, U.S. Pat. No. 5,135,935, U.S. Pat. No. 5,356,896, U.S. Pat. No. 4,920,109, U.S. Pat. No. 5,286,895, U.S. Pat. No. 5,262,435, U.S. Pat. No. 5,260,332, U.S. Pat. No. 5,317,031, U.S. Pat. No. 5,283,256, U.S. Pat. No. 5,256,689, U.S. Pat. No. 5,182,298, U.S. Pat. No. 5,369,125, U.S. Pat. No. 5,302,604, U.S. Pat. No. 5,166,171, U.S. Pat. No. 5,202,327, U.S. Pat. No. 5,276,021, U.S. Pat. No. 5,196,440, U.S. Pat. No. 5,091,386, U.S.

Pat. No. 5,091,378, U.S. Pat. No. 4,904,646, U.S. Pat. No. 5,385,932, U.S. Pat. No. 5,250,435, U.S. Pat. No. 5,132,312, U.S. Pat. No. 5,130,306, U.S. Pat. No. 5,116,870, U.S. Pat. No. 5,112,857, U.S. Pat. No. 5,102,911, U.S. Pat. No. 5,098,931, U.S. Pat. No. 5,081,136, U.S. Pat. No. 5,025,000, U.S. Pat. No. 5,021,453, U.S. Pat. No. 5,017,716, U.S. Pat. No. 5,001,144, U.S. Pat. No. 5,001,128, U.S. Pat. No. 4,997,837, U.S. Pat. No. 4,996,234, U.S. Pat. No. 4,994,494, U.S. Pat. No. 4,992,429, U.S. Pat. No. 4,970,231, U.S. Pat. No. 4,968,693, U.S. Pat. No. 4,963,538, U.S. Pat. No. 4,957,940, U.S. Pat. No. 4,950,675, U.S. Pat. No. 4,946,864, U.S. Pat. No. 4,946,860, U.S. Pat. No. 4,940,800, U.S. Pat. No. 4,940,727, U.S. Pat. No. 4,939,143, U.S. Pat. No. 4,929,620, U.S. Pat. No. 4,923,861, U.S. Pat. No. 4,906,657, U.S. Pat. No. 4,906,624 and U.S. Pat. No. 4,897,402.

Examples of statins already approved for use in humans include atorvastatin, cerivastatin, fluvastatin, pravastatin, simvastatin and rosuvastatin. The reader is referred to the following references for further information on HMG-CoA reductase inhibitors: Drugs and Therapy Perspectives (May 12, 1997), 9: 1-6; Chong (1997) Pharmacotherapy 17:1157-1177; Kellick (1997) Formulary 32: 352; Kathawala (1991) Medicinal Research Reviews, 11: 121-146; Jahng (1995) Drugs of the Future 20: 387-404, and Current Opinion in Lipidology, (1997), 8, 362-368. Another statin drug of note is compound 3a (S-4522) in Watanabe (1997) Bioorganic and Medicinal Chemistry 5: 437-444.

Non-statin anti-lipemic agents include but are not limited to fibric acid derivatives (fibrates), bile acid sequestrants or resins, nicotinic acid agents, cholesterol absorption inhibitors, acyl-coenzyme A: cholesterol acyl transferase (ACAT) inhibitors, cholesteryl ester transfer protein (CETP) inhibitors, LDL receptor antagonists, farnesoid X receptor (FXR) antagonists, sterol regulatory binding protein cleavage activating protein (SCAP) activators, microsomal triglyceride transfer protein (MTP) inhibitors, squalene synthase inhibitors and peroxisome proliferation activated receptor (PPAR) agonists.

Examples of fibric acid derivatives include but are not limited to gemfibrozil (Lopid), fenofibrate (Tricor), clofibrate (Atromid) and bezafibrate.

Examples of bile acid sequestrants or resins include but are not limited to colesevelam (WelChol), cholestyramine (Questran or Prevalite) and colestipol (Colestid), DMD-504, GT-102279, HBS-107 and S-8921.

Examples of nicotinic acid agents include but are not limited to niacin and probucol.

Examples of cholesterol absorption inhibitors include but are not limited to ezetimibe (Zetia).

Examples of ACAT inhibitors include but are not limited to Avasimibe, CI-976 (Parke Davis), CP-113818 (Pfizer), PD-138142-15 (Parke Davis), FF1394, and numerous others described in U.S. Pat. Nos. 6,204,278, 6,165,984, 6,127,403, 6,063,806, 6,040,339, 5,880,147, 5,621,010, 5,597,835, 5,576,335, 5,321,031, 5,238,935, 5,180,717, 5,149,709, and 5,124,337.

Examples of CETP inhibitors include but are not limited to Torcetrapib, CP-529414, CETi-1, JTT-705, and numerous others described in U.S. Pat. Nos. 6,727,277, 6,723,753, 6,723,752, 6,710,089, 6,699,898, 6,696,472, 6,696,435, 6,683,099, 6,677,382, 6,677,380, 6,677,379, 6,677,375, 6,677,353, 6,677,341, 6,605,624, 6,586,448, 6,521,607, 6,482,862, 6,479,552, 6,476,075, 6,476,057, 6,462,092, 6,458,852, 6,458,851, 6,458,850, 6,458,849, 6,458,803, 6,455,519, 6,451,830, 6,451,823, 6,448,295, 5,512,548.

One example of an FXR antagonist is Guggulsterone. One example of a SCAP activator is GW532 (GlaxoSmithKline).

Examples of MTP inhibitors include but are not limited to Implitapide and R-103757.

Examples of squalene synthase inhibitors include but are not limited to zaragozic acids.

Examples of PPAR agonists include but are not limited to GW-409544, GW-501516, and LY-510929.

Anti-inflammatory agents include but are not limited to Alclofenac, Alclometasone Dipropionate, Algestone Acetonide, Alpha Amylase, Amcinafal, Amcinafide, Amfenac Sodium, Amiprilose Hydrochloride, Anakinra, Anirolac, Anitrazafen, Apazone, Balsalazide Disodium, Bendazac, Benoxaprofen, Benzydamine Hydrochloride, Bromelains, Broperamole, Budesonide, Carprofen, Cicloprofen, Cintazone, Cliprofen, Clobetasol Propionate, Clobetasone Butyrate, Clopirac, Cloticasone Propionate, Cormethasone Acetate, Cortodoxone, Deflazacort, Desonide, Desoximetasone, Dexamethasone Dipropionate, Diclofenac Potassium, Diclofenac Sodium, Diflorasone Diacetate, Diflumidone Sodium, Diflunisal, Difluprednate, Diftalone, Dimethyl Sulfoxide, Drocinonide, Endrysone, Enlimomab, Enolicam Sodium, Epirizole, Etodolac, Etofenamate, Felbinac, Fenamole, Fenbufen, Fenclofenac, Fenclorac, Fendosal, Fenpipalone, Fentiazac, Flazalone, Fluazacort, Flufenamic Acid, Flumizole, Flunisolide Acetate, Flunixin, Flunixin Meglumine, Fluocortin Butyl, Fluorometholone Acetate, Fluquazone, Flurbiprofen, Fluretofen, Fluticasone Propionate, Furaprofen, Furobufen, Halcinonide, Halobetasol Propionate, Halopredone Acetate, Ibufenac, Ibuprofen, Ibuprofen Aluminum, Ibuprofen Piconol, Ilonidap, Indomethacin, Indomethacin Sodium, Indoprofen, Indoxole, Intrazole, Isoflupredone Acetate, Isoxepac, Isoxicam, Ketoprofen, Lofemizole Hydrochloride, Lomoxicam, Loteprednol Etabonate, Meclofenamate Sodium, Meclofenamic Acid, Meclorisone Dibutyrate, Mefenamic Acid, Mesalamine, Meseclazone, Methylprednisolone Suleptanate, Morniflumate, Nabumetone, Naproxen, Naproxen Sodium, Naproxol, Nimazone, Olsalazine Sodium, Orgotein, Orpanoxin, Oxaprozin, Oxyphenbutazone, Paranyline Hydrochloride, Pentosan Polysulfate Sodium, Phenbutazone Sodium Glycerate, Pirfenidone, Piroxicam, Piroxicam Cinnamate, Piroxicam Olamine, Pirprofen, Prednazate, Prifelone, Prodolic Acid, Proquazone, Proxazole, Proxazole Citrate, Rimexolone, Romazarit, Salcolex, Salnacedin, Salsalate, Salycilates, Sanguinarium Chloride, Seclazone, Sermetacin, Sudoxicam, Sulindac, Suprofen, Talmetacin, Talniflumate, Talosalate, Tebufelone, Tenidap, Tenidap Sodium, Tenoxicam, Tesicam, Tesimide, Tetrydamine, Tiopinac, Tixocortol Pivalate, Tolmetin, Tolmetin Sodium, Triclonide, Triflumidate, Zidometacin, Glucocorticoids and Zomepirac Sodium.

Anti-thrombotic agents and/or fibrinolytic agents include but are not limited to tissue plasminogen activator (e.g., Activase, Alteplase) (catalyzes the conversion of inactive plasminogen to plasmin). This may occur via interactions of prekallikrein, kininogens, Factors XII, XIIIa, plasminogen proactivator, and tissue plasminogen activator TPA) Streptokinase, Urokinase, Anisoylated Plasminogen-Streptokinase Activator Complex, Pro-Urokinase, (Pro-UK), rTPA (alteplase or activase; r denotes recombinant), rPro-UK, Abbokinase, Eminase, Sreptase Anagrelide Hydrochloride, Bivalirudin, Dalteparin Sodium, Danaparoid Sodium, Dazoxiben Hydrochloride, Efegatran Sulfate, Enoxaparin Sodium, Ifetroban, Ifetroban Sodium, Tinzaparin Sodium, retaplase, Trifenagrel, Warfarin, Dextrans, aminocaproic acid (Amicar) and tranexamic acid (Amstat).

Anti-platelet agents include but are not limited to Clopridogrel, Sulfinpyrazone, Aspirin, Dipyridamole, Clofibrate, Pyridinol Carbamate, PGE, Glucagon, Antiserotonin drugs, Caffeine, Theophyllin Pentoxifyllin, Ticlopidine and Anagrelide.

Direct thrombin inhibitors include but are not limited to hirudin, hirugen, hirulog, agatroban, PPACK and thrombin aptamers.

Glycoprotein IIb/IIIa receptor Inhibitors are both antibodies and non-antibodies, and include but are not limited to ReoPro (abcixamab), lamifiban and tirofiban.

Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies as well as other such antibodies.

Examples of alpha-adrenergic blockers include but are not limited to: doxazocin, prazocin, tamsulosin, and tarazosin.

Beta-adrenergic receptor blocking agents are a class of drugs that antagonize the cardiovascular effects of catecholamines in angina pectoris, hypertension and cardiac arrhythmias. Beta-adrenergic receptor blockers include, but are not limited to, atenolol, acebutolol, alprenolol, befunolol, betaxolol, bunitrolol, carteolol, celiprolol, hydroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide. The above-identified compounds can be used as isomeric mixtures, or in their respective levorotating or dextrorotating form.

Cyclooxygenase-2 (COX-2) is a recently identified new form of a cyclooxygenase. Cyclooxygenase is an enzyme complex present in most tissues that produces various prostaglandins and thromboxanes from arachidonic acid. Nonsteroidal, antiinflammatory drugs exert most of their antiinflammatory, analgesic and antipyretic activity and inhibit hormone-induced uterine contractions and certain types of cancer growth through inhibition of the cyclooxygenase (also known as prostaglandin G/H synthase and/or prostaglandin-endoperoxide synthase). Initially, only one form of cyclooxygenase was known, the "constitutive enzyme" or cyclooxygenase-1 (COX-1). It was originally identified in bovine seminal vesicles.

Cyclooxygenase-2 (COX-2) has been cloned, sequenced and characterized initially from chicken, murine and human sources (See, e.g., U.S. Pat. No. 5,543,297, issued Aug. 6, 1996 to Cromlish, et al., and assigned to Merck Frosst Canada, Inc., Kirkland, Calif., entitled: "Human cyclooxygenase-2 cDNA and assays for evaluating cyclooxygenase-2 activity"). This enzyme is distinct from the COX-1. COX-2, is rapidly and readily inducible by a number of agents including mitogens, endotoxin, hormones, cytokines and growth factors. As prostaglandins have both physiological and pathological roles, it is believed that the constitutive enzyme, COX-1, is responsible, in large part, for endogenous basal release of prostaglandins and hence is important in their physiological functions such as the maintenance of gastrointestinal integrity and renal blood flow. By contrast, it is believed that the inducible form, COX-2, is mainly responsible for the pathological effects of prostaglandins where rapid induction of the enzyme would occur in response to such agents as inflammatory agents, hormones, growth factors, and cytokines. Therefore, it is believed that a selective inhibitor of COX-2 has similar antiinflammatory, antipyretic and analgesic properties to a conventional non-steroidal antiinflammatory drug, and in addition inhibits hormone-induced uterine contractions and also has potential anti-cancer effects, but with reduced side effects. In particular, such COX-2 inhibitors are believed to have a reduced potential for gastrointestinal toxicity, a reduced potential for renal side effects, a reduced effect on bleeding times and possibly a decreased potential to induce asthma attacks in aspirin-sensitive asthmatic subjects, and are therefore useful according to the present invention.

A number of selective COX-2 inhibitors are known in the art. These include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indol-3-yl butanoic acid derivatives as cyclooxygenase inhibitors"; U.S. Pat. No. 5,677,318 Diphenyl-1,2-3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

An angiotensin system inhibitor is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, a pseudoglobulin in blood plasma, to produce the decapeptide angiotensin I. Angiotensin I is converted by angiotensin converting enzyme (ACE) to angiotensin II (angiotensin-[1-8] octapeptide). The latter is an active pressor substance which has been implicated as a causative agent in several forms of hypertension in various mammalian species, e.g., humans.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists. In a preferred embodiment of the invention, the renin-angiotensin system inhibitors are renin inhibitors, ACE inhibitors, and angiotensin II antagonists.

Angiotensin II antagonists are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid. Stability can be enhanced by other replacements that slow degeneration in vivo. Examples of angiotensin II receptor antagonists include but are not limited to: Candesartan (Alacand), Irbesartan (Avapro), Losartan (Cozaar), Telmisartan (Micardis), and Valsartan (Diovan). Other examples of angiotensin II antagonists include: peptidic compounds (e.g., saralasin, [(Sar$^1$)(Val$^5$)(Ala$^8$)]angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., *J. Pharmacol. Exp. Ther.* 247(1), 1-7 (1988)); 4, 5, 6, 7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(–1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl)methyl]1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G.D. Searle and Company).

Angiotensin converting enzyme (ACE), is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410, 520), phosphinylalkanoyl prolines such as fosinopril (U.S. Pat. No. 4,337,201) and trandolopril.

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof (U.S. Pat. Nos. 5,104,869 and 5,095, 119); diol sulfonamides and sulfinyls (U.S. Pat. No. 5,098, 924); modified peptides (U.S. Pat. No. 5,095,006); peptidyl beta-aminoacyl aminodiol carbamates (U.S. Pat. No. 5,089, 471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063, 208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Calcium channel blockers are a chemically diverse class of compounds having important therapeutic value in the control of a variety of diseases including several cardiovascular disorders, such as hypertension, angina, and cardiac arrhythmias (Fleckenstein, *Cir. Res.* v. 52, (suppl. 1), p. 13-16 (1983); Fleckenstein, *Experimental Facts and Therapeutic Prospects*, John Wiley, New York (1983); McCall, D., *Curr Pract Cardiol*, v. 10, p. 1-11 (1985)). Calcium channel blockers are a heterogenous group of drugs that prevent or slow the entry of calcium into cells by regulating cellular calcium channels. (Remington, *The Science and Practice of Pharmacy*, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, aminone, amlodipine, bencyclane, felodipine, fendiline, flunarizine, isradipine, nicardipine, nimodipine, perhexylene, gallopamil, tiapamil and tiapamil analogues (such as 1993RO-11-2933), phenyloin, barbiturates, and the peptides dynorphin, omega-conotoxin, and omega-agatoxin, and the like and/or pharmaceutically acceptable salts thereof.

Diuretics include but are not limited to: carbonic anhydrase inhibitors, loop diuretics, potassium-sparing diuretics, thiazides and related diuretics.

Vasodilators include but are not limited to coronary vasodilators and peripheral vasodilators.

Vasopressors are agents that produce vasoconstriction and/or a rise in blood pressure. Vasopressors include but are not limited to: dopamine, ephedrine, epinephrine, Methoxamine HCl (Vasoxyl), phenylephrine, phenylephrine HCl (Neo-Synephrine), and Metaraminol.

Thiazolidinediones include but are not limited to: rosiglitazone (Avandia), pioglitazone (Actos), troglitazone (Rezulin). Combination therapies of thiazolidinediones and other agents such as rosiglitazone and metformin (Avandamet) are encompassed by this invention.

An example of a cannabinoid-1 receptor blocker is rimonabant.

Immunosuppressive agents include but are not limited to steroids, calcineurine inhibitors, monoclonal antibodies and polyclonal antibodies. The steroid can be a corticosteroid. Examples of corticosteroids include but are not limited to prednisone and methylprednisone. Examples of calcineurine inhibitors include but are not limited to cyclosporine and tacrolimus. Examples of monoclonal antibodies include but are not limited to anti-CD3 antibody (Muromonab-CD3; Orthoclone OKT3®) and anti-IL-2R alpha chain (p55). Examples of polyclonal antibodies include but are not limited to anti-thymocyte globulin-equine (Atgam®) and anti-thymocyte globulin-rabbit (RATG thymoglobuline). Other examples of immunosuppressive agents include sulfasalazine, FK-506, methoxsalen, thalidomide, mycophenolate mofetil (MMF), azathioprine and sirolimus.

The methods provided can also include the use of other therapies, such as diet and/or exercise. In some embodiments, these therapies are in addition to therapeutic treatment with IL-33 and/or a soluble ST2 inhibiting agent.

As mentioned previously, methods of evaluating risk, diagnosis, determining the progression of a cardiac disease or disorder or evaluating therapeutic efficacy are also provided.

A method for characterizing a subject's risk profile for developing a cardiac disease or disorder is, therefore, provided. As used herein, a subject's "risk profile" is a characterization of the likelihood that the subject will develop a cardiac disease or disorder. Based on this likelihood, a medical professional can then also determine whether or not treatment is needed. The assessment of a subject's risk profile can occur once or can occur more than once. Therefore, the methods provided herein can be used to monitor a subject's risk for developing a cardiac disease or disorder over time (e.g., over 2, 3, 4, 5, 6, 7, 8, 9, 10 or more time points). A subject's risk profile, therefore, can be determined on a routine basis (e.g., 1, 2, 3 or 4 times a year, every year or every 2, 3, 4, 5, 6, 7, 8, 9 or 10 years, etc.). The method for assessing risk can include the steps of determining the level of IL-33 in a sample obtained from the subject, comparing the level of IL-33 to a predetermined value, and characterizing the subject's risk of developing the cardiac disease or disorder based upon the level of IL-33 in comparison to the predetermined value. In some embodiments, a determination that the level of IL-33 is at, below or above a predetermined value is indicative of the subject's risk. In some embodiments, when a level of IL-33 is determined to be at or above the predetermined value it is indicative that the subject is at an elevated risk of developing the cardiac disease or disorder. In other embodiments, a level of IL-33 below the predetermined value is indicative that the subject is not at an elevated risk of developing the cardiac disease or disorder. In still another embodiment, the assessment is based on the comparison of the level of IL-33 to a predetermined value as well as a comparison of the level of at least one other marker of a cardiac disease or disorder to a predetermined value. Such markers are described in more detail below. In some embodiments, the subject for which a risk profile is determined is an apparently healthy subject.

Also provided is a method for diagnosing a cardiac disease or disorder. As used herein, "diagnosing" refers to the determination of the presence or absence of a cardiac disease or disorder in a subject or the determination that further testing is required in order to arrive at a final diagnosis. Such a method can include the steps of determining the level of IL-33 in a sample obtained from a subject, comparing the level of IL-33 to a predetermined value, and diagnosing the cardiac disease or disorder based upon the comparison. In some embodiments, a level of IL-33 at, below or above a predetermined value is indicative of whether or not the subject has the cardiac disease or disorder. In other embodiments, a level of IL-33 at or above a predetermined value is indicative that the subject has the cardiac disease or disorder. In other embodiments, a level of IL-33 below the predetermined value is indicative that the subject does not have the cardiac disease or disorder. The methods of diagnosis can also include determining the level of another marker of a cardiac disease or disorder and comparing the level of the other marker with a predetermined value. In some embodiments, a final diagnosis is reached through the assessment of two or more markers.

Also provided is a method for determining the prognosis of a cardiac disease or disorder. Prognosis refers to the onset, progression or regression of a cardiac disease or disorder. Prognosis includes determining the outcome of a cardiac disease or disorder. A prognostic method can include the steps of determining the level of IL-33 in a sample obtained from a subject, and comparing the level of IL-33 to a predetermined value. A level of IL-33 at, below or above a predetermined value can be indicative of the prognosis. In some embodiments, at level of IL-33 at or above a predetermined value is indicative of the prognosis of the cardiac disease or disorder in the subject. In one embodiment, the prognosis is that a positive outcome is expected. As used herein, a "positive outcome" refers to a reduction in one or more symptoms of the cardiac disease or disorder and/or an improvement in survival from the cardiac disease or disorder. One or more of the steps of the method can be repeated so that a subject's prognosis can be monitored over time. A method of determining prognosis can, therefore, be conducted on a routine basis (e.g., weekly, monthly, bimonthly or yearly). In some embodiments, a method of prognosis can be conducted 1, 2, 3, 4 or 5 times a year. In other embodiments, a method of prognosis can be conducted every 2, 3, 4 or 5 years. In some embodiments, in order to determine the prognosis, the level of another marker is also compared to a predetermined value. A final prognosis can, in some embodiments, be reached with the assessment of two or more markers.

Methods for determining a stage of a cardiovascular disease or disorder is also provided. The methods can, in some embodiments, involve determining the level of IL-33 in a sample from a subject as a determination of a stage of a cardiovascular disease or disorder in the subject. The result of the comparison being an indication of a stage of a cardiovascular disease or disorder.

The invention also embraces methods for evaluating the likelihood that a subject will benefit from treatment with a therapeutic agent or some combination of therapeutic agents as provided herein. In some embodiments, the agent is IL-33, a soluble ST2 inhibiting agent, an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, an angiotensin system inhibitor or an immunosuppressive agent. The method can, in some embodiments, involve determining the expression level of a marker (e.g., IL-33) in the subject, and comparing the level of the marker to a predetermined value.

The level of the marker in comparison to the predetermined value is indicative of whether the subject will benefit from treatment with said agent. In certain embodiments, the predetermined value is a plurality of predetermined marker level ranges and said comparing step comprises determining in which of said predetermined marker level ranges said subjects level falls. This method has important implications for patient treatment and also for clinical development of new therapeutics. Physicians select therapeutic regimens for patient treatment based upon the expected net benefit to the patient. The net benefit is derived from the risk to benefit ratio. The present invention permits selection of subjects who are more likely to benefit by intervention, thereby aiding the physician in selecting a therapeutic regimen. This might include using drugs with a higher risk profile where the likelihood of expected benefit has increased. Likewise, clinical investigators desire to select for clinical trials a population with a high likelihood of obtaining a net benefit. The present invention can help clinical investigators select such subjects. It is expected that clinical investigators now will use the present invention for determining entry criteria for clinical trials.

Measurement of IL-33 alone or with other markers can be important in choosing therapy and determining the efficacy of therapy. The invention provides methods for determining whether a human subject will benefit from continued therapy or would benefit from a change in therapy. The benefit is typically, but not necessarily so, a reduction in the rate of occurrence of cardiovascular events. One example of clinical usefulness includes identifying subjects who are less likely or more likely to respond to a therapy. The methods of the invention are also useful in predicting or determining that a human subject would benefit from continued therapy or would benefit from a change in therapy. Another example of clinical usefulness includes aiding clinical investigators in the selection for clinical trials of human subjects with a high likelihood of obtaining a net benefit. It is expected that clinical investigators now will use the present invention for determining entry criteria for clinical trials.

A subject who would benefit from continued therapy is a subject whose on therapy level of IL-33 and/or a non-IL-33 marker reaches a certain predetermined value. In some embodiments, a subject would benefit from continued therapy provided that his/her on therapy IL-33 level reaches a certain predetermined value, whereby the IL-33 level is equal to or greater than the predetermined value. In other embodiments, a subject would benefit from continued therapy if his/her on therapy level is equal to or greater than a predetermined value for IL-33 and his/her on therapy level for a non-IL-33 marker, such as a marker of systemic inflammation or soluble ST2, is less than another predetermined value. As another example, a subject who would benefit from a change in therapy is a human subject whose on therapy level of IL-33 did not reach a certain predetermined value.

As used herein, a "change in therapy" refers to an increase or decrease in the dose of the existing therapy, a switch from one therapy to another therapy, an addition of another therapy to the existing therapy, or a combination thereof. A switch from one therapy to another may involve a switch to a therapy with a high risk profile but where the likelihood of expected benefit is increased. For example, a human who would benefit from a change in therapy, in some embodiments, is a human subject whose IL-33 level did not reach a certain predetermined value. Therefore, a human who would benefit from a change in therapy by increasing the dose of the existing therapy is a human subject who, for example, was on the therapy but was not receiving the maximum tolerated dose or the maximum allowed dose of the therapy and whose IL-33 level did not reach a certain predetermined value. A subject who would benefit from an increase in dose of an existing therapy is also one whose IL-33 level did not reach a certain predetermined value and whose soluble ST2 level did not fall below a predetermined value. In such instances, the dose of the existing therapy is increased until the level of IL-33 reaches a certain predetermined value. In some instances, the dose of the existing therapy is increased from the existing dose to a higher dose that is not the maximum tolerated dose nor the maximum allowed dose of the therapy. In other instances, the dose is increased to the maximum tolerated or to the maximum allowed dose of the therapy. A subject who would benefit from a change in therapy by decreasing the dose of the existing therapy is, for example, a subject whose on therapy level of IL-33 and/or another marker reaches or can reach a certain predetermined value with a lower dose of the therapy or a subject whose on therapy level of IL-33 and/or another marker reaches or can reach a certain predetermined value with a lower dose of the therapy and whose on therapy level of soluble ST2 falls below or can fall below a predetermined value with a lower dose of the therapy.

A subject who would benefit from a switch from one therapy to another therapy is, for example, a subject who was on the maximum tolerated dose or the maximum allowed dose of the therapy and whose level of IL-33 did not reach a certain predetermined value and/or whose level of soluble ST2 is greater than a predetermined value. The subject can also be one with a level of IL-33 that is less than a predetermined value and a level of another marker (e.g., soluble ST2) that is greater than a predetermined value. Another example is a subject not on the maximum tolerated or the maximum allowed dose of the therapy but is determined by a health care practitioner to more likely benefit from another therapy. Such determinations are based, for example, on the development in the subject of unwanted side effects on the initial therapy or a lack of response to the initial therapy.

A subject who would benefit from a change in therapy by the addition of another therapy to the existing therapy is, for example, a subject who was on a therapy but whose level of a marker or markers did not reach certain predetermined values. In such instances, another therapy is added to the existing therapy. The therapy that is added to the existing therapy can have a different mechanism of action. In some instances, a combination of the aforementioned changes in therapy may be used.

The invention also provides methods for determining the efficacy of a therapy. The efficacy is typically the efficacy of the therapy in raising the level of IL-33 alone or in combination with lowering the level of, for example, soluble ST2 or a marker of systemic inflammation (e.g., lowering of CRP). This is sometimes also referred to as a positive response or a favorable response. Efficacy can be determined by a blood test(s) to determine whether IL-33 and/or other marker levels are raised or lowered or some combination thereof, as a result of therapy. In some embodiments, efficacy determination is based on the efficacy of a therapy in raising IL-33 levels and lowering both CRP and lipid levels (e.g., cholesterol or LDLC). Tests and methods for measuring CRP and lipid levels in blood, especially serum samples, and for interpreting results of such tests are widely used in clinical practice today. Additionally, tests for measuring other markers, such as IL-33 and/or soluble ST2, would be similar.

The invention also provides methods for deciding on the course of a therapy in a subject undergoing therapy or about to undergo therapy to reduce the risk of a cardiac disease or disorder. Such a course of therapy is decided on the basis of the level of IL-33 alone or in combination with another marker, such as soluble ST2 or a marker of systemic inflammation. Therapies for reducing the risk of a cardiac disease or disorder are described above. In some embodiments, the subject already has had a cardiovascular event, such as, for example, a myocardial infarct or has had an angioplasty. A subject who has had a primary (first) cardiovascular event is at an elevated risk of a secondary (second) cardiovascular event due to the primary cardiovascular event. In some embodiments, the subject is at an elevated risk of a cardiovascular event because the human subject has one or more risk factors to have a cardiovascular event. Examples of risk factors to have a cardiovascular event are described above. In some embodiments, the human subject who is at risk of a cardiovascular event may be an apparently healthy human subject. An apparently healthy human subject is described above.

These methods have important implications for patient treatment and also for the clinical development of new therapies. It is also expected that clinical investigators now will use the present methods for determining entry criteria for human subjects in clinical trials. Health care practitioners select therapeutic regimens for treatment based upon the expected net benefit to the human subject. The net benefit is derived from the risk to benefit ratio. The present invention permits the determination of whether a human subject will benefit from continued therapy or would benefit from a change in therapy, thereby aiding the physician in selecting a therapy.

Predetermined values can take a variety of forms. It can be single cut-off value, such as a median or mean. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quartiles, the lowest quartile being individuals with the lowest risk and the highest quartile being individuals with the highest risk, or into tertiles the lowest tertile being individuals with the lowest risk and the highest tertile being individuals with the highest risk. An important predetermined value for a marker (IL-33 or another marker) is a value that is the average for a healthy human subject population (i.e., human subjects who have no signs and symptoms of disease). The predetermined value will depend, of course, on the characteristics of the patient population in which the individual lies. In characterizing risk, numerous predetermined values can be established.

The predetermined value can depend upon the particular population of subjects selected. For example, an apparently healthy population will have a different 'normal' range than will a population of subjects which have or have had a cardiac disease or disorder. Accordingly, the predetermined values selected may take into account the category in which a subject falls. In some embodiments, the category of subjects are those that have been treated for a cardiac disease or disorder. The predetermined value, in some of these embodiments, represents a level of a marker (e.g., IL-33) at which or above which a therapeutic benefit has been observed in treated subjects. In other embodiments, the predetermined value represents a level of a marker at which or below which a therapeutic benefit has been observed in treated subjects. In still other embodiments, the category of subjects are those that are healthy. In some of these embodiments, the marker (e.g., IL-33) level of the healthy subjects represents a level from which if there is significant variation the presence of a cardiac disease or disorder or risk thereof is indicated. In still other embodiments, the predetermined value represents a level of marker (e.g., soluble ST2) at which or above which treatment with a soluble ST2 inhibiting agent would be beneficial. In yet other embodiments, the predetermined value represents a level of a marker at which or below which treatment would be beneficial. Appropriate ranges and categories can be selected with no more than routine experimentation by those of ordinary skill in the art.

The expression level can be determined by contacting a sample obtained from a subject with an agent that specifically binds to a nucleic acid molecule encoding a protein or the protein itself and determining the interaction between the binding agent and the nucleic acid or protein. In the case where the molecule detected is a nucleic acid molecule, such determinations can be carried out via any standard nucleic acid determination assay, including the polymerase chain reaction, or assaying with labeled hybridization probes. In the case where the molecule is a protein, such determination can be carried out via any standard immunological assay using, for example, antibodies or antigen-binding fragments thereof. Other methods of specifically and quantitatively measuring proteins include, but are not limited to: mass spectroscopy-based methods such as surface enhanced laser desorption ionization (SELDI; e.g., Ciphergen ProteinChip System), non-mass spectroscopy-based methods, and immunohistochemistry-based methods such as 2-dimensional gel electrophoresis.

The level of a marker (e.g., IL-33) can be determined in a body fluid, such as, for example, blood, plasma, serum, lymph, saliva, urine and the like. In some embodiments, the level of the marker can be determined in a body tissue sample from a subject. In one embodiment, the body tissue sample is a cardiac tissue sample. The level can be determined by ELISA, or immunoassays or other conventional techniques for determining the presence of the marker. Conventional methods include sending a sample(s) of a patient's body fluid to a commercial laboratory for measurement.

"Upregulation," as used herein, refers to increased expression of a gene and/or its encoded polypeptide. "Increased expression" refers to increasing (i.e., to a detectable extent) replication, transcription, and/or translation of a nucleic acid encoding a polypeptide. Conversely, "downregulation," or "decreased expression", as used herein, refers to decreased expression of a gene and/or its encoded polypeptide. The upregulation or downregulation of gene expression can be directly determined by detecting an increase or decrease, respectively, in the level of mRNA for the gene, or the level of protein expression of the gene-encoded polypeptide, using any suitable means known to the art, such as nucleic acid hybridization or antibody detection methods, respectively, and in comparison to controls.

The hybridization is, preferably, performed under stringent conditions and, even more preferably, under highly stringent conditions. The term "stringent conditions," as used herein, refers to parameters with which the art is familiar. With nucleic acids, hybridization conditions are said to be stringent typically under conditions of low ionic strength and a temperature just below the melting temperature ($T_m$) of the DNA hybrid complex (typically, about 3° C. below the $T_m$ of the hybrid). Higher stringency makes for a more specific correlation between the probe sequence and the target. Stringent conditions used in the hybridization of nucleic acids are well known in the art and may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. An example of "high stringency conditions" is hybridization at 65° C. in 6×SSC. Another example of high stringency conditions is hybridization at 65° C. in hybridization buffer that consists of 3.5×SSC, 0.02% Ficoll, 0.02% polyvinyl pyrolidone, 0.02% Bovine Serum Albumin, 2.5 mM $NaH_2PO_4$ [pH7], 0.5% SDS, 2 mM EDTA. (SSC is 0.015M sodium chloride/0.15M sodium citrate, pH7; SDS is sodium dodecyl sulphate; and EDTA is ethylenediaminetetracetic acid). After hybridization, the membrane upon which the DNA is transferred is washed at 2×SSC at room temperature and then at 0.1×SSC/0.1×SDS at temperatures up to 68° C. In a further example, an alternative to the use of an aqueous hybridization solution is the use of a formamide hybridization solution. Stringent hybridization conditions can thus be achieved using, for example, a 50% formamide solution and 42° C. There are other conditions, reagents, and so forth which can be used, and would result in a similar degree of stringency. The skilled artisan will be familiar with such conditions, and thus they are not given here.

According to the invention, expression of a nucleic acid encoding a marker can be determined using different methodologies. Such methodologies include Southern and Northern blot assays using nucleic acid probes and amplification assays such as those employing PCR. As known to those skilled in the art, large probes such as 200, 250, 300 or more nucleotides are preferred for certain uses such as Southern and Northern blots, while smaller nucleic acids will be preferred for other uses such as PCR. Nucleic acids encoding a marker protein or a portion thereof also can be used to produce fusion proteins for generating antibodies or for generating immunoassay components. Likewise, such nucleic acids can be employed to produce nonfused fragments of polypeptides, useful, for example, in the preparation of antibodies, immunoassays or therapeutic applications.

As will be recognized by those skilled in the art, the size of the nucleic acid for use in the nucleic acid detection assays is between 8, 9, 10, 11 or 12 and 100 nucleotides long (e.g., 12, 13, 14, 15, 16, 17, 18, 19, 20, 21, 22, 23, 24, 25, 26, 27, 28, 29, 30, 31, 32, 35, 40, 45, 50, 55, 60, 65, 70, 75, 80, 85, 90, 95 or 100 bases) or more, up to the entire length of the marker (e.g., IL-33) mRNA sequence. As mentioned above, this disclosure intends to embrace each and every fragment of the sequence, beginning at the first nucleotide, the second nucleotide and so on, up to 8 nucleotides short of the end, and ending anywhere from nucleotide number 8, 9, 10 and so on for each sequence, up to the very last nucleotide. In some embodiments, it is preferable for the fragment to be unique to the nucleic acid encoding the marker (e.g., IL-33).

A "unique fragment", as used herein, with respect to a nucleic acid is one that is a "signature" for the larger nucleic acid. For example, the unique fragment is long enough to assure that its precise sequence is not found in molecules within the human genome outside of the sequence for which detection is desired. Those of ordinary sill in the art may apply no more than routine procedures to determine if a fragment is unique within the human genome. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

As mentioned above, expression of a protein can be determined with, for example, antibodies or antigen-binding fragments thereof. Antibodies include polyclonal and monoclonal antibodies, prepared according to conventional methodology. Protein expression can also be determined with binding agents derived from sources other than antibody technology. For example, such binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

The step of determining can be accomplished by contacting the sample with a detectable agent, such as an isolated nucleic acid molecule that selectively hybridizes under stringent conditions to a nucleic acid molecule that encodes a marker (e.g., IL-33), a polypeptide, such as an antibody or antigen-binding fragment thereof, that selectively binds the marker or a fragment thereof, or a polypeptide, such as an antibody or antigen-binding fragment thereof, that selectively binds an endogenously produced antibody directed against the marker. The methods can also comprise determining expression over a period of time.

Detectable labels include fluorescent labels, chemiluminescent labels, radioactive labels and enzymes.

In some embodiments, the methods can further include the use of one or more additional tests. In some embodiments, the one or more additional tests includes the measurement of a non-IL-33 marker of cardiac disease or disorder in a subject. Such markers include, for example, cholesterol, LDLC, soluble ST2 and markers of systemic inflammation. When a level of a non-IL-33 marker in a subject is obtained, the level, in some embodiments, can also be compared to a predetermined value.

Markers of systemic inflammation are well-known to those of ordinary skill in the art. It is preferred that the markers of systemic inflammation be selected from the group consisting of CRP, cytokines and cellular adhesion molecules. Cytokines are well-known to those of ordinary skill in the art and include human interleukin 1, 2, 3, 4, 5, 6, 7, 8, 9, 10, 11, 12, 13, 14, 15, 16 and 17. Cellular adhesion molecules are well-known to those of ordinary skill in the art and include integrins, soluble intercellular adhesion molecule (sICAM-1), ICAM-3, BL-CAM, LFA-2, VCAM-1, NCAM, PECAM, fibrinogen, serum amyloid A (SAA), lipoprotein associated phospholipase A2 (LpPlA2), sCD40 ligand, myeloperoxidase, interleukin-6 (IL-6) and interleukin-8 (IL-8). One preferred adhesion molecule is sICAM-1.

An important predetermined value of a marker of systemic inflammation is a value that is the average for a healthy human subject population (i.e., human subjects who have no signs and symptoms of disease). The predetermined value will depend, of course, on the particular marker selected and even upon the characteristics of the patient population in which the individual lies. In characterizing risk, numerous predetermined values can be established.

Presently there are commercial sources which produce reagents for assays for CRP. These include, but are not limited to, Dade-Behring (Deerfield, Ill.), Abbott Pharmaceuticals (Abbott Park, Ill.), CalBiochem (San Diego, Calif.) and Behringwerke (Marburg, Germany). Commercial sources for inflammatory cytokine and cellular adhesion molecule measurements, include, but are not limited to, R&D Systems (Minneapolis, Minn.), Genzyme (Cambridge, Mass.) and Immunotech (Westbrook, Me.).

Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies.

A lipid test (e.g. cholesterol) is often performed to evaluate risks for heart disease. As is known in the art, cholesterol is an important normal body constituent, used in the structure of cell membranes, synthesis of bile acids, and synthesis of steroid hormones. Since cholesterol is water insoluble, most serum cholesterol is carried by lipoproteins (chylomicrons, VLDLC, LDLC, and HDLC). Excess cholesterol in the blood has been correlated with cardiovascular events. LDL is sometimes referred to as "bad" cholesterol, because elevated levels of LDL correlate most directly with cardiovascular events such as coronary heart disease. HDL is sometimes referred to as "good" cholesterol since high levels of HDL are correlated with a reduced risk for cardiovascular events such as coronary heart disease. The term cholesterol means "total" cholesterol i.e. VLDLC+LDLC+HDLC.

Preferably, CRP and cholesterol levels are measured after a patient has fasted. The cholesterol measurement is typically reported in milligrams per deciliter (mg/dL). Typically, the higher the total cholesterol, the more at risk a subject is for a cardiovascular event. A value of total cholesterol of less than 200 mg/dL is a "desirable" level and places the human subject in a group at less risk for a cardiovascular event(s). Levels over 240 mg/dL, for example, may put a human subject at almost twice the risk of a cardiovascular event, such as coronary heart disease, as compared to someone with a level less than 200 mg/dL.

LDLC levels are predictors of risk of cardiovascular event. Typically, the higher the LDLC, the more at risk a human subject is for a cardiovascular event. Levels of LDLC over 160 mg/dL may put a human subject at higher risks of a cardiovascular event(s) as compared to someone with a level less than 160 mg/dL. Levels of LDLC over 130 mg/dL in a human subject with one or more risk factors for a future cardiovascular event may put a human subject at higher risk of a cardiovascular event(s) as compared to someone with a level less than 130 mg/dL. A level of LDLC less than 100 mg/dL is desirable in a human subject who has had a prior cardiovascular event and is on therapy to reduce the risk of a future cardiovascular event and places the human subject in a group at less risk for a cardiovascular event. A level of LDLC less than 70 mg/dL is even more desirable in such a human subject to reduce the risk of a future cardiovascular event.

When a therapeutic agent is administered, it is administered in an amount effective to improve the symptoms associated with a cardiac disease or disorder or fibrosis-related disease or to reduce the risk of developing a cardiac disease or disorder or a fibrosis-related disease. An effective amount is a dosage of the therapeutic agent (e.g., IL-33 or soluble ST2 inhibiting agent) alone or in combination with another therapeutic agent sufficient to provide a medically desirable result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health care practitioner. It should be understood that the compositions provided herein can be used to prevent the development of a cardiac disease or disorder and/or the occurrence of a cardiovascular event, that is, they can be used prophylactically. The compositions can also, in some embodiments, be used to prevent the development of a fibrosis-related disease. Thus, an effective amount includes amounts that can lower the risk of, slow or perhaps prevent altogether the development of a disease or disorder, or, in some embodiments, the occurrence of a cardiovascular event. When the therapeutic agent is one that binds to cellular adhesion molecules and inhibits the ability of white blood cells to attach to such molecules, then the agent may be used prophylactically or may be used in acute circumstances, for example, post-myocardial infarction or post-angioplasty. It will be recognized when the therapeutic agent is used in acute circumstances, it is used to prevent one or more medically undesirable results that typically flow from such adverse events. In the case of myocardial infarction, the therapeutic agent can be used to limit injury to cardiac tissue which develops as a result of the myocardial infarction and in the case of restenosis, the therapeutic agent can be used in amounts effective to inhibit, prevent or slow the reoccurrence of blockage.

"Co-administering," as used herein, refers to administering simultaneously two or more therapeutic agents (e.g., an IL-33 nucleic acid and/or polypeptide, and a second therapeutic agent) as an admixture in a single composition, or sequentially, and, in some embodiments, close enough in time so that the compounds may exert an additive or even synergistic effect. In other embodiments, the therapeutic agents are administered concomitantly. In still other embodiments, one therapeutic agent is administered prior to or subsequent to another therapeutic agent.

Generally, doses of active compounds or agents can be from about 0.01 mg/kg per day to 1000 mg/kg per day. It is expected that doses ranging from 1-5 mg/kg, 5-50 mg/kg or 50-100 mg/kg can be suitable for oral administration and in one or several administrations per day. Lower doses will result from other forms of administration, such as intravenous administration. In the event that a response in a human subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

When administered, pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The therapeutic agents may be combined, optionally, with a pharmaceutically-acceptable carrier. The term "pharmaceutically-acceptable carrier" as used herein means one or more compatible solid or liquid filler, diluents or encapsulating substances which are suitable for administration into a subject. The term "carrier" denotes an organic or inorganic ingredient, natural or synthetic, with which the active ingredient is combined to facilitate the application. The components of the pharmaceutical compositions also are capable of being comingled with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the therapeutic agent, which is preferably isotonic with the blood of the subject. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular therapeutic agent selected, the severity of the condition being treated and the dosage required for therapeutic efficacy. The methods of the invention, generally speaking, may be practiced using any mode of administration that is medically acceptable, meaning any mode that produces effective levels of the active compounds or agents without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes can be used, in some embodiments, in emergency situations. Oral administration can be used, in some embodiments, for prophylactic treatment because of the convenience to the patient as well as the dosing schedule.

The pharmaceutical compositions may conveniently be presented in unit dosage form and may be prepared by any of the methods well-known in the art of pharmacy. All pharmaceutical methods include the step of bringing the therapeutic agent into association with a carrier which constitutes one or more accessory ingredients. In general, the compositions are prepared by uniformly and intimately bringing the therapeutic agent into association with a liquid carrier, a finely divided solid carrier, or both, and then, if necessary, shaping the product.

Compositions suitable for oral administration may be presented as discrete units, such as capsules, tablets, lozenges, each containing a predetermined amount of the therapeutic agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the therapeutic agent, increasing convenience to the subject and the health care practitioner. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the therapeutic agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for therapy of chronic conditions. Long-term release, as used herein, means that the implant is constructed and arranged to deliver therapeutic levels of the active ingredient for at least a few days, one week or a few weeks (e.g., 1, 2, 3 or 4 weeks). Long-term sustained release implants are well-known to those of ordinary skill in the art and include some of the release systems described above.

The invention further provides methods of identifying candidate agents useful in the treatment of cardiac disease or disorders or fibrosis-related diseases. Generally, the screening methods involve assaying for compounds which result in the increased expression of IL-33 and/or decreased expression of soluble ST2 (or a decrease in the level of soluble ST2 that is not bound by a soluble ST2 inhibiting agent or is free to bind IL-33) in a subject. Such methods are adaptable to automated, high throughput screening of compounds. A wide variety of assays for candidate (pharmacological) agents are provided, including, labeled in vitro protein binding assays, immunoassays, expression assays, etc.

Typically, but not necessarily so, a plurality of assay mixtures are run in parallel with different candidate agent concentrations to obtain a different response to the various concentrations. Typically, one of these concentrations serves as a negative control, i.e., at zero concentration of candidate agent or at a concentration of candidate agent below the limits of assay detection. Candidate agents encompass numerous chemical classes, although typically they are organic compounds. Preferably, the candidate agents are small organic compounds, i.e., those having a molecular weight of more than about 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. When the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be modified through conventional chemical, physical, and biochemical means. Further, known (pharmacological) agents may be subjected to directed or random chemical modifications such as acylation, alkylation, esterification, amidification, etc. to produce structural analogs of the agents.

The invention also provides kits for determining the expression level of IL-33 alone or in combination with soluble ST2 in a sample. In one embodiment, a kit comprises a package containing an agent that selectively binds to an IL-33 alone or in combination with an agent that selectively binds a soluble ST2 molecule, and a control for comparing to measured value(s) of binding of said agent(s). Kits are generally comprised of the following major elements: packaging, an agent(s), a control, and instructions. Packaging may be a box-like structure for holding a vial (or number of vials) containing an agent(s), a vial (or number of vials) containing a control, and instructions. Individuals skilled in the art can readily modify the packaging to suit individual needs. In some embodiments, the control is a predetermined value for comparing to the measured value. In certain embodiments, the control comprises an epitope of IL-33.

In the case of nucleic acid detection, pairs of primers for amplifying a nucleic acid molecule can be included. Preferred kits include known amounts of nucleic acid probes, epitopes or anti-epitope antibodies, as well as instructions or other printed material. In certain embodiments the printed material can characterize risk of developing a cardiac disease or disorder based upon the outcome of the assay.

The reagents may be packaged in containers and/or coated on wells in predetermined amounts, and the kits may include standard materials such as labeled immunological reagents (such as labeled anti-IL-33 antibodies) and the like. One kit is a packaged polystyrene microtiter plate coated with an anti-IL-33 antibody and a container containing labeled anti-IL-33 antibodies, wherein the labeled antibodies bind to a different epitope than the antibodies coating the microtiter plate. A well of the plate is contacted with, for example, a biological fluid, washed and then contacted with the anti-IL-33 antibody. The label is then detected. In preferred embodiments, kits or assays which are specific for, and have appropriate sensitivity with respect to, predetermined values selected on the basis of the present invention are provided. The preferred kits, therefore, would include, for example, cut-offs, sensitivities at particular cut-offs as well as instructions or other printed material for characterizing risk based upon the outcome of the assay.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Materials and Methods

Cell Culture and Cyclic Mechanical Strain

Cell culture of rat neonatal cardiomyocytes and cardiac fibroblasts was performed as previously described (1, 2). Briefly, hearts from neonates from 1 to 3 day-old Sprague-Dawley rats (Charles River, Wilmington, Mass.) were digested with trypsin (1 mg/ml, GIBCO, Invitrogen, Carlsbad, Calif.) and collagenase II (0.8 mg/ml, Worthington Biochemical Corporation, Lakewood, N.J.) and plated. Cardiomyocytes were serum-starved for at least 24 hrs. For cardiac fibroblasts, digested cells were plated on culture dishes for 1.5 hrs, and only attached cells were further cultured with Dulbecco's Modified Essential Medium (GIBCO) containing 10% fetal bovine serum. Cells after 2 passages were used for assay. Biomechanical strain of cells was performed as previously described (3, 4).

Quantitative PCR mRNA expression was analyzed by quantitative PCR using the QuantiTect SYBR Green reverse transcription-PCR kit (QIAGEN, Valencia, Calif.) and the Light Cycler System (Roche Applied Science, Indianapolis, Ind.) as previously described (5). Total RNA was extracted from cells with TRI reagent, and 0.2 μg of RNA was analyzed. Sequences of PCR primers were as follows (5' to 3'): TCGCACCTGTGACT-GAAATC (SEQ ID NO: 1) and ACACAGCATGCCA-CAAACAT (SEQ ID NO: 2) (IL-33); ATACAGTGCGGT-GTCCAACA (SEQ ID NO: 3) and CGAGAGCACCTCCATCTCTC (SEQ ID NO: 4) (ANP); GGAAATGGCTCAGAGACAGC (SEQ ID NO: 5) and CGATCCGGTCTATCTTCTGC (SEQ ID NO: 6) (BNP); TTGACCCTAACCAAGGATGC (SEQ ID NO: 7) and CAC-CCCTTCTGCGTTGTATT (SEQ ID NO: 8) (procollagen I); GACAGATGCTGGTGCTGAGA (SEQ ID NO: 9) and GCCTGATCCATGTAGGCAAT (SEQ ID NO: 10) (collagen III).

Northern Analysis

Purified RNA from adult rat brain was used for synthesis of cDNA with reverse transcriptase-polymerase chain reaction with Taq polymerase (Sigma, St. Louis, Mo.). The primer set for the synthesis of the 471 base pair IL-33 cDNA probe and the 245 base pair soluble ST2 cDNA probe were as follows (5' to 3'): AGTATCCAAGGAACTTCACTGCTA (SEQ ID NO: 11) and TTACATCTTAGAGAGCTTAAACATGAT (SEQ ID NO: 12) (IL-33); TTACCCAGCCAGGATGTTTC (SEQ ID NO: 13) and CTAGGGGCTTGGCTTCTCTT (SEQ ID NO: 14) (soluble ST2). Northern analysis was performed as previously described (3). Autoradiograms were quantified by densitometry (Scion Image 4.0), and mRNA levels were normalized to density of 28S ribosomal RNA ethidium bromide staining.

Recombinant Rat IL-33 Protein Production

The GenBank™ accession number for rat IL-33 is BC081993. Rat IL-33 cDNA was subcloned into the expression vector pTrcHis-TOPO vector (Invitrogen), starting with amino acid 109 of the full-length protein with N-terminal His tag. After sequencing, One Shot TOP10 cells (Invitrogen) were transformed and expression was induced with Isopropyl β-D-1-thiogalactopyranoside (Sigma) at $OD_{600}$ of 0.6. Four hours after induction, bacteria were harvested, and the pellet was resuspended in B-PER Bacterial Protein Extraction Reagent (Pierce Biotechnology, Inc., Rockford, Ill.) with protease inhibitor cocktail (Sigma). The lysate was purified with Ni-chelating affinity chromatography using the Ni-NTA Purification system (Invitrogen). Purified IL-33 protein was further concentrated, dialyzed, and endotoxin level (<0.03 EU/µg protein) was determined by *Limulus* Amebocyte Lysate PYROGENT Ultra (Cambrex, East Rutherford, N.J.) as previously described (6).

Immunocytochemistry

Sarcomeric α-actinin staining for cardiomyocytes and BrdUrd labeling for cardiac fibroblasts were performed as described previously (5). Mouse monoclonal antibody to sarcomeric α-actinin (EA-53, Sigma) was diluted 1:100 and used. For cardiomyocyte size, cells were visualized using an inverted fluorescent microscope (IX-70; Olympus), and the surface area of the cardiomyocytes was calculated with ImagePro Express software. Cells from randomly selected fields were analyzed.

[$^3$H]Leucine Incorporation Assay

Leucine incorporation in rat neonatal cardiomyocytes was detected as previously described (7). Cells were pre-incubated with 1.0 µCi/mL [$^3$H]leucine for 24 hours. The medium was aspirated, and the cells were washed twice with ice-cold PBS and once with 10% trichloroacetic acid (TCA; Sigma) and fixed for 45 minutes at 4° C. with 10% TCA. After washing twice with cold 95% ethanol, radioactivity incorporated into the TCA-precipitable material was determined by liquid scintillation counting after solubilization in 0.15N NaOH.

Electromobility Shift Assay

Electromobility shift assays were performed as described previously (8). Cells were lysed for 10 minutes on ice in a solution containing 10 mM HEPES (pH 7.6), 15 mM KCl, 2 mM $MgCl_2$, 0.1 mM ethylenediamine tetraacetic acid (EDTA), 1 mM dithiothreitol (DTT), 0.5 mM phenylmethylsulphonylfluoride (PMSF), 10 µg/mL leupeptin and 0.2% Nonident P-40. Dishes were gently scraped, and nuclei were collected by centrifugation at 800 g for 30 seconds and then suspended in a solution of 50 mM HEPES, 400 mM KCl, 0.1 mM EDTA, 10% glycerol, 1 mM DTT, 0.5 mM PMSF and 10 µg/mL leupeptin. The mixture was incubated on ice for 30 minutes, and the supernatant was collected after centrifugation for 15 minutes at 400 g. Binding reactions were performed with 5 or 10 µg of nuclear protein in 10 mM Tris, 1 mM DTT, 1 mM EDTA, 5% glycerol, 0.1% Triton X-100, 1 mg poly(dIdC), 5 µg bovine serum albumin (BSA) and approximately 10,000 cpm of –32P-labeled oligonucleotide. The binding reactions for AP-1 activity also contained 5 mM $MgCl_2$. Control reaction mixtures contained a 100-fold excess of unlabeled oligonucleotide and were incubated with nuclear extracts of IL-1β-treated cells. DNA complexes were separated on a 4% nondenaturing polyacrylamide gel in Tris-HCl (6.7 mM), EDTA (1 mM) and ammonium acetate (3.3 mM). The oligonucleotides contained the NF-B binding site (sequence: 5'-AGT TGA GGG GAC TTT CCC AGG C-3' (SEQ ID NO: 15)) and were labeled by standard procedures.

Cell Proliferation and Cell Cycle Analysis

A 3-(4,5-dimethylthiazol-2-yl)-5-(3-carboxymethoxyphenyl)-2-(4-sulfophenyl)-2H-tetrazolium salt (MTS) assay was performed with CellTiter 96 $AQ_{ueous}$ One Solution Cell Proliferation Assay kit (Promega, Madison, Wis.). Actual cell number in each group was also counted manually after exclusion of dead cells by Trypan blue staining. Cell cycle of cardiac fibroblasts was analyzed as previously described (9). Briefly, cardiac fibroblasts were seeded at a density of 1.5× $10^5$ cells per 60 mm dishes and serum-starved for 24 hrs. After treatment, cells were trypsinized, fixed in 80% ethanol at –20° C. and labeled with 50 ug/ml propidium iodide (Sigma) with 50 ug/ml RNaseA (Sigma). Then propidium iodide fluorescence was analyzed by flow cytometer (CYTOMICS FC500, Beckman Coulter, Fullerton, Calif.). Total population was initially gated to remove cell debris, and $1 \times 10^4$ cells were assessed for each DNA histogram using CXP software (Beckman Coulter).

Western Analysis

Phosphorylation of MAP kinases and Akt were detected by Western analysis as previously described (5). Membranes were incubated with primary antibodies overnight (phospho ERK1/2 diluted 1:1000; phospho SAPK/JNK diluted 1:500; phospho p38 MAPK diluted 1:500; phospho Akt (Ser473) diluted 1:1000). All antibodies were from Cell Signaling Technology, Inc. (Danvers, Mass.) and were sequentially detected with horseradish peroxidase-conjugated goat anti-rabbit IgG and enhanced chemiluminescence.

Targeted ST2 Null Mice

All animal procedures were conducted in accordance with guidelines published in the Guide for the Care and Use of Laboratory Animals (National Research Council, National Academy Press, Washington, D.C., 1996) and approved by The Harvard Medical School Standing Committee on Animals. Targeted ST2 null mice were obtained (generated as described previously (10)) from Dr. Andrew N. J. McKenzie and maintained breeding in a virus-free facility. Littermate offspring were identified by genotyping using a PCR-based method and used as controls.

Transverse Aortic Constriction (TAC) and Injection of IL-33 Peptide

Targeted ST2 ablated mice and their wild-type littermates were employed for the experiment simultaneously. TAC was produced as described previously (11-13) on 8-10 week old mice. Some mice underwent daily intraperitoneal (i.p.) injection of IL-33 (2 µg suspended in 100 microliters of PBS with 0.2% bovine serum albumin) or vehicle beginning from the day after TAC operation to the day of harvest.

Echocardiography

Echocardiographic acquisition and analysis were performed by an echocardiographer blinded to treatment group. Light anesthesia with spontaneous respiration was achieved with intraperitoneal pentobarbital (10 µg/g). All images were taken at a heart rate greater than 400 beats per minute to minimize effects of anesthesia, using a Sonos 4500 (Philips, Bothell, Wash.) and a 15-MHz transducer. Three consecutive cardiac cycles were averaged. Left ventricular (LV) mass was calculated by the M-mode (cubic) method (14). The calculated and actual weights (taken at autopsy) had excellent correlation (r=0.88, P<0.0001, n=50 mice from 1 and 4 weeks after TAC).

Results

Figure 1B:
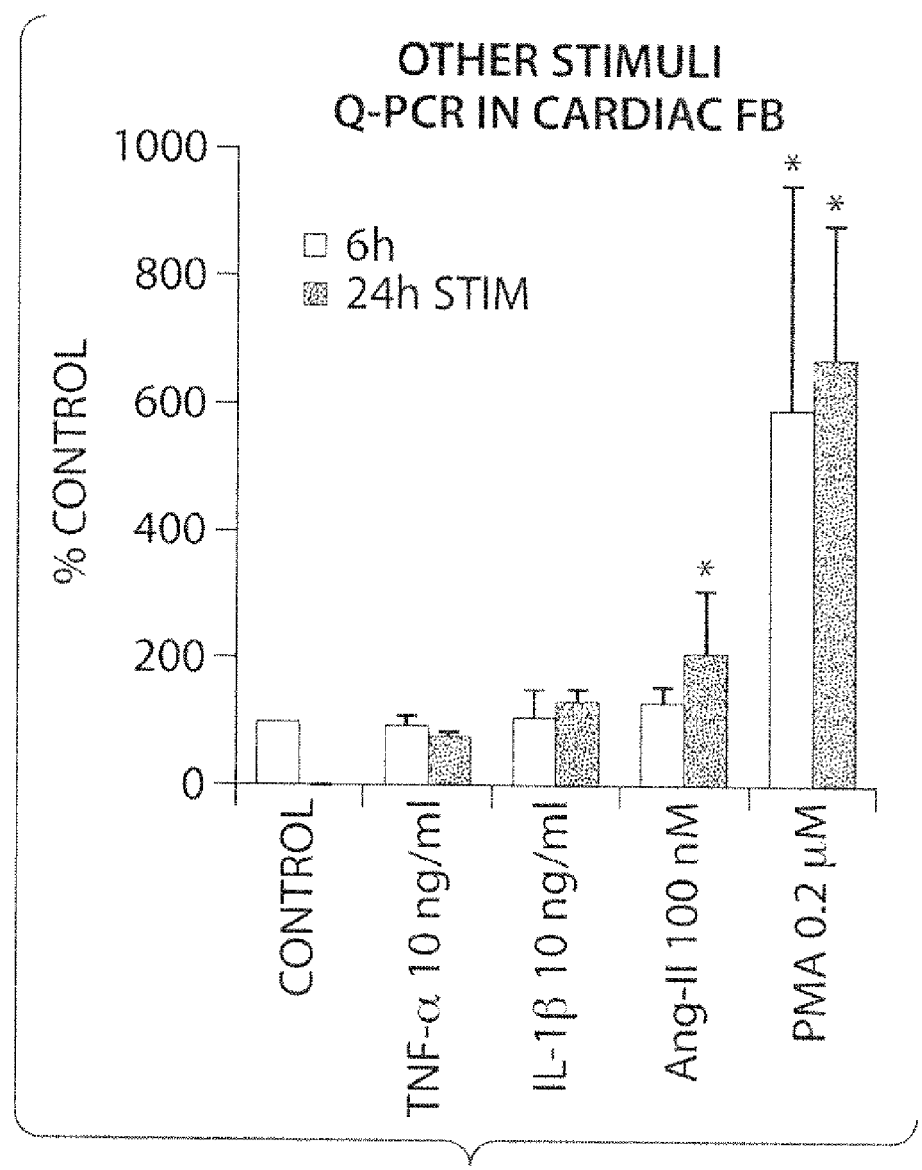

The results from the various experiments show that IL-33 is induced by cyclic mechanical stretch. Assays with cultured neonatal cardiac myocytes and cultured neonatal cardiac fibroblasts demonstrate that the gene for IL-33 is induced under conditions of cardiac strain (FIG. 1).

Figure 2:
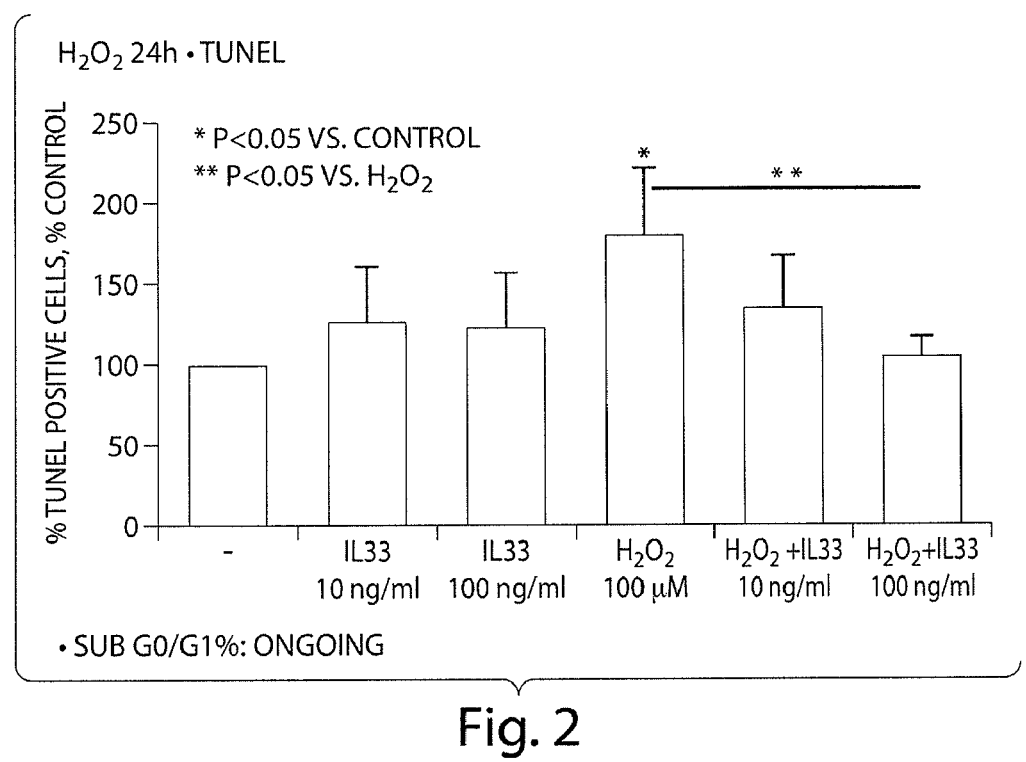
FIG. 2 illustrates that IL-33 can reduce apoptosis in cardiac myocytes when $H_2O_2$ is used to induce cardiomyocyte apoptosis.
Figure 3:
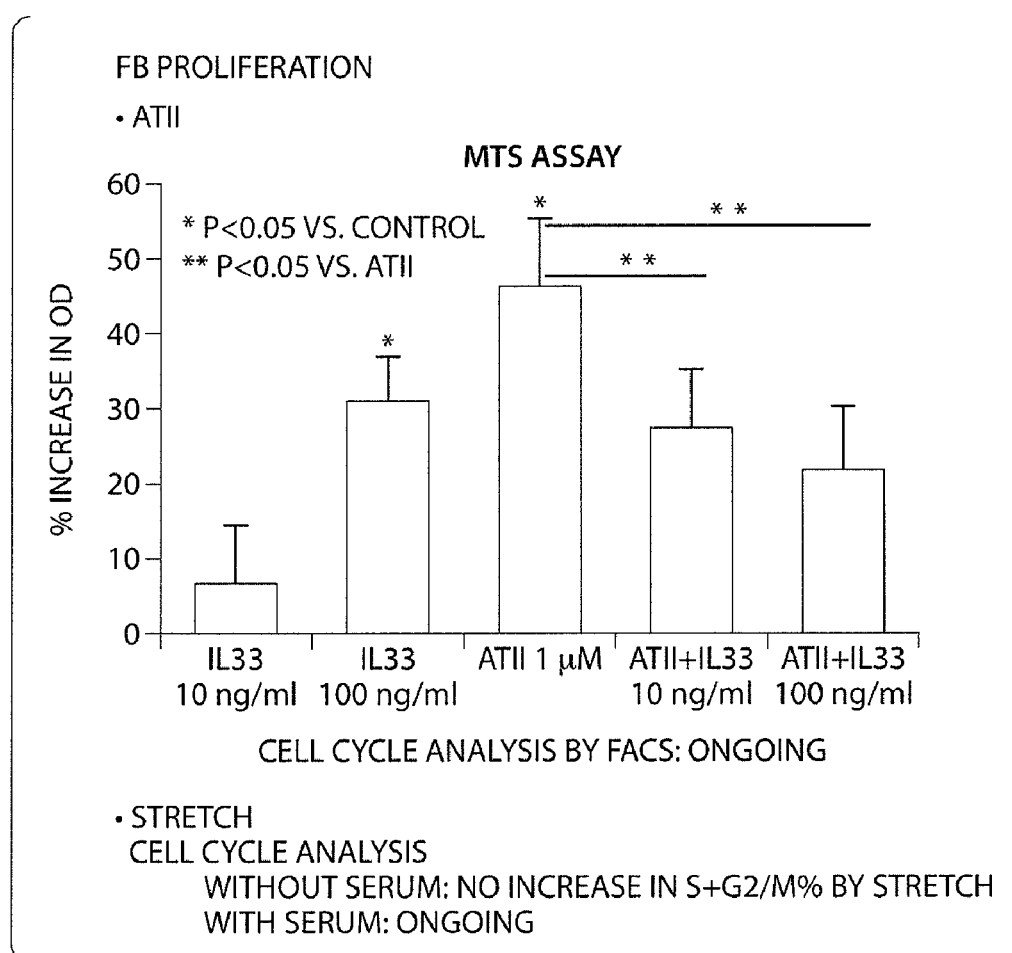
FIG. 3 demonstrates that IL-33 can induce cardiac fibroblast proliferation but that IL-33 antagonizes the proliferation induced by angiotensin II. Thus, IL-33 has some pro-fibrotic effects but can reduce the fibrosis from other stimuli.
Figure 7:
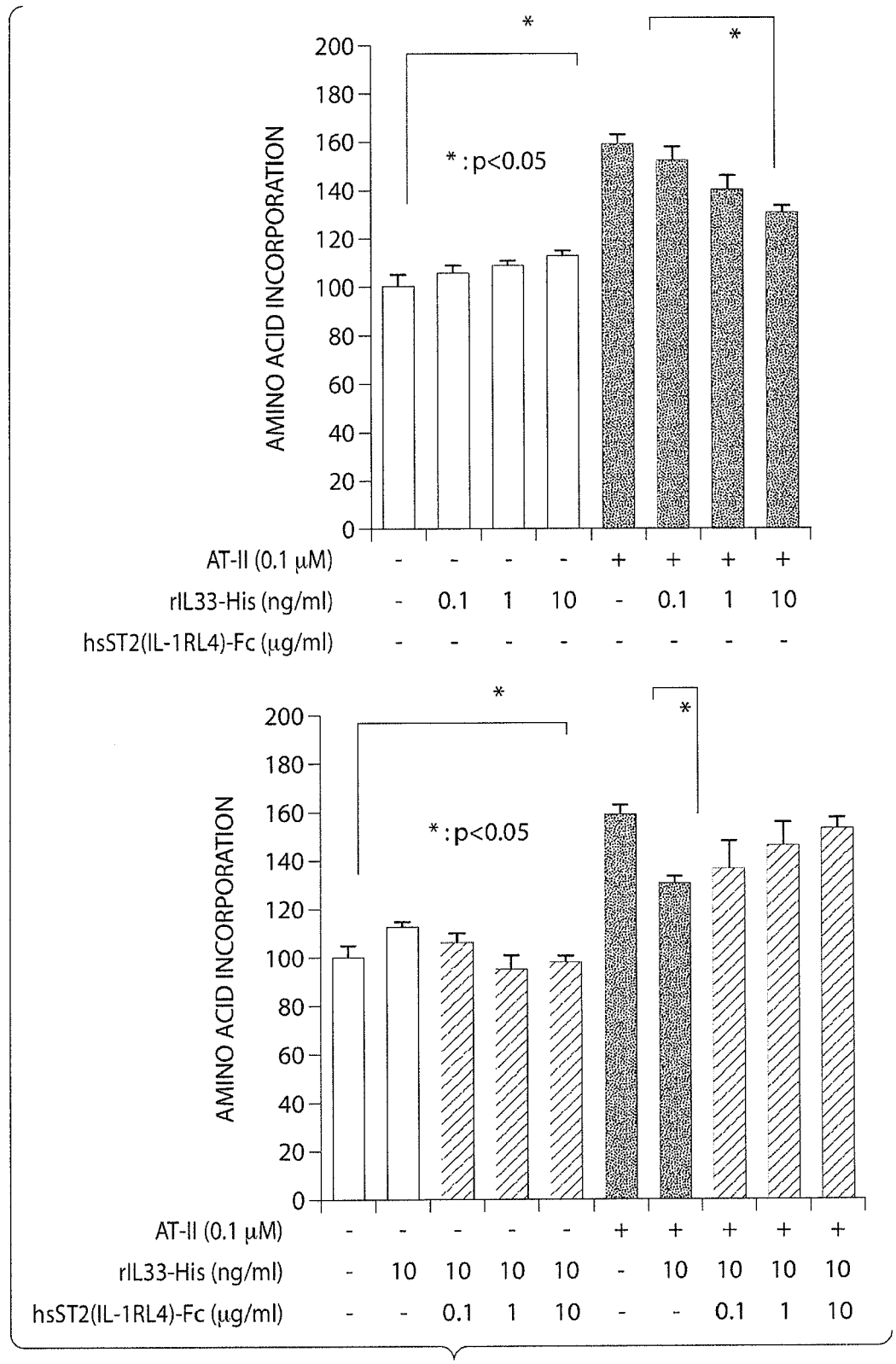
FIG. 7 demonstrates that adding purified recombinant IL-33 to cultured neonatal cardiac myocytes blocks hypertrophy induced by angiotensin II. The in vitro data suggest that IL-33 can inhibit adverse effects on cardiac myocytes.
Figure 8:
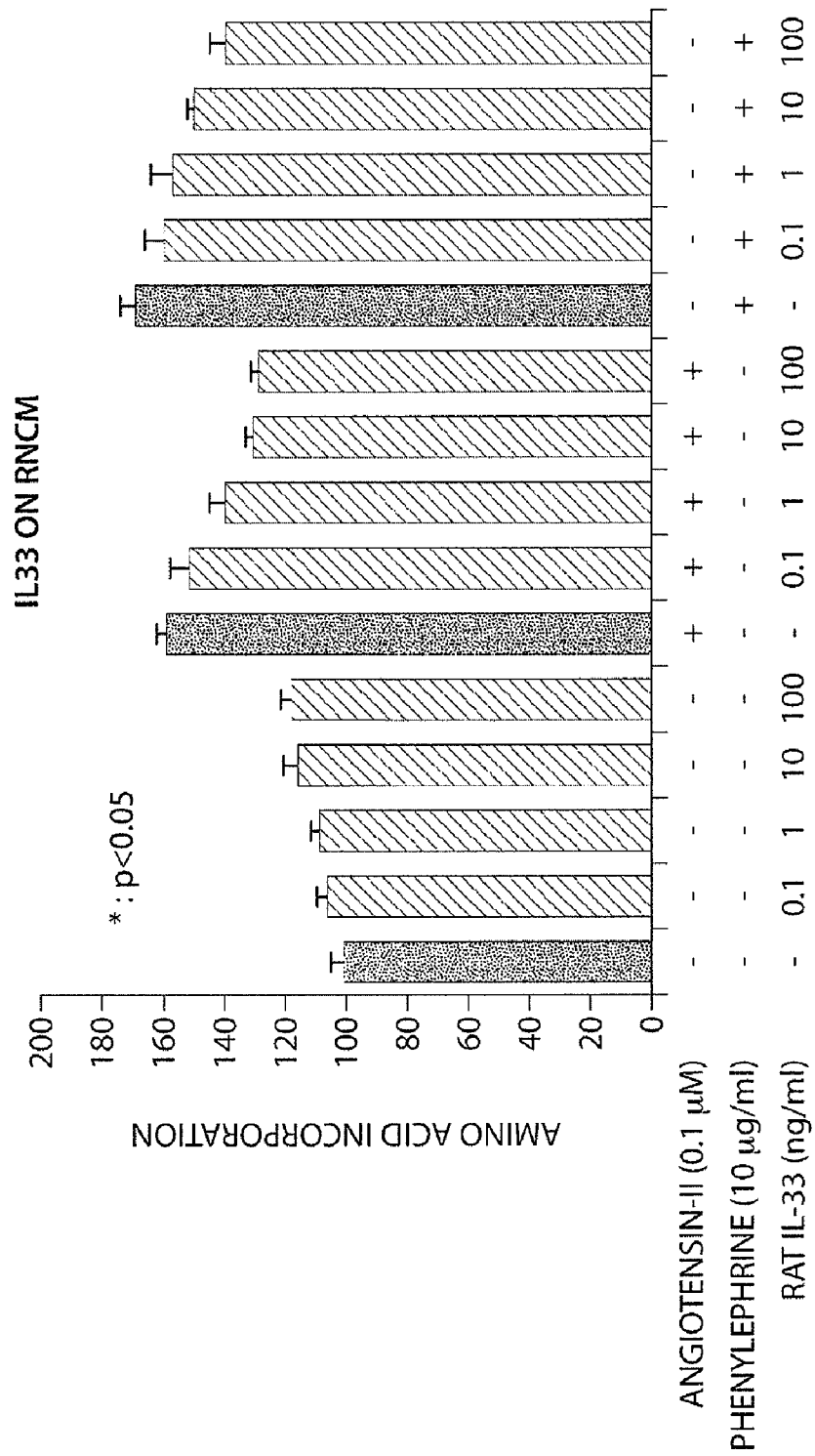
FIG. 8 shows that purified IL-33 has a modest hypertrophic effect in neonatal rat cardiomyocytes. However, IL-33 has a dose dependent ability to decrease hypertrophy induced by angiotensin II and phenylephrine.

The results from the various experiments also show that IL-33 can have beneficial effects, such as reducing apoptosis, fibrosis and hypertrophy. The data from the TUNEL assay show that IL-33 can reduce apoptosis in cardiac myocytes when $H_2O_2$ is used to induce cardiomyocyte apoptosis (FIG. 2), while the results provided in FIG. 3 show that IL-33 antagonizes cardiac fibroblast proliferation induced by angiotensin II. The results provided in FIGS. 7-8 show that IL-33 can block cardiac hypertrophy.

Figure 4:
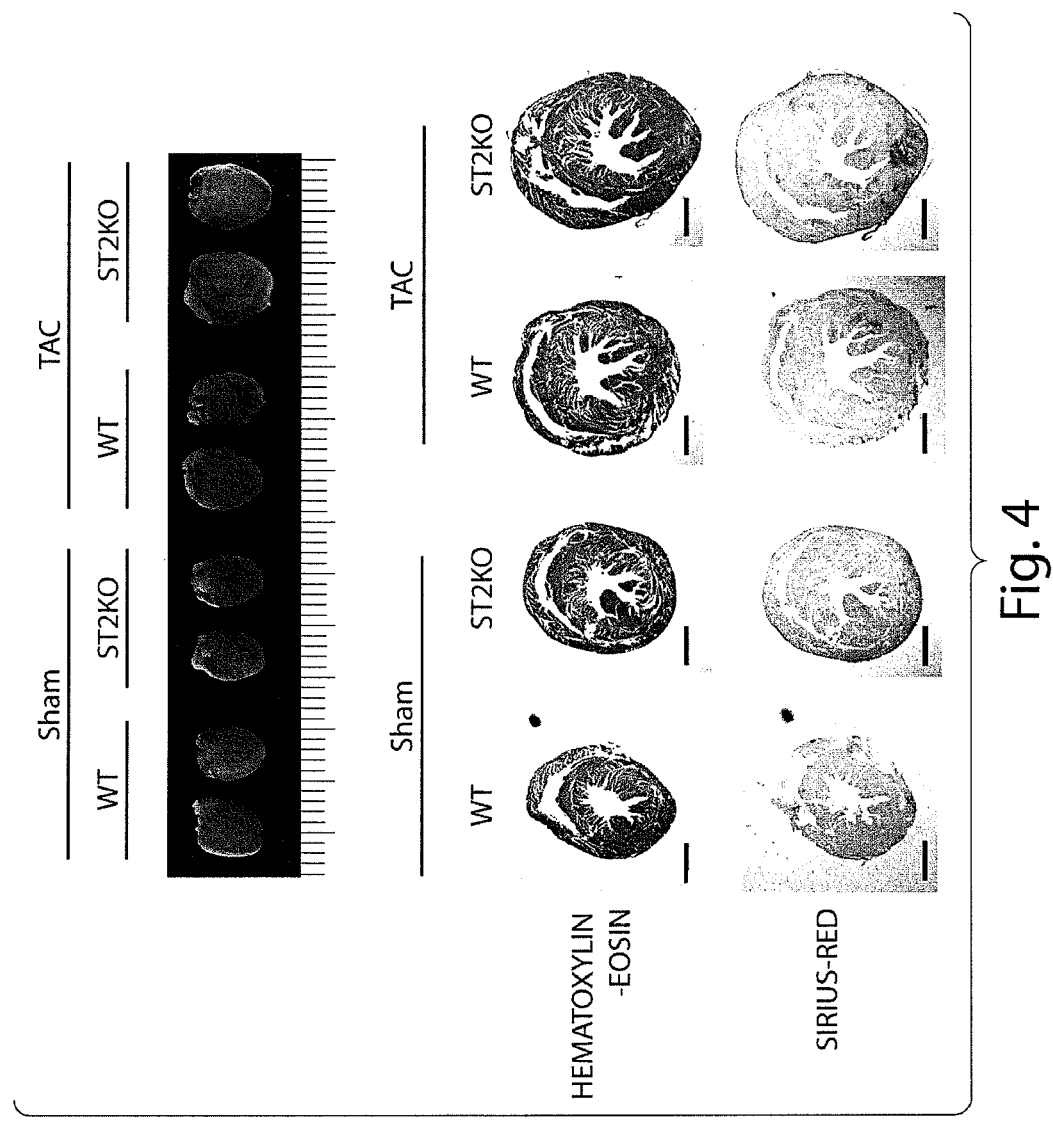
FIG. 4 shows that eliminating IL-33/ST2 signaling by deletion of the gene that encodes both the soluble and transmembrane form of ST2 leads to more cardiac hypertrophy and more fibrosis (Sirius Red staining) after 4 weeks of pressure overload (transverse aortic constriction (TAC) or aortic banding to increase ventricular pressure).
Figure 5:
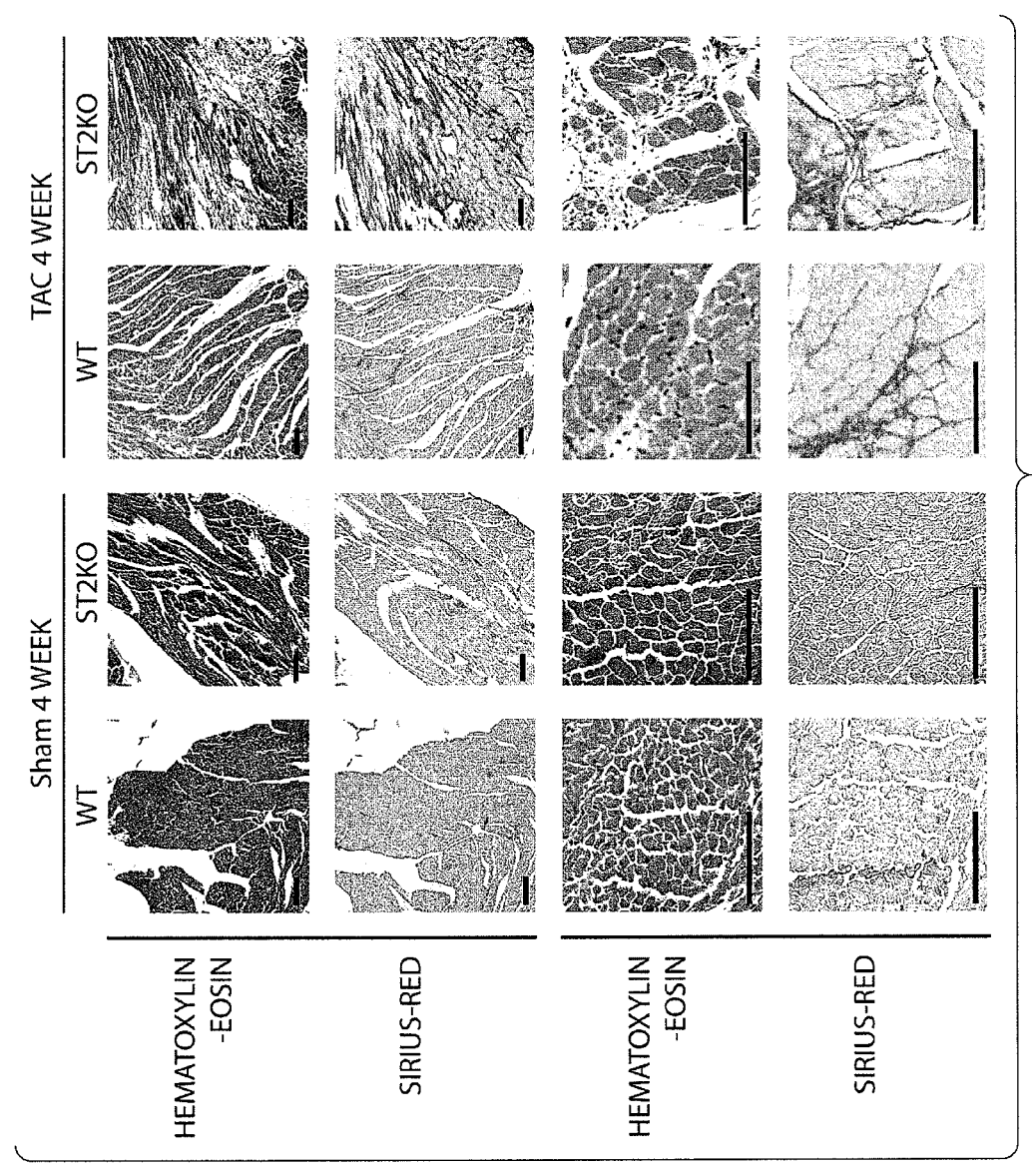
FIG. 5 provides histological sections that show worse pathology in the ST2 knock-out (KO) heart, indicating that eliminating IL-33/ST2 signaling is detrimental to the heart after TAC.
Figure 6:
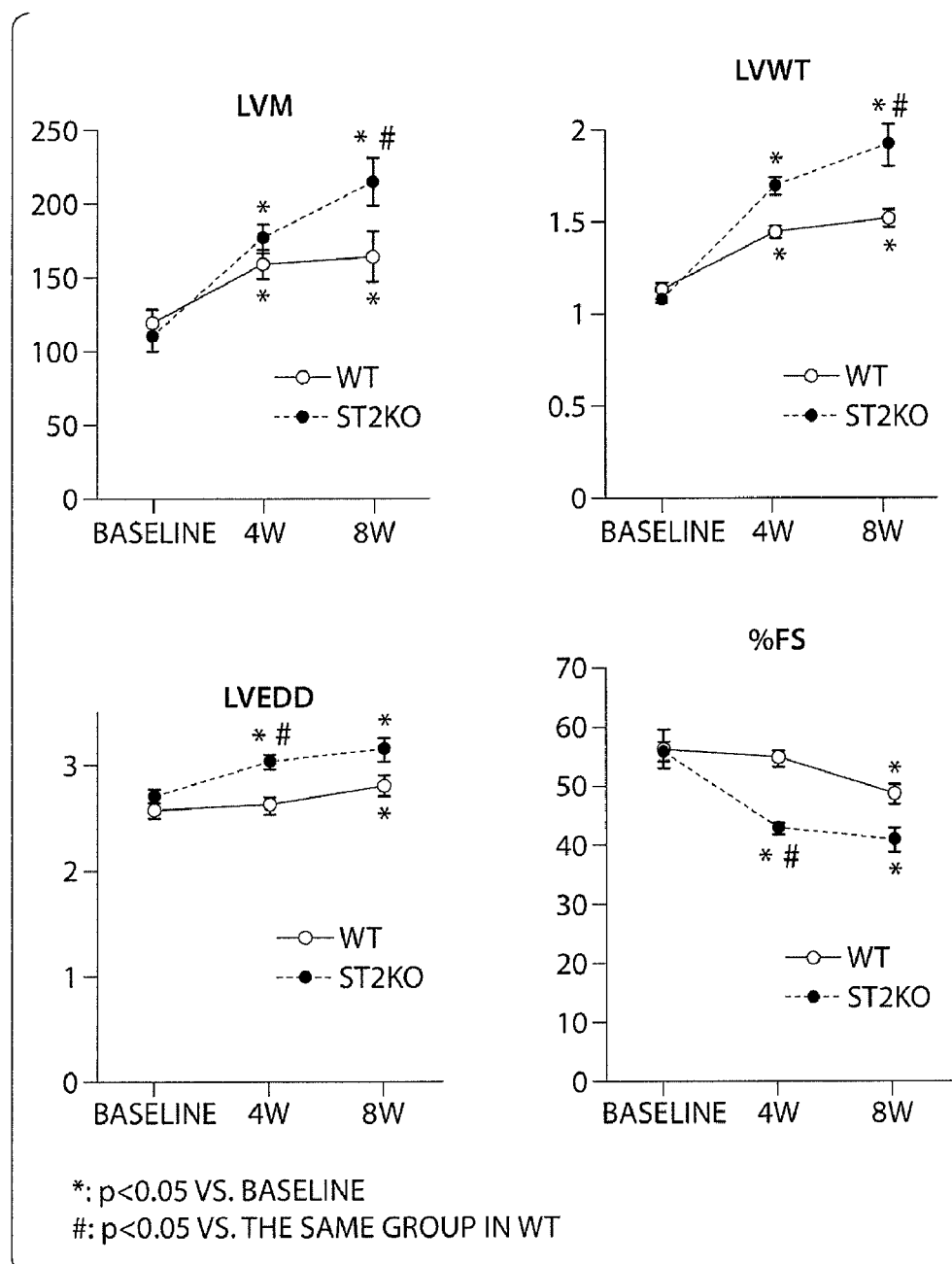
FIG. 6 provides echocardiographic results that show that cardiac systolic function (fractional shortening) is decreased by the elimination of IL-33/ST2 signaling. Also, ventricular size (LVEDD) and left ventricular mass are increased by the elimination of IL-33/ST2 signaling. The data suggest that IL-33 signaling through ST2 is protective.
Figure 10:
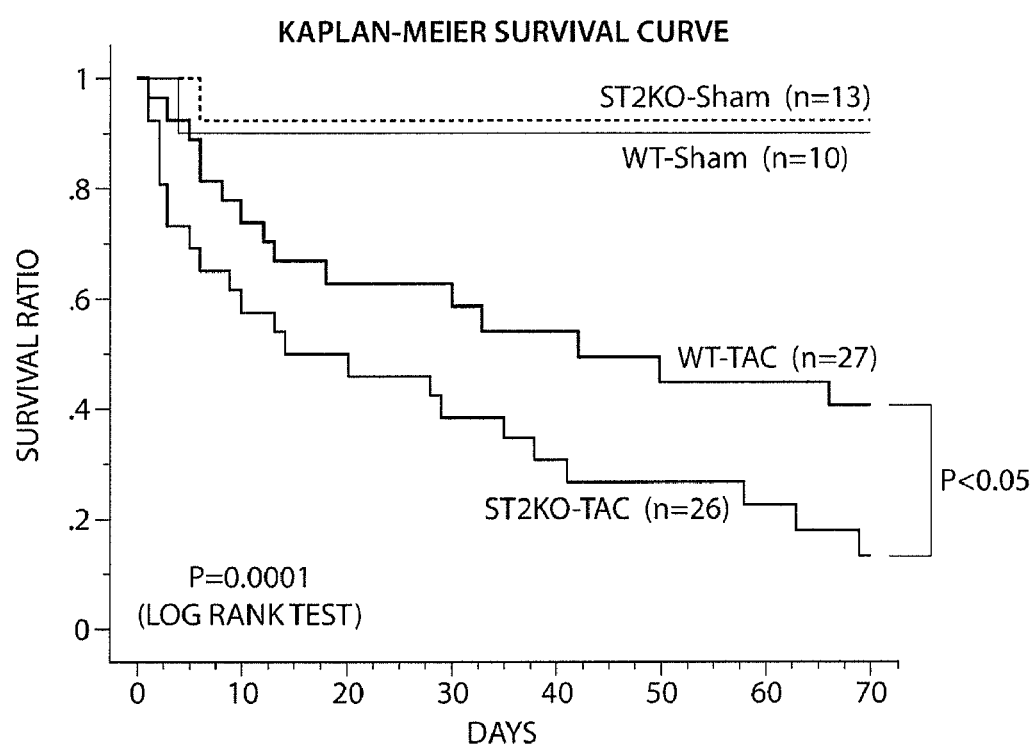
FIG. 10 shows that mice with deletion of ST2 have increased mortality (decreased survival) compared to wild-type mice following TAC. The data demonstrate that IL-33 signaling through transmembrane ST2 is cardioprotective, while the elimination of the signaling is detrimental.

In addition to showing the benefits of IL-33/ST2 signaling, the results from the various experiments also show that the elimination of IL-33/ST2 signaling is detrimental. Eliminating IL-33/ST2 signaling has been shown to result in more cardiac hypertrophy and fibrosis after aortic constriction surgery (FIG. 4). The elimination of signaling also leads to worse pathology. Histological sections show the worse pathology in the ST2KO heart (FIG. 5). Echocardiographic data also show that cardiac systolic function is decreased and ventricular size and left ventricular mass are increased by elimination of IL-33/ST2 signaling (FIG. 6). Finally, it has been demonstrated that the elimination of IL-33/ST2 signaling by deletion of ST2 in mice decreases survival after transverse aortic constriction (FIG. 10).

Figure 9:
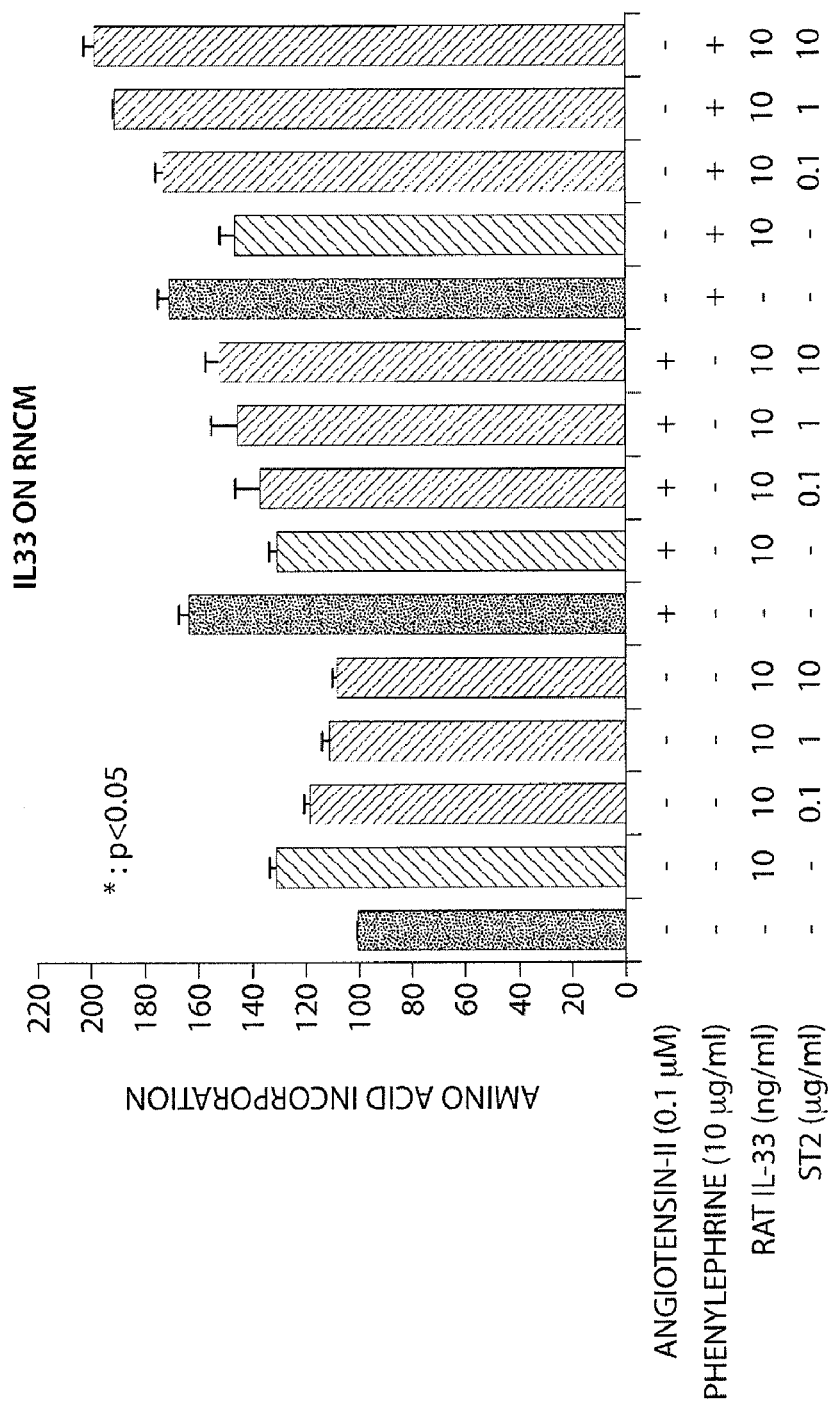
FIG. 9 illustrates that IL-33 can antagonize hypertrophic effects of angiotensin II and phenylephrine. When soluble ST2 is added, the effects of IL-33 are abolished. Soluble ST2 acts as a "decoy" receptor that prevents IL-33 from signaling to the membrane-bound ST2.

The mechanism by which IL-33 produces its beneficial effects has also been elucidated. With the results from the various experiments, it is shown that beneficial signaling occurs through membrane-bound ST2, while soluble ST2 abolishes it (FIG. 9). Soluble ST2 functions as a soluble "decoy" receptor that prevents IL-33 from signaling to membrane-bound ST2.

References for Example 1

1. Hsieh, P. C., et al., *Controlled delivery of PDGF-BB for myocardial protection using injectable self-assembling peptide nanofibers*. J Clin Invest, 2006. 116(1): p. 237-48.
2. Yokoyama, T., et al., *Angiotensin II and mechanical stretch induce production of tumor necrosis factor in cardiac fibroblasts*. Am J Physiol, 1999. 276(6 Pt 2): p. H1968-76.
3. Yamamoto, K., et al., *Induction of tenascin-C in cardiac myocytes by mechanical deformation. Role of reactive oxygen species*. J Biol Chem, 1999. 274(31): p. 21840-6.
4. Weinberg, E. O., et al., *Expression and regulation of ST2, an interleukin-1 receptor family member, in cardiomyocytes and myocardial infarction*. Circulation, 2002. 106 (23): p. 2961-6.
5. Hakuno, D., et al., *Focal adhesion kinase signaling regulates cardiogenesis of embryonic stem cells*. J Biol Chem, 2005. 280(47): p. 39534-44.
6. Schmitz, J., et al., *IL-33, an interleukin-1-like cytokine that signals via the IL-1 receptor-related protein ST2 and induces T helper type 2-associated cytokines*. Immunity, 2005. 23(5): p. 479-90.
7. Yamamoto, K., et al., *Peroxisome proliferator-activated receptor gamma activators inhibit cardiac hypertrophy in cardiac myocytes*. Circulation, 2001. 104(14): p. 1670-5.
8. Frantz, S., et al., *Toll4 (TLR4) expression in cardiac myocytes in normal and failing myocardium*. J Clin Invest, 1999. 104(3): p. 271-80.
9. Akli, S., et al., *E1A can provoke G1 exit that is refractory to p21 and independent of activating cdk2*. Circ Res, 1999. 85(4): p. 319-28.
10. Townsend, M. J., et al., *T1/ST2-deficient mice demonstrate the importance of T1/ST2 in developing primary T helper cell type 2 responses*. J Exp Med, 2000. 191(6): p. 1069-76.
11. Gottshall, K. R., et al., *Ras-dependent pathways induce obstructive hypertrophy in echo-selected transgenic mice*. Proc Natl Acad Sci USA, 1997. 94(9): p. 4710-5.
12. Rockman, H. A., et al., *Segregation of atrial-specific and inducible expression of an atrial natriuretic factor transgene in an in vivo murine model of cardiac hypertrophy*. Proc Natl Acad Sci USA, 1991. 88(18): p. 8277-81.
13. Tanaka, N., et al., *Transthoracic echocardiography in models of cardiac disease in the mouse*. Circulation, 1996. 94(5): p. 1109-17.
14. Collins, K. A., et al., *Accuracy of echocardiographic estimates of left ventricular mass in mice*. Am J Physiol Heart Circ Physiol, 2001. 280(5): p. H1954-62.

Example 2

Materials and Methods

ST2−/− Mice

Targeted ST2 disrupted mice were maintained on a 129× C57BL/6 background as described previously (18). All animal procedures were conducted in accordance with guidelines published in the Guide for the Care and Use of Laboratory Animals (National Research Council, National Academy Press, Washington, D.C., 1996) and approved by The Harvard Medical School Standing Committee on Animals.

Cell Culture and Cyclic Mechanical Strain

Cell culture of rat neonatal cardiomyocytes and cardiac fibroblasts was performed as previously described (42, 43). Briefly, hearts from 1-3 day-old Sprague-Dawley rat neonates (Charles River) were digested with trypsin (1 mg/ml, GIBCO) and collagenase-II (0.8 mg/ml, Worthington), and plated on non-coated culture dishes for 1.5 hrs. Attached cells were further cultured with Dulbecco's Modified Essential Medium (GIBCO) containing 10% fetal bovine serum and used as cardiac fibroblasts after 2 passages. Non-attached cells were re-plated on 0.1% gelatin-precoated dishes and further cultured with 7% fetal bovine serum as cardiomyocytes. Cells were serum-starved for 24 hrs prior to experiments. Biomechanical strain of cells was performed as previously described (6, 44). For in vitro cell size analysis, cardiomyocytes were plated at 30 to 40% confluence to allow definition of cell borders.

Quantitative PCR mRNA expression was analyzed by quantitative PCR using the QuantiTect SYBR Green reverse transcription-PCR kit (QIAGEN) and the Light Cycler System (Roche Applied Science) as previously described (45). Total RNA was extracted from cells with TRI reagent, and 0.2 µg of RNA was analyzed. Sequences of PCR primers were as follows (5' to 3'): TCGCACCTGTGACTGAAATC (SEQ ID NO: 1) and ACACAGCATGCCACAAACAT (SEQ ID NO: 2) (rat IL-33); ATACAGTGCGGTGTCCAACA (SEQ ID NO: 3) and CGAGAGCACCTCCATCTCTC (SEQ ID NO: 4) (rat ANP); GGAAATGGCTCAGAGACAGC (SEQ ID NO: 5) and CGATCCGGTCTATCTTCTGC (SEQ ID NO: 6) (rat BNP).

Northern Analysis

Purified RNA from adult rat brain was used for the synthesis of cDNA with reverse transcriptase-polymerase chain reaction. The primer set for the synthesis of the 471 base pair IL-33 cDNA probe, the 245 base pair sST2 cDNA probe and the 242 base pair of mouse BNP cDNA probe were as follows (5' to 3'): AGTATCCAAGGAACTTCACTGCTA (SEQ ID NO: 11) and TTACATCTTAGAGAGCTTAAACATGAT (SEQ ID NO: 12) (IL-33); TTACCCAGCCAGGATGTTTC (SEQ ID NO: 13) and CTAGGGGCTTGGCTTCTCTT (SEQ ID NO: 14) (sST2); ATACAGTGCGGTGTCCAACA (SEQ ID NO: 3) and CGAGAGCACCTCCATCTCTC (SEQ ID NO: 4) (rat ANP); CAGCTCTTGAAGGACCAAGG (SEQ ID NO: 16) and AGACCCAGGCAGAGTCAGAA (SEQ ID NO: 17) (mouse BNP). Northern analysis was performed as previously described (44). Autoradiograms were quantified by densitometry (Scion Image 4.0), and mRNA levels were normalized to densitometry of 18S or 28S ribosomal RNA ethidium bromide staining.

Production of Recombinant Rat IL-33 Protein and Polyclonal Anti-Rat IL-33 Antibody The GenBank™ accession number for rat IL-33 is BC081993. The rat IL-33 cDNA was subcloned into the expression vector pTrcHis-TOPO (Invitrogen), starting with amino acid 109 of the full-length protein with an N-terminal His tag. After sequencing, One-shot TOP10 bacteria (Invitrogen) were transformed and expression was induced with Isopropyl β-D-1-thiogalactopyranoside (Sigma). Four hours after induction, bacteria were harvested, and the pellet was resuspended in B-PER Bacterial Protein Extraction Reagent (Pierce) with EDTA-free protease inhibitor cocktail (Sigma). The lysate was purified with Ni-chelating affinity chromatography using a Ni-NTA Purification system (Invitrogen). Briefly, Ni NTA beads were washed twice after batch binding with 40 ml of 20 mM Imidazole, 300 mM NaCl, 50 mM potassium phosphate, pH 8.0. IL-33 was eluted with 10 ml of 250 mM Imidazole, 300 mM NaCl, 50 mM potassium phosphate, pH 8.0. IL-33 protein was further concentrated, dialyzed and purified by high-performance liquid chromatography (BioLogic DuoFlow System, Bio-Rad, Hercules, Calif.) using HiPrep sephacryl size exclusion column (GE Healthcare Bioscience, Piscataway, N.J.) with buffer containing 150 mM NaCl, 50 mM potassium phosphate, pH 7.2. Endotoxin level (<0.03 EU/µg protein) was determined by Limulus Amebocyte Lysate PYROGENT Ultra (Cambrex) as previously described (12). Using this protein, a polyclonal anti-rat IL-33 antibody was raised in rabbits (Maine Biotechnology, Portland, Me.); the antibody was purified with protein-A affinity chromatography. Pull-down assay between recombinant IL-33 with His tag and mouse ST2-Fc (R&D) was performed as described (12) with some modification, i.e., using Ni-NTA beads (Invitrogen) and anti-HisG antibody (Invitrogen) instead of agarose-bound Avidin-D and Streptavidin-HRP conjugate, respectively, followed by appropriate secondary HRP-conjugated antibody reaction for 1 h at room temperature and enhanced chemiluminescence.

[$^3$H]-Leucine Incorporation Assay

Leucine incorporation in rat neonatal cardiomyocytes was detected as previously described (46). Cells were treated with 1.0 µCi/ml [$^3$H]-leucine for 24 hours, washed, fixed with 10% trichloroacetate (Sigma) for 45 minutes at 4° C., and then radioactivity was determined by liquid scintillation counting. An anti-mouse ST2 antibody (R&D) was used as a functional neutralizing antibody (12). A normal rat IgG2a (Sigma) and mouse IL-1Rrp2 (R&D) were used as controls for anti-mouse ST2 antibody (R&D) and mouse soluble ST2 (R&D), respectively.

Fluorescence Microscopy

Immunofluorescence staining on paraffin-embedded mice hearts or rat neonatal cardiomyocyte cell culture was performed as described previously (42, 45). In addition to rabbit polyclonal anti-IL-33 antibody (1:100 dilution, as described above), mouse monoclonal (anti-vimentin, 1:100, Abcam, Cambridge) (42) and goat polyclonal (anti-discoidin domain receptor-2, 1:50, Santa Cruz, Santa Cruz, Calif.) (4, 15) antibodies were used to detect fibroblasts in separate specimens. Samples were visualized using an inverted fluorescent microscope (IX-70; Olympus). For measuring cardiomyocyte size, the surface area of the cells was calculated with ImagePro Express software. Cells from randomly selected fields were analyzed.

Immunohistochemistry and TUNEL Analysis

Formalin-fixed, paraffin-embedded sections were prepared as previously described (42). For immunohistochemistry, the first antibodies used were anti-cleaved caspase-3 (Cell Signaling Technology) and anti-mac3 (BD Biosciences, San Jose, Calif.). For TUNEL analysis, the In Situ apoptosis detection kit (Chemicon, Temecula, Calif.) was used along with the manufacturer's protocol with some optimal modifications on the treatment periods.

Electrophoretic Mobility Shift Assays

EMSAs were performed as described previously (47). Cells were lysed for 10 minutes on ice in 10 mM HEPES (pH 7.6), 15 mM KCl, 2 mM MgCl$_2$, 0.1 mM EDTA, 1 mM DTT, 0.5 mM PMSF, 10 µg/mL leupeptin, and 0.2% Nonident P-40. Dishes were gently scraped, and nuclei were collected by centrifugation at 800 g for 30 seconds and then suspended in a solution of 50 mM HEPES, 400 mM KCl, 0.1 mM EDTA, 10% glycerol, 1 mM DTT, 0.5 mM PMSF, and 10 µg/mL leupeptin. The mixture was incubated on ice for 30 minutes, and the supernatant was collected after centrifugation for 15 minutes at 400 g. Binding reactions were performed with 5 or 10 µg of nuclear protein in 10 mM Tris, 1 mM DTT, 1 mM EDTA, 5% glycerol, 0.1% Triton X-100, 1 mg poly(dIdC), 5 g BSA, and 10,000 cpm of [$^{32}$P]-labeled oligonucleotide. The specific NF-κB consensus oligonucleotides were 5'-AGT-TGAGGGGACTTTCCCAGGC-3' (SEQ ID NO: 15) and 5'-GCCTGGGAAAGTCCCCTCAACT-3' (SEQ ID NO: 18) (Promega). Positive and negative control mixtures as well as specific competition mixtures were made as recommended by the manufacturer's instructions, using binding buffer with positive samples, labeled NF-κB oligonucleotides and 10-fold excess of cold NF-κB consensus oligonucleotides for specific competition. DNA complexes were separated on a 6% nondenaturing polyacrylamide gel in Tris-HCl (6.7 mM), EDTA (1 mM), and ammonium acetate (3.3 mM).

NF-κB Luciferase Assay

Neonatal rat cardiomyocytes were transfected using Lipofectamine Plus (Invitrogen) with a luciferase reporter plasmid for NF-κB and with β-galactosidase, as described previously (47). After 48 hours of transfection, cells were then stimulated for an additional 24 hours, lysed and treated with Dual-Light assay system (Applied Biosystems, Foster City, Calif.), and analyzed using a luminometer (PerkinElmer Waltham, Calif.).

Oxidative Stress Assay

An assay to detect oxidative stress was performed as reported previously (48). Cardiomyocytes were incubated with 2,7-dichlorodihydrofluorecein diacetate (DCFDA) for 45 min, washed in phosphate-buffered saline, and fluorescence intensity was measured using a fluorometer (PerkinElmer Life Science) at 595 nm.

Immunoprecipitation

Immunoprecipitation was performed as described previously (45) with some modifications. Briefly, after wash with PBS, protein G-agarose beads were presaturated with far excessive amount of sST2-Fc protein (R&D) at 4° C. overnight, washed 3 times with PBS. 1 ml of conditioned media in the presence and absence of separated preincubation with 20

μg of the sST2-Fc protein was then incubated with presaturated beads for 2 hours at room temperature.

Western Analysis

Western analyses were performed as described previously (45). Membranes were incubated with primary antibodies overnight (anti-p44/42MAPK diluted 1:500; phospho-p44/42MAPK (Thr202/Tyr204) 1:1000; phospho-JNK (Thr183/Tyr185) 1:500; p38MAPK 1:500; phospho-p38MAPK (Thr180/Tyr182) 1:500; phospho-Akt (Ser473) 1:1000 and phospho-IκBα 1:1000, all from Cell Signaling, anti-mouse ST2L, from R&D 1:1000 and anti-IL-33 as described above, 1:500) at 4° C., detected with horseradish peroxidase-conjugated antibodies and enhanced chemiluminescence.

TAC and Treatment with IL-33 Protein

Targeted ST2−/− mice and their WT littermates were employed for the experiments. TAC was produced as described previously (49, 50) on 8-10 week old mice. All operative procedures were performed by a single operator with over 20 years rodent cardiac surgery experience who was blinded to genotype and the randomized treatment assignment. Following the procedure, each mouse received daily i.p. injection of recombinant rat IL-33 (2 μg) or vehicle from the day after TAC operation until the day of harvest.

Echocardiography

Echocardiographic acquisition and analysis were performed by an echocardiographer blinded to treatment group. Light anesthesia with spontaneous respiration was achieved with intraperitoneal pentobarbital (10 μg/g). All images were taken at a heart rate greater than 400 beats per minute to minimize effects of anesthesia, using a Sonos-4500 (Philips) and a 15-MHz transducer. Three consecutive cardiac cycles were averaged. Left ventricular mass was calculated by the M-mode method (51). Left ventricular fractional shortening was calculated as (EDD−ESD)/EDD×100%, where EDD is end-diastolic dimension and ESD is end-systolic dimension. The calculated and actual weights (taken at autopsy) had excellent correlation (r=0.88, P<0.0001, n=50 mice from 1 and 4 weeks after TAC).

Histological Analysis

A planimetry image analysis program was used by an investigator blinded to treatment group to quantitate the 30 high power field regions randomly selected in each slice with Hematoxylin-eosin stain (for cross-sectional area) or Sirius-red stain (for fibrotic area). Cross sectional area of cardiomyocytes was measured as described previously (52). Fibrotic area was calculated as (red area/total area)×100%. The scores from all slices were averaged to calculate their respective values.

Statistics

Data are expressed as mean±SEM. Statistical significance was determined using 2-tailed Student's t-test or ANOVA with Fisher's post hoc test as appropriate. Differences between groups were considered statistically significant at P<0.05.

Results

Figure 11A:
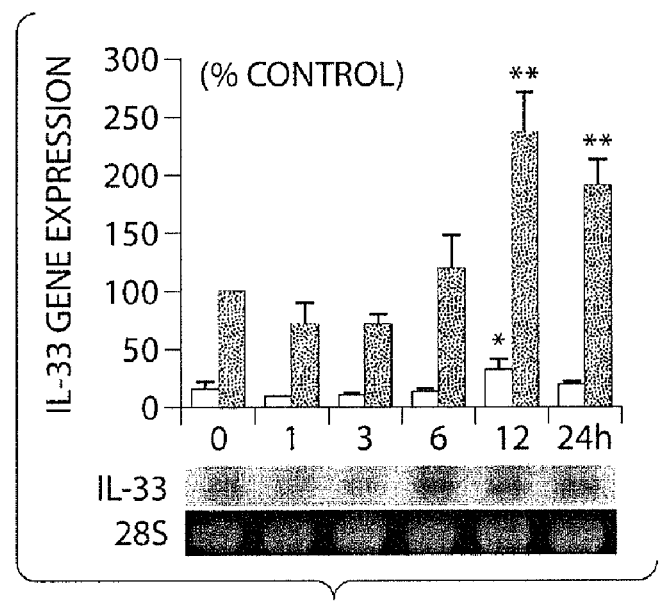
FIG. 11 demonstrates that IL-33 is induced by mechanical strain in cardiac fibroblasts. Quantitative analyses of gene expression of IL-33 by quantitative-PCR (FIG. 11A) and soluble ST2 (sST2) by Northern analysis (FIG. 11B) in rat neonatal cardiomyocytes (open bars) and fibroblasts (closed bars) are shown in the upper panels, accompanied by representative images from Northern analyses of cardiac fibroblast RNA in the lower panels. Each value was obtained as the ratio relative to β-tubulin expression and expressed as % of control in cardiac fibroblasts. Cells were subjected to cyclic strain (8%, 1 Hz) for indicated periods. *:$p<0.05$ and **:$p<0.01$ vs. baseline. Data are from at least 3 sets of independent experiments. Coomassie stain showed that the recombinant mature rat IL-33 with N-terminal His-tag was of high purity (FIG. 11C). 10 μg of protein was loaded.
FIG. 11D provides results from a pull-down assay of recombinant IL-33 with mouse ST2-Fc protein. The recombinant protein exhibits specific binding to mouse ST2. Results from a Western analysis of cardiomyocytes and cardiac fibroblasts subjected to cyclic strain for indicated periods are shown in FIG. 11E. 10 μg each of protein sample from whole cell lysate were applied. For reference, 0.1 ng of recombinant IL-33 was applied in the right lane.
FIG. 11F provides representative immunofluorescence microscopy images of left ventricular samples 1 week after Sham or Transverse Aortic Constriction (TAC) operation. Anti-vimentin (upper panels) or anti-discoidin domain receptor-2 (lower panels) antibody was used to detect fibroblasts (red) for dual-staining with IL-33 (green). Pressure overload by TAC induced IL-33 expression, particularly in non-cardiomyocyte interstitial cells. Scale bar=10 µm.
Figure 11B:
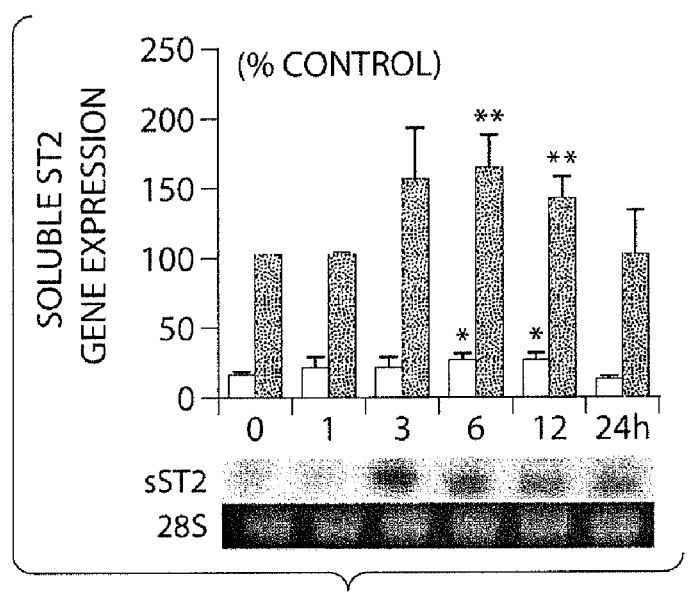

IL-33 is Mechanically-Induced in Cardiac Fibroblasts and Antagonizes Hypertrophic Stimuli Analysis of rat neonatal cardiomyocytes and cardiac fibroblasts revealed that gene expression of IL-33 as well as sST2 was >5 fold greater in cardiac fibroblasts than in cardiomyocytes (FIGS. 11A and 11B). Cyclic biomechanical strain (8%, 1 Hz) induced the expression of both IL-33 and sST2 in both cell types. In an evaluation of other stimuli, quantitative PCR showed that either phorbol 12-myristate 13-acetate (PMA, 0.2 μM) or angiotensin-II (0.1 μM) also induced the expression of IL-33 in both cell types; in contrast, neither TNF-α (10 ng/ml) nor IL-1β (10 ng/ml) induced IL-33 gene expression.

Figure 11C:
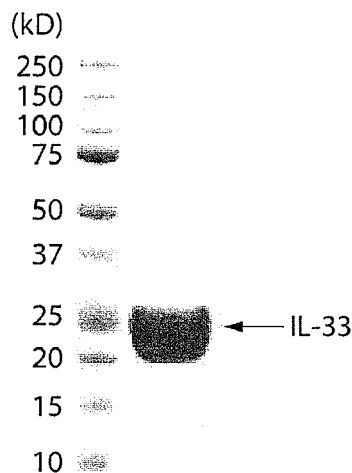
Figure 11D:
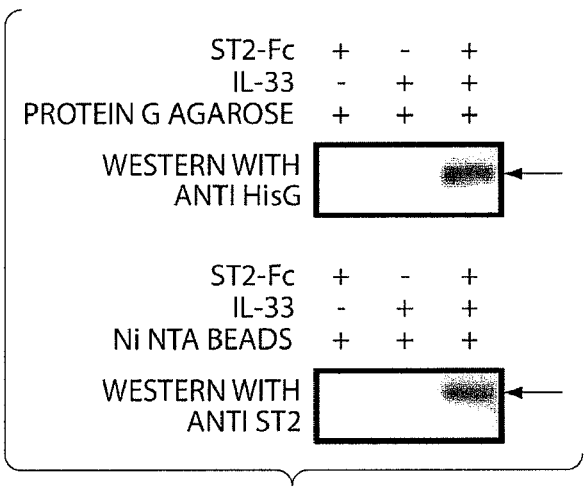
Figure 11E:
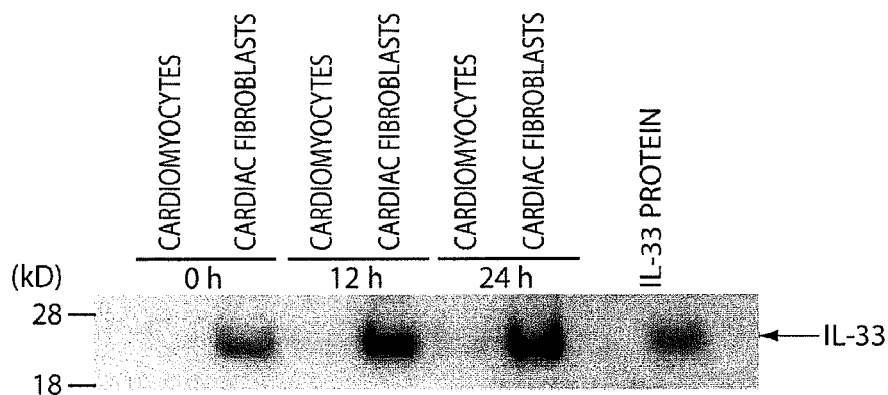
Figure 11F:
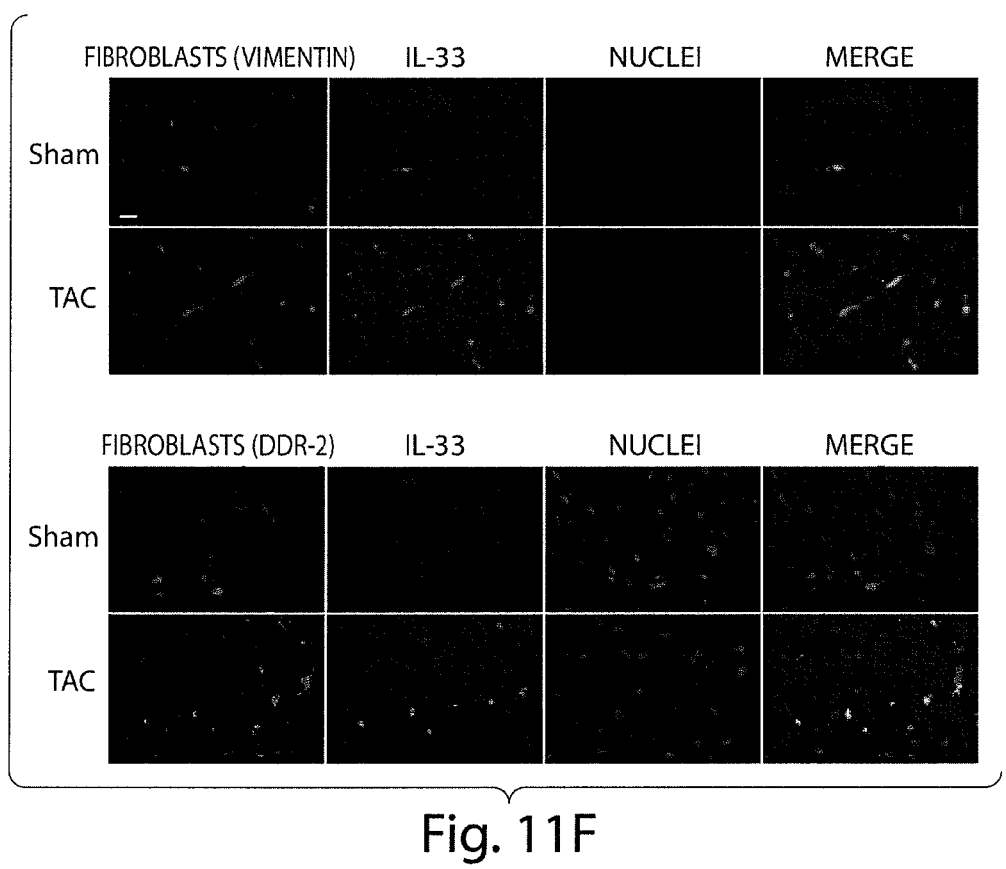

Recombinant rat IL-33 was expressed and purified using affinity chromatography. The recombinant IL-33 protein was of high purity with a single band visible with polyacrylamide electrophoresis and Coomassie staining (FIG. 11C), and the purified IL-33 bound to the mouse ST2 protein as demonstrated by pulldown of IL-33 using a recombinant ST2-Fc chimera protein (FIG. 11D). Endotoxin levels in the purified IL-33 were undetectable by *Limulus* Amebocyte lysate assay (<0.03 EU/μg protein). A rabbit polyclonal antiserum against rat IL-33 was raised, and the antibodies were purified from the antiserum by affinity chromatography. Western analysis showed that basal expression of IL-33 protein by cardiac fibroblasts was much greater when compared with cardiomyocytes, and cyclic biomechanical strain (8%, 1 Hz) induced IL-33 protein in both cell types (FIG. 11E). In vivo, immunofluorescent staining of mouse myocardium showed that pressure overload induced by transverse aortic constriction increased IL-33 protein expression in cardiac interstitial cells more than in cardiomyocytes (FIG. 11F). Immunofluorescence staining with antibodies to vimentin as well as the discoidin domain receptor-2 (DDR-2), which is expressed by cardiac fibroblasts but not by endothelial cells, smooth muscle cells or cardiac myocytes (4, 15), revealed nearly identical results (FIG. 11F).

Figure 12A:
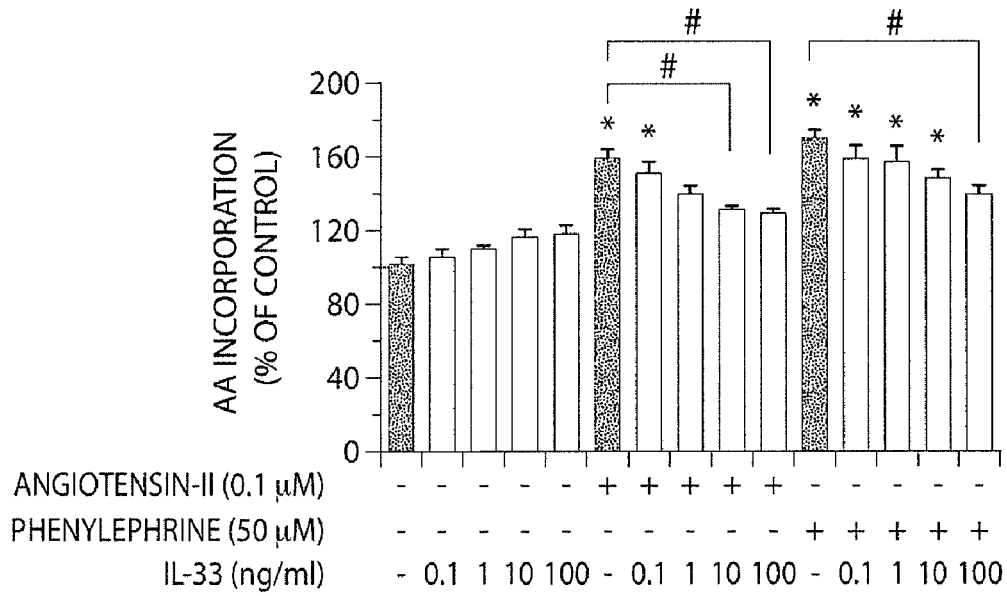
FIG. 12 illustrates that IL-33 blocks prohypertrophic stimuli in cardiomyocytes and soluble ST2 inhibits IL-33. IL-33 demonstrated a non-significant trend toward stimulating hypertrophy, but IL-33 blocked angiotensin-II or phenylephrine-induced leucine uptake in a dose-dependent manner (FIG. 12A). Soluble ST2 dose-dependently reversed the antihypertrophic effect of IL-33 under either angiotensin-II or phenylephrine (FIG. 12B). Anti-ST2 monoclonal antibody, which blocks membrane bound ST2 receptor binding activity, blocked the antihypertrophic effect of IL-33, unlike control IgG (FIG. 12C). Leucine uptake was not affected by soluble ST2 compared with either baseline or control protein, IL-1Rrp2, but further enhanced hypertrophy under either angiotensin-II or phenylephrine (FIG. 12D). Data are from 3-5 sets of experiments. Quantitative analysis of in vitro cell size measurements of cardiomyocytes was consistent with leucine incorporation assays (n=200 each) (FIG. 12E). *:$p<0.05$ vs. baseline and #:$p<0.05$. Induced secretion of both sST2 and IL-33 can reduce free IL-33 (FIG. 12F). Cardiac fibroblasts were treated with indicated doses of PMA for 24 hrs to induce sST2 and IL-33. In the upper panels, conditioned media (20 µl) were analyzed by Western analysis. PMA dose-dependently increased secretion of both IL-33 (top) and sST2 (middle). In the bottom panel, media was preincubated in the presence or absence of 20 µg of sST2-Fc protein and then incubated with presaturated beads for 2 hrs. Samples preincubated with sST2-Fc had little IL-33, indicating that preincubation with sST2-Fc removed free IL-33. PMA dose-dependently decreased free IL-33 despite an increase in overall IL-33; these data suggest that induced sST2 can function as a decoy receptor, decreasing free IL-33.
Figure 12B:
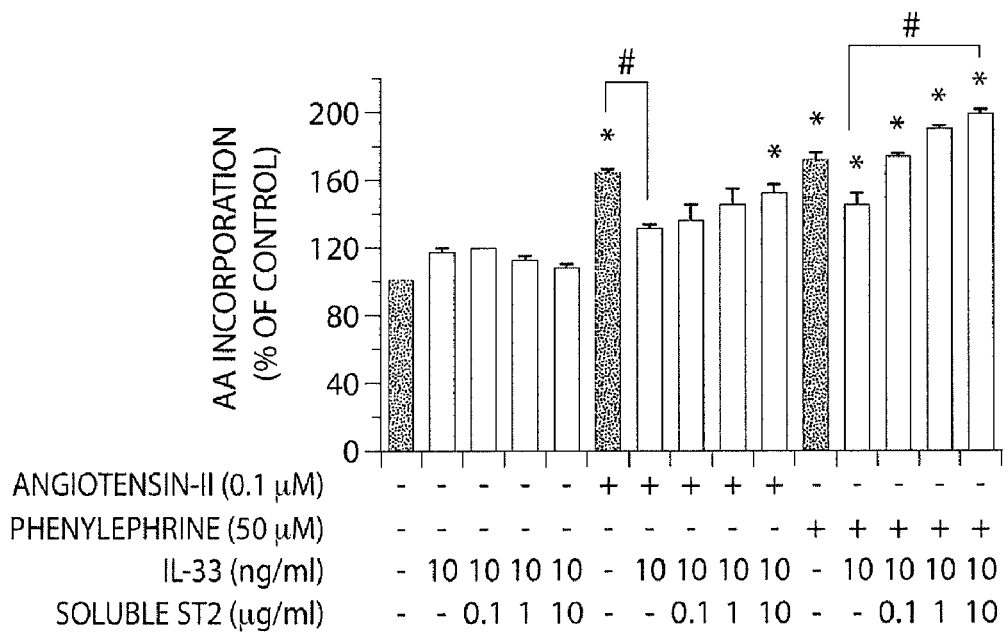
Figure 12C:
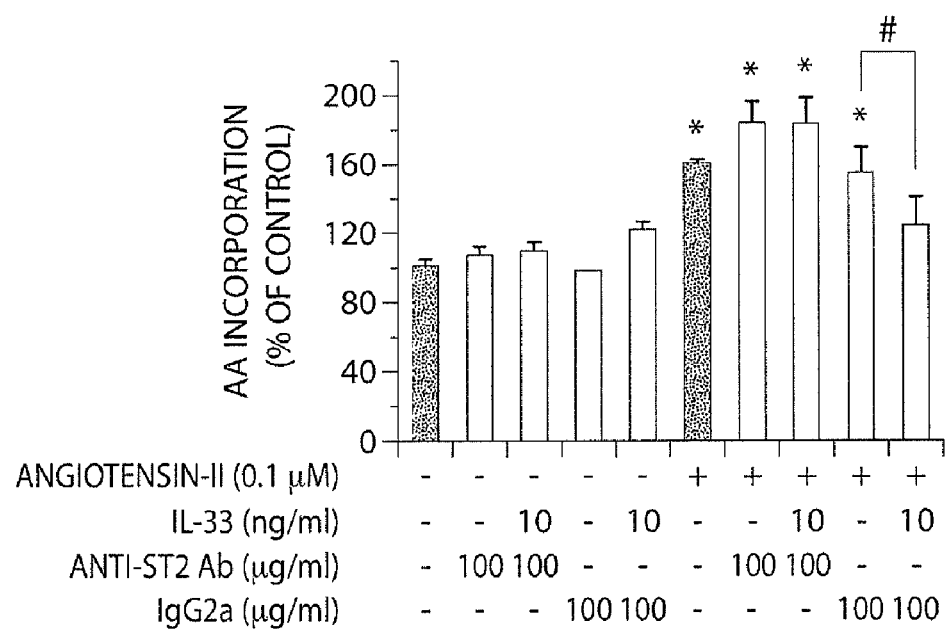
Figure 12D:
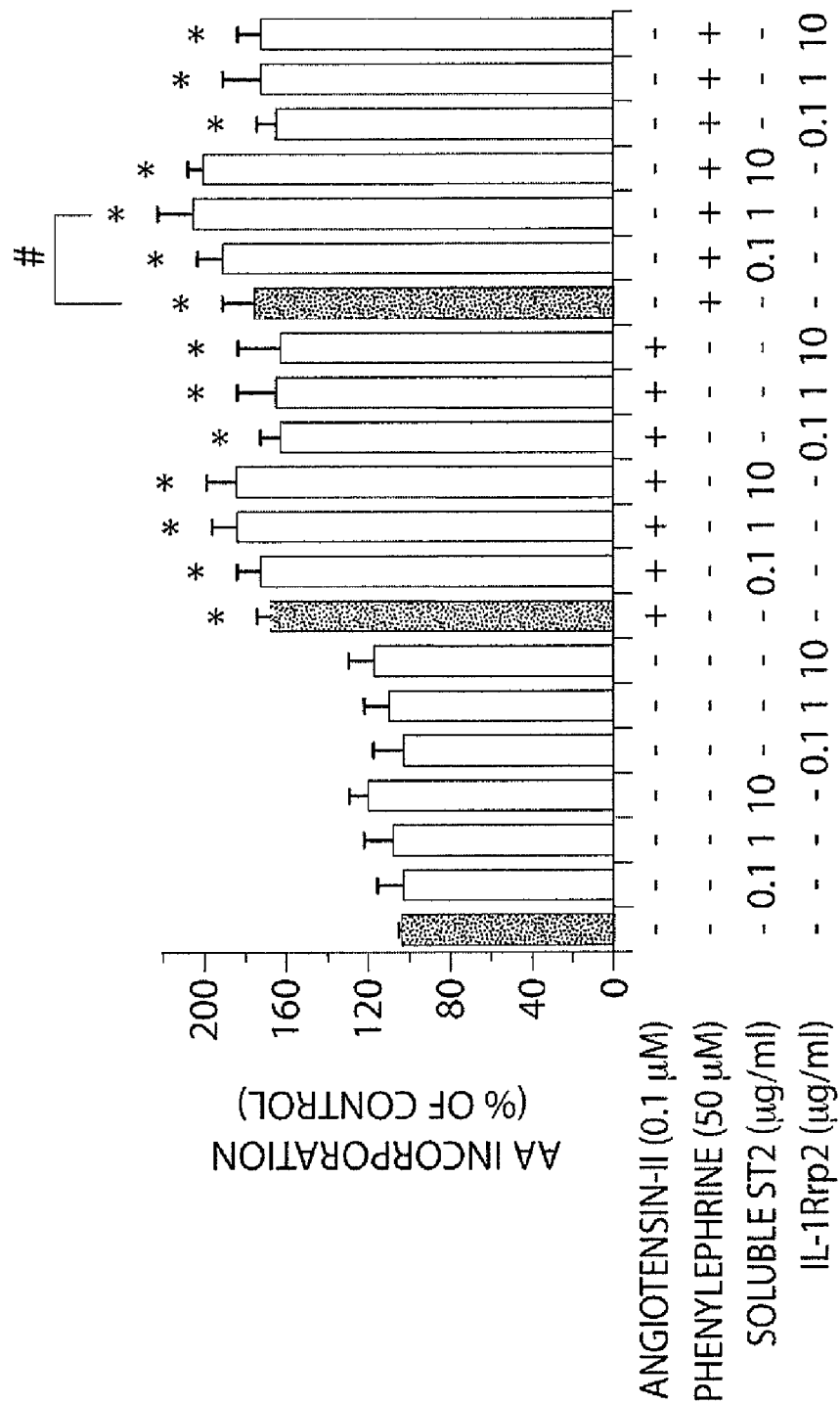
Figure 12E:
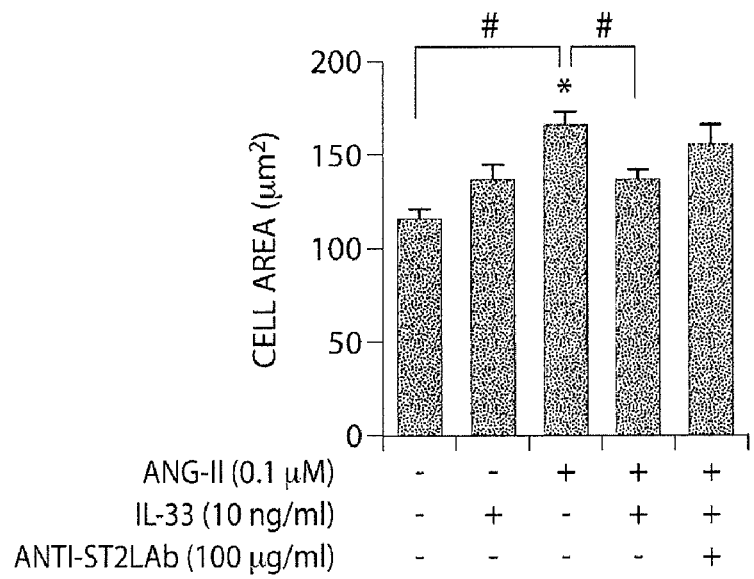

To determine the effects that cardiac fibroblast-secreted IL-33 might have on adjacent cardiomyocytes, cultured rat neonatal cardiac myocytes were treated with recombinant IL-33. In repeated experiments, IL-33 demonstrated a modest, dose-dependent pro-hypertrophic trend that was not statistically significant (FIG. 12A). However, IL-33 potently blocked cardiomyocyte hypertrophy induced by either angiotensin-II or phenylephrine in a dose-dependent manner (FIG. 12A). Soluble sST2 protein reversed the antihypertrophic effect of IL-33 in a dose-dependent manner, indicating that sST2 probably functions as a soluble "decoy" receptor by binding IL-33 and preventing ST2L signaling (FIG. 12B). Blocking the ST2L receptor with an anti-ST2L monoclonal antibody eliminated the antihypertrophic effect of IL-33, unlike control IgG (FIG. 12C), demonstrating that the effects of IL-33 are specifically through the ST2L receptor. In addition, the ability of sST2 to further augment the hypertrophic response under stimulation with either angiotensin-II or phenylephrine was not observed with a control protein from the IL-1 receptor family (IL-1Rrp2 fusion protein, FIG. 12D). The antihypertrophic effect of IL-33 was further confirmed by in vitro cell size measurement of cardiomyocytes (FIG. 12E) with or without angiotensin-II (0.1 μM) or IL-33 (10 ng/ml) stimulation as well as application of an anti-ST2 antibody (100 μg/ml) that was reported as a functional inhibitor of IL-33/ST2 signaling (12), which revealed results similar to the leucine uptake analysis. These data support the idea that IL-33 is a mechanically-induced ligand for ST2L, and that sST2 blocks IL-33/ST2L signaling.

Figure 12F:
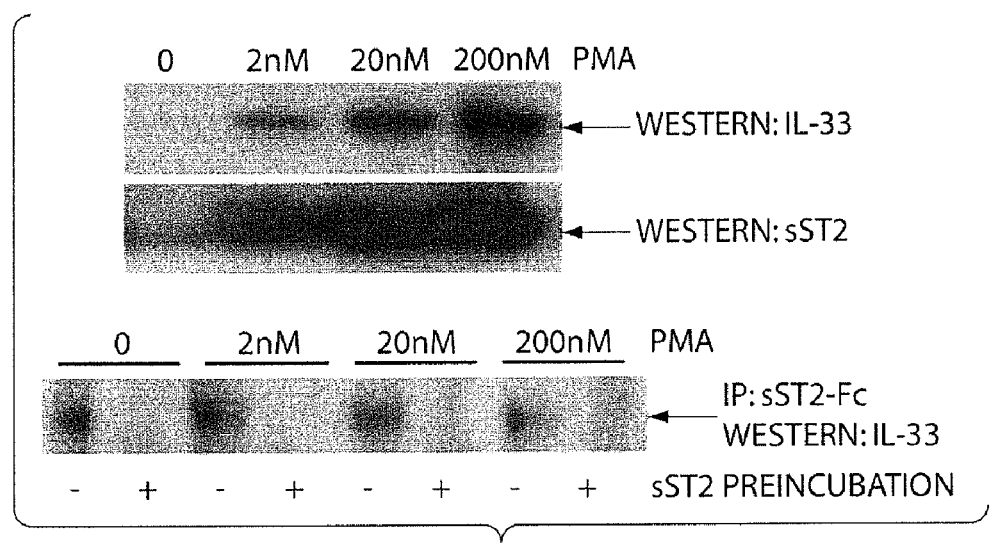

High levels of sST2 can predict worse prognosis in cardiovascular patients, raising the question that sST2 levels are sufficient to sequester endogenous IL-33 levels. Currently, information on endogenous IL-33 levels in humans is unavailable. However, the hypothesis that stimuli that increased sST2 could sequester unbound IL-33 was tested. When rat neonatal cardiac fibroblasts were stimulated with increasing doses of PMA, both sST2 and total IL-33 were induced (FIG. 12F). However, unbound IL-33 diminished, indicating that sST2 induction could limit IL-33 signaling (FIG. 12F). These data suggest that the local ratio of IL-33 and sST2 could regulate IL-33 signaling.

IL-33 Blocks NF-κB Activation by Angiotensin-II and Phenylephrine

Figure 13A:
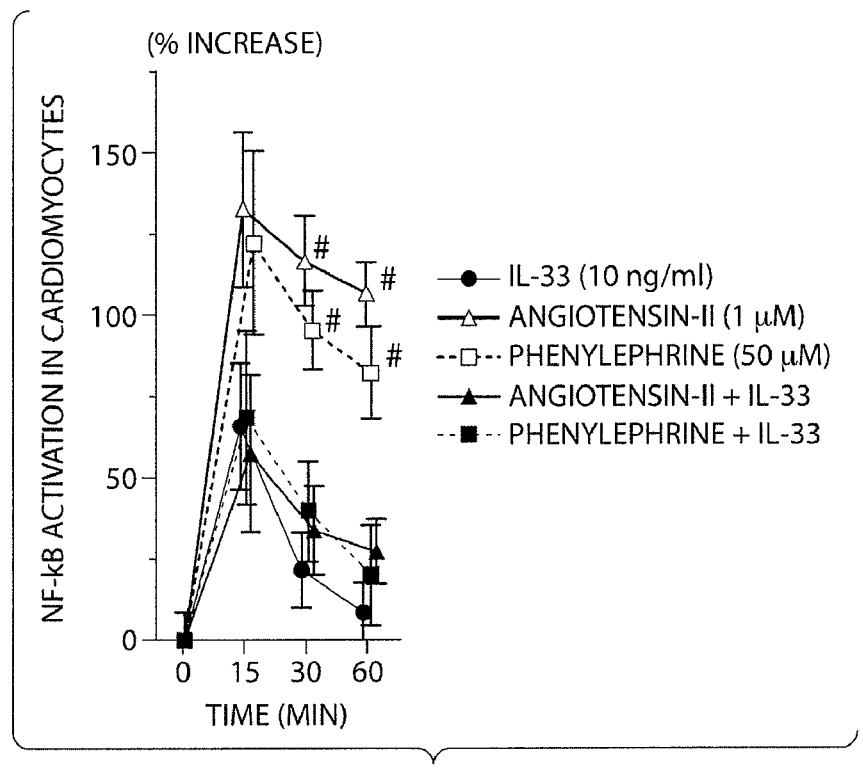
FIG. 13 shows that IL-33 transiently activates NF-κB but blocks NF-κB activation by hypertrophic stimuli. NF-κB nuclear binding activity was measured by EMSA in cardiomyocytes (FIG. 13A) and cardiac fibroblasts (FIG. 13B). IκBα phosphorylation was evaluated by Western analysis in cardiomyocytes (FIG. 13C) and cardiac fibroblasts (FIG. 13D). Each value was obtained as a ratio relative to control density, and is expressed as % increase compared with the control. Both angiotensin-II and phenylephrine significantly activated NF-κB. IL-33 also activated NF-κB, but IL-33 markedly attenuated angiotensin-II- or phenylephrine-induced NF-κB activation in cardiomyocytes, unlike in cardiac fibroblasts. IκBα phosphorylation was similarly affected by IL-33 treatment.
FIG. 13E shows that IL-33 (10 ng/ml) did not block IκBα phosphorylation (upper; Western analysis) and NF-κB activity (lower; EMSA) induced by PDGF-BB (10 ng/ml) or TNFα (10 ng/ml), unlike angiotensin-II or phenylephrine.
FIG. 13F provides results from a Western analysis for MAP kinases and Akt in cardiomyocytes. IL-33 (10 ng/ml) activated all MAP kinases, generally to a lesser extent compared with IL-1β (10 ng/ml). IL-33 attenuated angiotensin-II-induced phosphorylation of p38MAPK and JNK, but not ERK or Akt. Data are from 4-5 sets of experiments. GPCR agonists-induced ROS generation measured by 2,7-dichlorodihydrofluorecein diacetate (DCFDA) in cardiomyocytes (FIG. 13G) and cardiac fibroblasts (FIG. 13H). Both angiotensin-II and phenylephrine significantly induced ROS generation, and this was inhibited by IL-33 in cardiomyocytes. These data suggest that IL-33 can inhibit ROS-dependent hypertrophic signals. *:$p<0.05$ vs. baseline and #:$p<0.05$ vs. the same treatment group with IL-33.
Figure 13B:
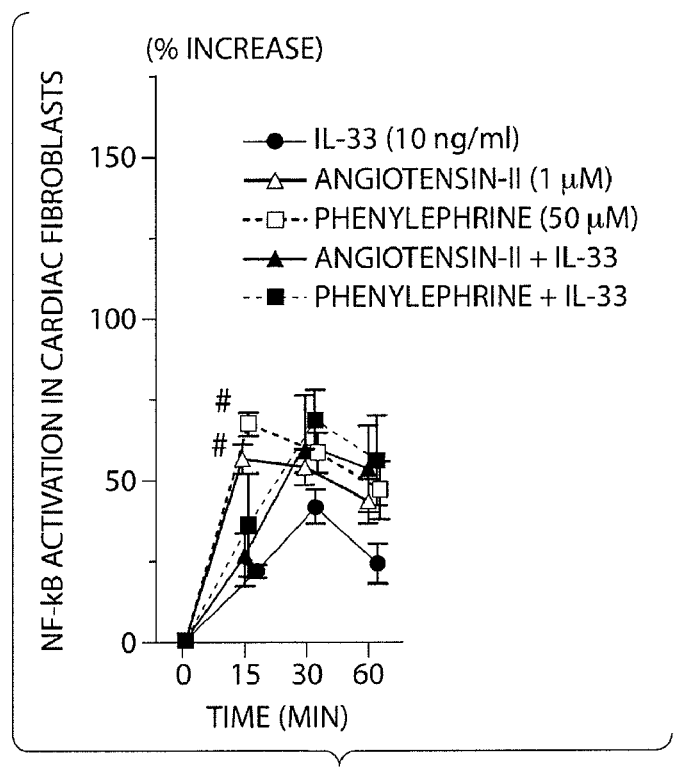
Figure 13C:
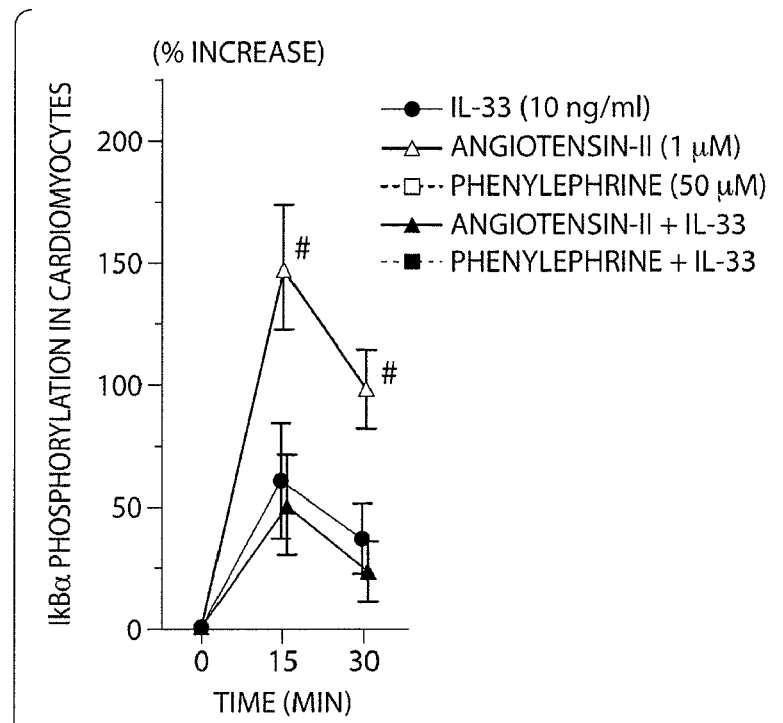
Figure 13D:
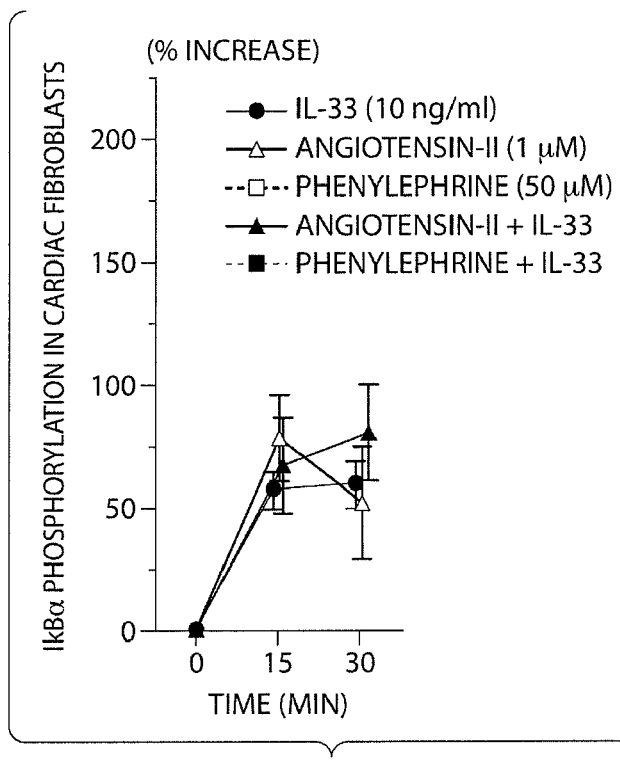
Figure 13E:
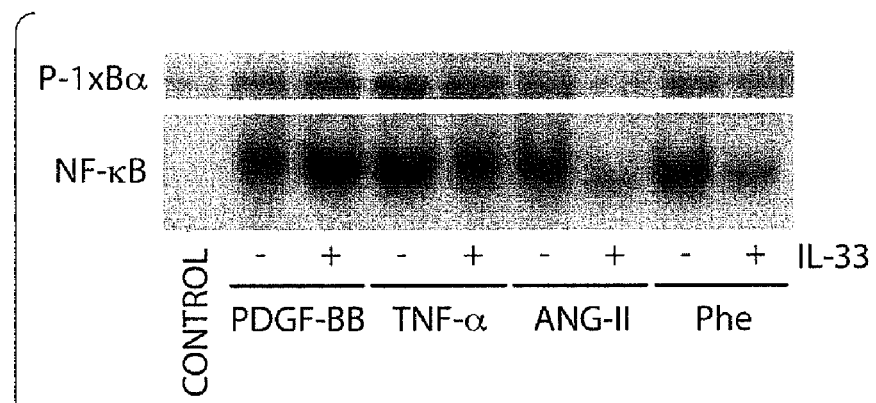

NF-κB is a signaling pathway common to Toll/IL-1 receptors including IL-33/ST2 (12), and NF-κB plays a role in cardiac hypertrophy (16). The role of NF-κB activation in the antihypertrophic effect of IL-33 was explored. Quantitative analyses from 5 separate experiments in cardiomyocytes (FIG. 13A) and cardiac fibroblasts (FIG. 13B) with or without angiotensin-II (1 μM), phenylephrine (50 μM) or IL-33 (10 ng/ml) confirmed that IL-33, angiotensin-II and phenylephrine independently activated NF-κB in both cell types. However, the activation of NF-κB by either angiotensin-II or phenylephrine in cardiomyocytes was attenuated by IL-33; this effect was only transiently observed in cardiac fibroblasts. As shown by quantitative analyses from 4 separate experiments in cardiomyocytes (FIG. 13C) and cardiac fibroblasts (FIG. 13D), angiotensin-II or IL-33 induced IκBα phosphorylation in both cell types, but IL-33 reduced IκB phosphorylation in cardiomyocytes, consistent with the electrophoretic mobility shift assays. Transient transfection reporter assays (n=3) also demonstrated that angiotensin-II increased NF-κB promoter activity (66+/−26%, p<0.05) and co-treatment with IL-33 abolished the induction of NF-κB promoter activity (8+/−12%, p=NS). Furthermore, co-treatment with sST2 released the repression of NF-κB promoter activity by IL-33 (42+/−5%, p<0.05). Interestingly, the reduction in both NF-κB nuclear binding activity and IκBα phosphorylation by IL-33 was not observed under stimulation by PDGF-BB (10 ng/ml) or TNF-α (10 ng/ml), which also activate NF-κB (FIG. 13E). These data demonstrate a dual nature of IL-33 signaling in cardiac myocytes, with mild activation of NF-κB but attenuation of NF-κB by other hypertrophic stimuli.

Figure 13F:
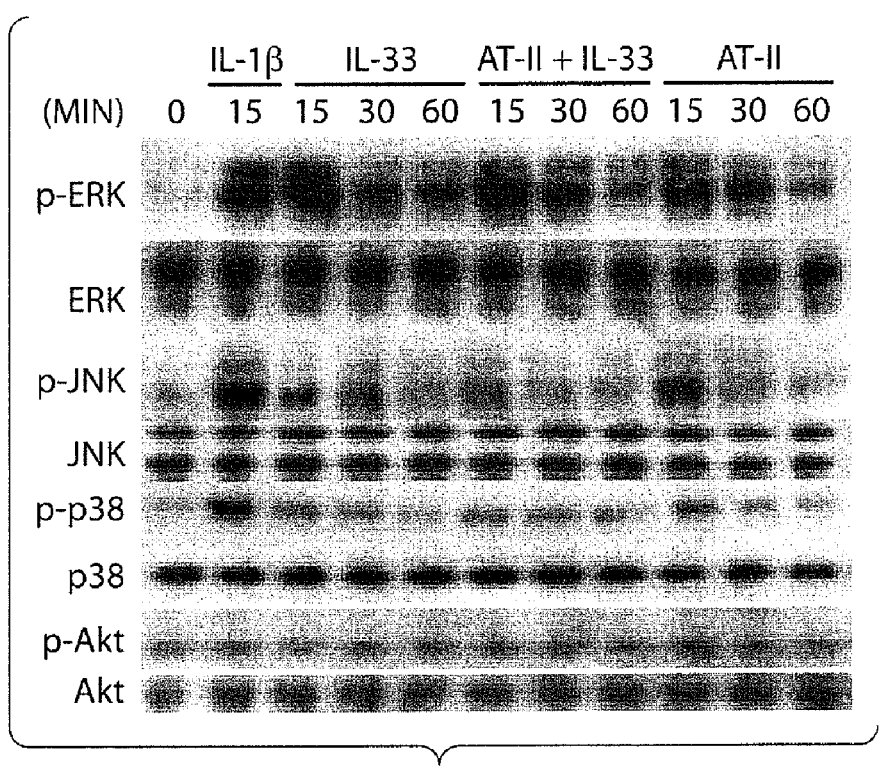

IL-33 can also activate MAPK pathways (14). In cardiomyocytes, IL-33 increased phosphorylation of ERK, p38 and JNK MAP kinases (FIG. 13F). IL-33-induced activation of MAPK pathways was generally modest compared with IL-1β in cardiomyocytes. Interestingly, co-treatment with IL-33 did not affect ERK phosphorylation, but decreased p38MAPK and JNK phosphorylation induced by angiotensin-II. IL-33 minimally activated Akt and did not impair angiotensin-II-induced Akt activation (FIG. 13F). These data suggest that IL-33 can have antihypertrophic properties through suppression of agonist-induced MAPK pathways, but the effects on MAP kinase signaling was less dramatic compared with the effects of IL-33 on NF-κB activation.

Figure 13G:
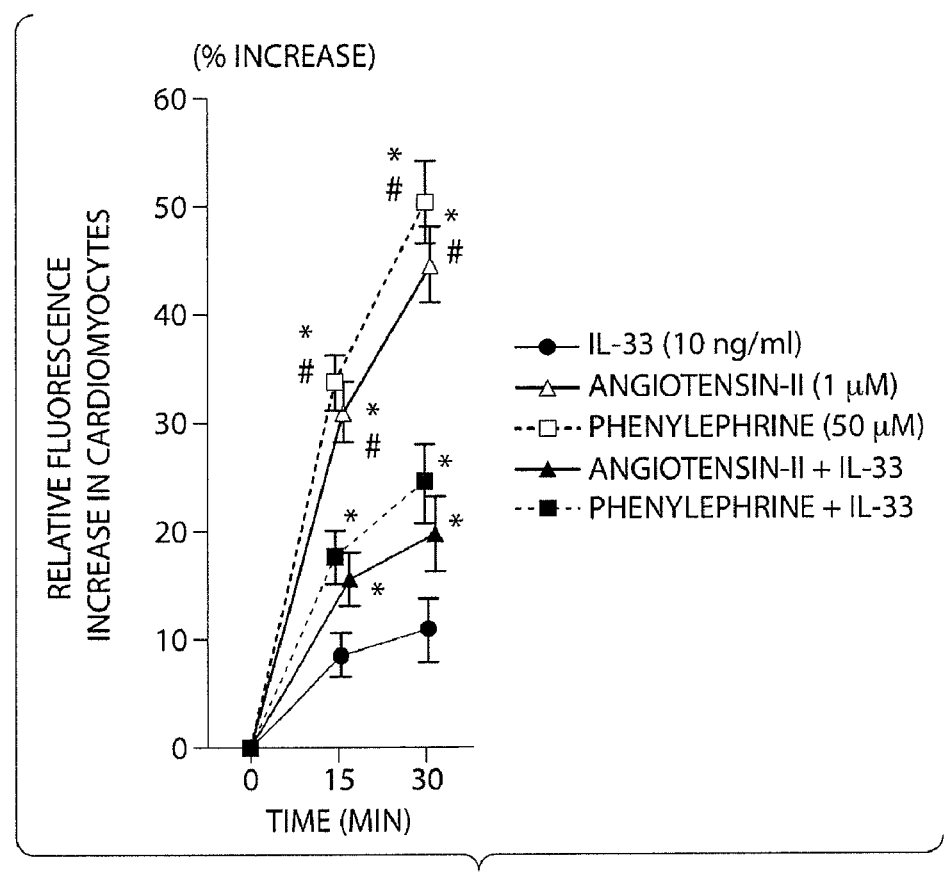
Figure 13H:
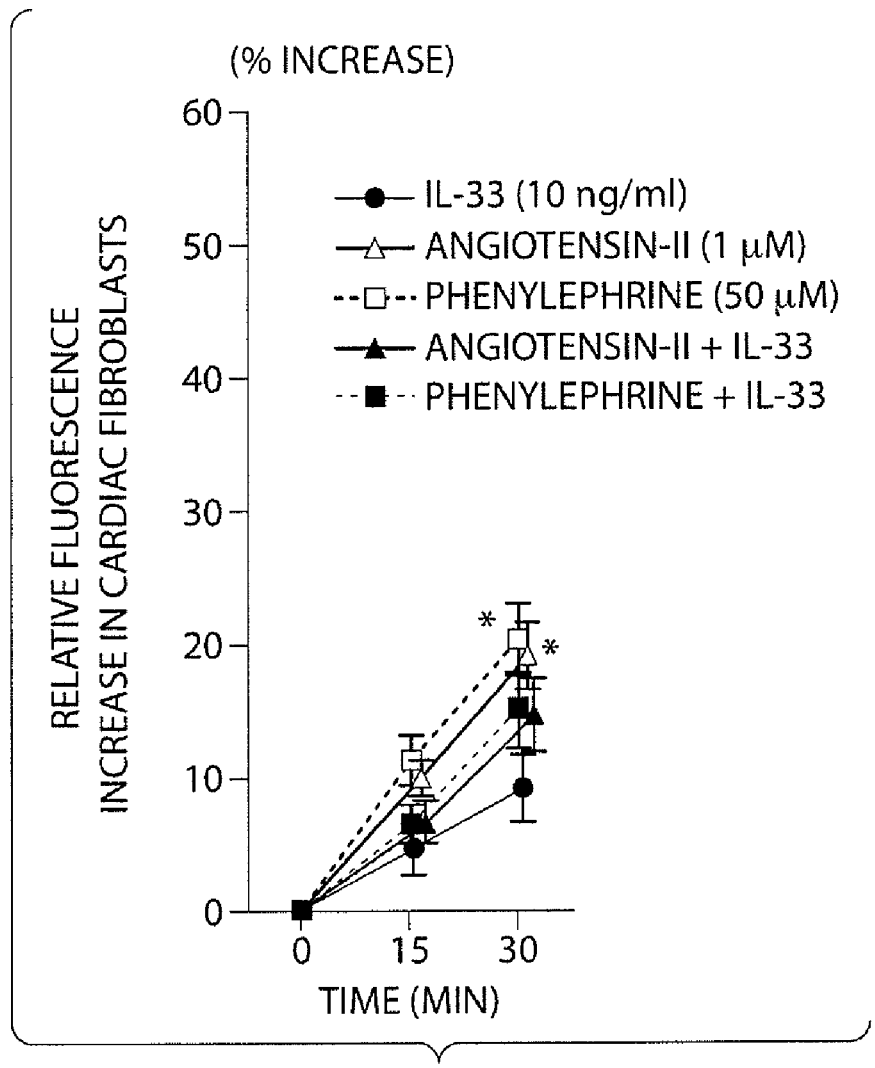

Because hypertrophic signals such as angiotensin-II can signal through the generation of reactive oxygen species (ROS) (17), experiments to determine if IL-33 regulated angiotensin-II-mediated ROS generation were also performed. As shown in FIGS. 13G and 13H, IL-33 significantly decreased the generation of ROS in the presence of angiotensin-II or phenylephrine.

ST2 Signaling is Cardioprotective In Vivo

The above experiments demonstrated that IL-33 is antihypertrophic in vitro and that sST2 can inhibit IL-33 signaling through ST2L. Human studies have demonstrated that increased sST2 is an adverse prognostic sign in cardiovascular disease (8, 9). To explore the hypothesis that IL-33 signaling through ST2L is cardioprotective in vivo, genotype-blinded TAC in mice with deletion of ST2 (ST2−/−) was performed vs. wild-type (WT) littermate controls. The ST2−/− mouse has deletion of most of exons 4 and 5 of the ST2 gene and thus lacks both ST2L as well as sST2; the mouse develops normally, although these mice are deficient in T helper cell type 2 cytokine responses (18).

Figure 14A:
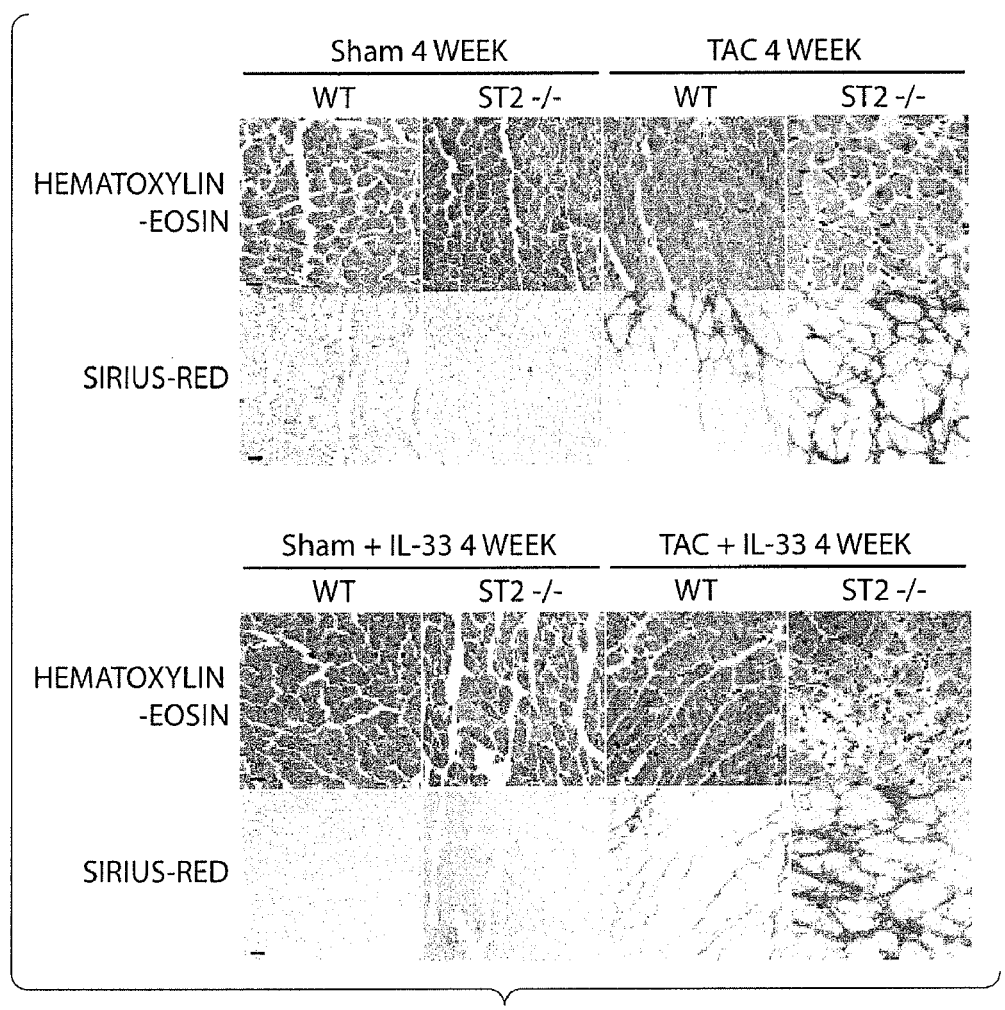
FIG. 14A provides representative Hematoxylin-Eosin stains and Sirius-red stains, and FIG. 14B provides results from quantitative analyses of samples from each group. A computer-based image analysis was used for measurements. ST2−/− mice developed more cardiomyocyte hypertrophy and cardiac fibrosis after TAC compared with WT mice. Furthermore, treatment with IL-33 (2 µg/day i.p.) significantly improved these changes in WT mice, but not in ST2−/− mice. The first left column represents the non-operated control group. Scale bar=10 µm. Gross measurement of heart weight normalized to body weight were consistent with the histomorphometric analyses (FIG. 14C). *:$p<0.05$ vs. non-operation control (FIG. 14B) or WT Sham (FIG. 14C), #:$p<0.05$. vs. the same treatment in WT, ¶:$p<0.05$ vs. Sham in the same group and $:$p<0.05$.
Figure 14B:
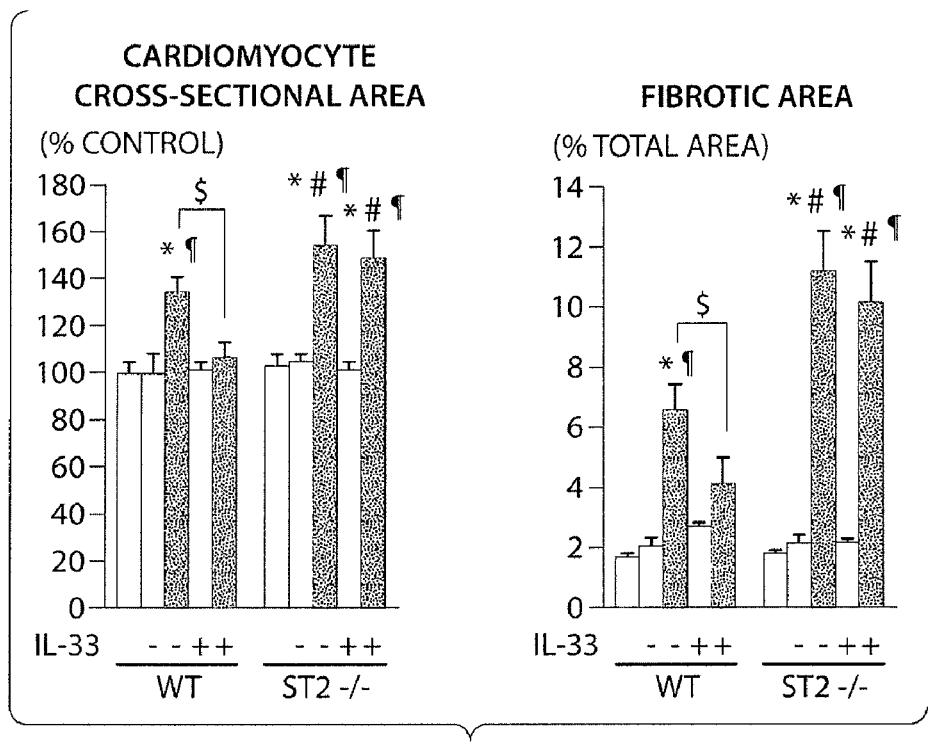
FIG. 14 illustrates that IL-33/ST2 signaling is cardioprotective in vivo.
Figure 14C:
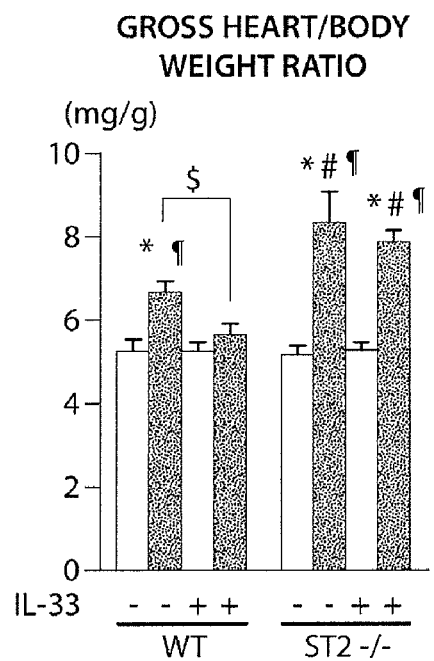

Histological studies (FIG. 14A) demonstrated increased cardiac fibrosis and increased cardiomyocyte cross-sectional area in ST2−/− mice after TAC (n=12) compared with WT littermates (n=10) (FIG. 14B). Furthermore, administration of purified IL-33 (2 μg/day i.p. for 4 weeks) reduced cardiac fibrosis and cardiomyocyte hypertrophy in WT mice, but not in ST2−/− littermates (since the IL-33 ligand should not affect mice without the ST2L receptor unless there is another unknown IL-33 receptor). Gross Heart/Body Weight measurements were consistent with histomorphometric data, revealing an antihypertrophic effect of IL-33 in WT mice but not in ST2−/− mice (FIG. 14C). In contrast, no change in any parameter was observed among non-operated control (n=7), Sham-operated WT (n=8) and Sham-operated ST2−/− (n=8) groups.

Figure 15A:
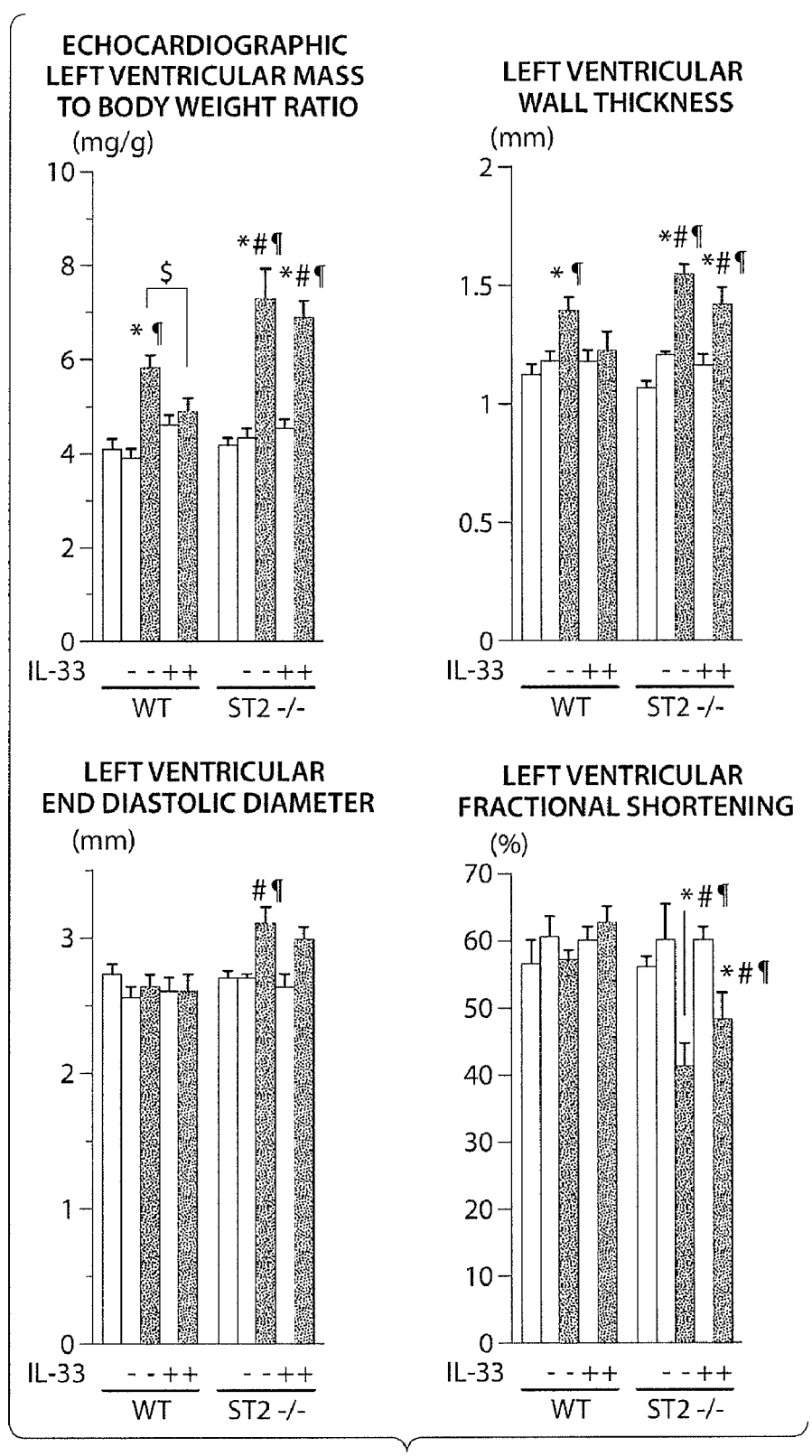
In FIG. 15A, the first left column represents the non-operated control group. *:$p<0.05$ vs. non-operation control (FIG. 15A) or WT Sham (FIG. 15C), #:$p<0.05$ vs. the same treatment in WT, ¶:$p<0.05$ vs. Sham in the same group and $:$p<0.05$.

A separate echocardiographic analysis (also genotype-blinded) was performed in these animals. These data demonstrated that deletion of ST2 leads to both increased hypertrophy and impaired systolic function following TAC (FIG. 15A). In addition, treatment with IL-33 reduced hypertrophy in WT mice, but not in ST2−/− littermates. Increased left ventricular dilation and reduced fractional shortening were observed only in ST2−/− mice after TAC, and these changes were not reversed by treatment with IL-33 in ST2−/− mice (FIG. 15A).

Figure 15B:
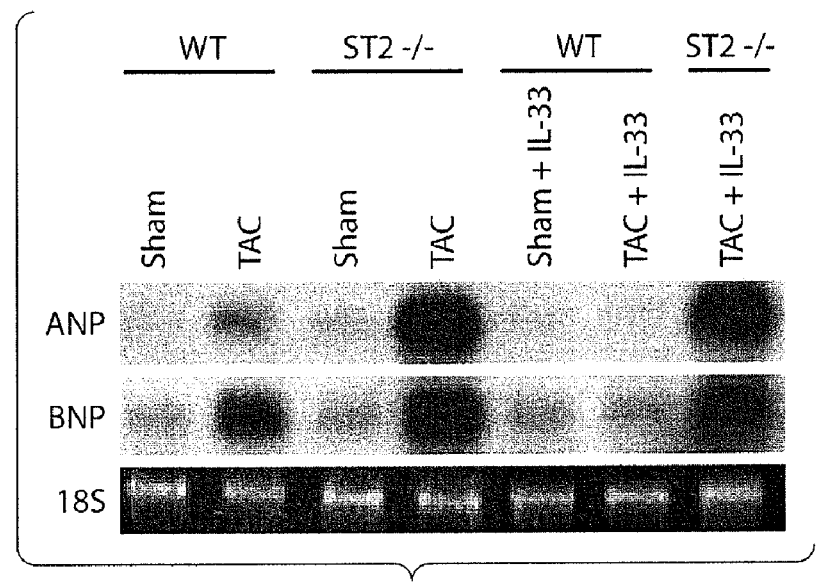
FIG. 15B provides representative images and FIG. 15C provides results from a quantitative analysis of mRNA expression of ANP and BNP relative to internal control (18S) in left ventricle at 1-week after operation by Northern analysis.
Figure 15C:
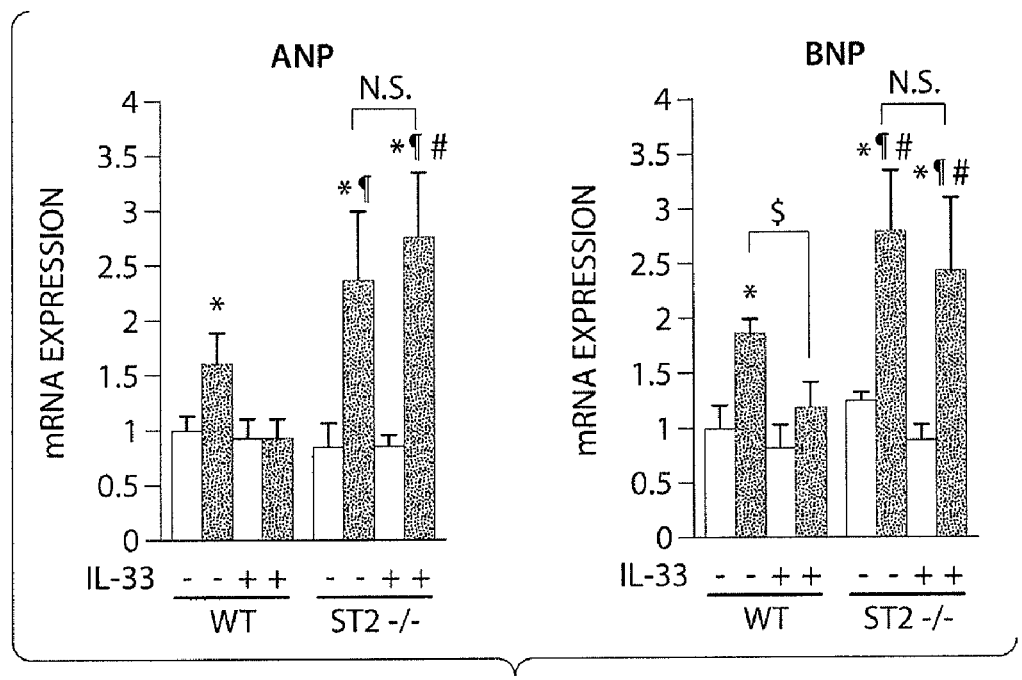
FIG. 15 illustrates that IL-33/ST2 signaling is cardioprotective in vivo. Echocardiographic analysis at 4-weeks after operation demonstrated increased left ventricular mass, left ventricular wall thickness and reduced fractional shortening in ST2−/− mice (FIG. 15A). Treatment with IL-33 reduced hypertrophy only in WT mice. IL-33 caused no significant change under non-stress conditions in vivo. N=indicated in text except N=10 each for non-operated controls.
FIG. 15D shows NF-κB activation from EMSA in vivo 1-week after operation. ANP and BNP expression and NF-κB activity increased in ST2−/− mice compared with WT mice, and IL-33 reversed these changes only in WT mice. Open and closed bars indicate Sham-operated and TAC-operated groups, respectively.
Figure 15D:
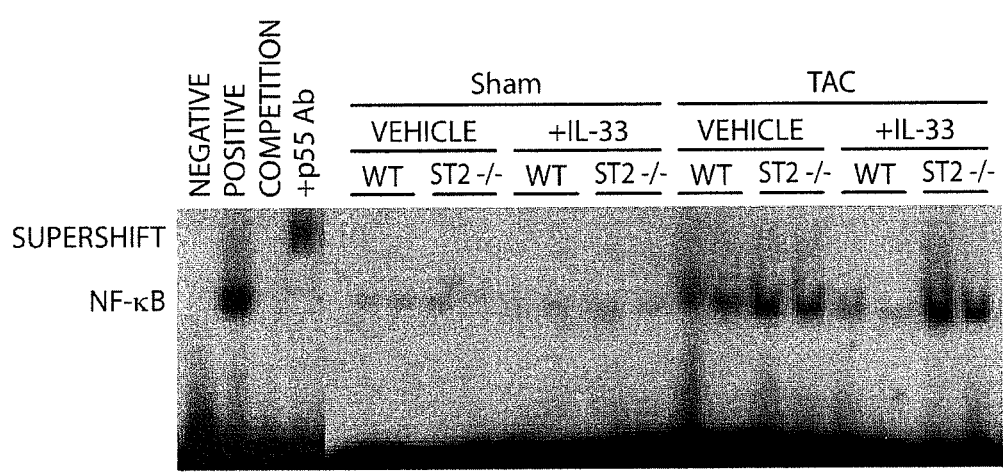
Figure 16A:
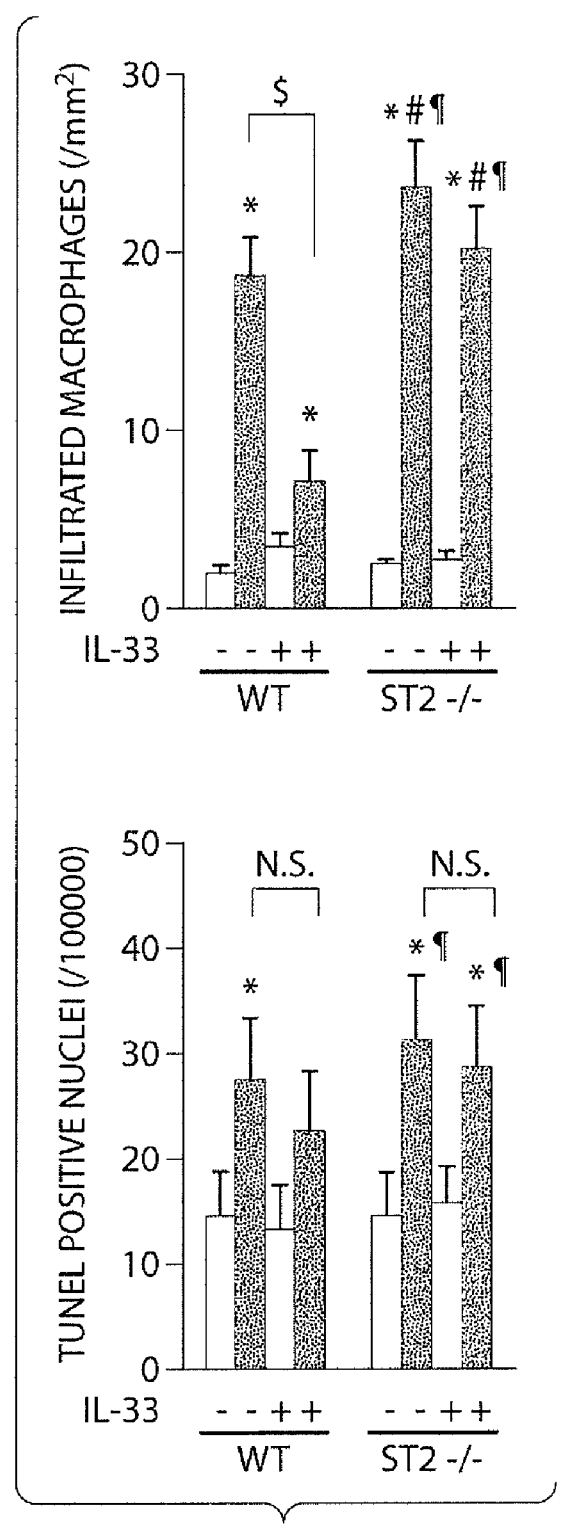
FIG. 16A provides results from a quantitative analysis of macrophages (upper) and TUNEL stain-positive nuclei (lower). A computer-based image analysis was used. TAC increased macrophage infiltration after 1-week of operation. IL-33 alone did not induce macrophage infiltration in either WT or ST2−/− mice but co-treatment reduced macrophage infiltration after TAC only in WT mice. TAC approximately doubled the number of TUNEL positive nuclei after 4 weeks in both WT and ST2−/− mice. IL-33 treatment did not affect TUNEL positivity. *:$p<0.05$ vs. WT Sham, #:$p<0.05$. vs. the same treatment in WT, ¶:$p<0.05$ vs. Sham in the same group and $:$p<0.05$. A Kaplan-Meier survival curve analysis revealed that the survival of ST2−/− mice under TAC was significantly reduced compared with that of WT mice (FIG. 16B). This experiment was blinded so that all procedures were performed without knowledge of mouse genotype. Serial echocardiographic analysis of surviving mice revealed that ST2−/− mice had increased left ventricular mass, left ventricular wall thickness and reduced contractile function compared with WT mice (FIG. 16C). *:$p<0.05$ vs. baseline, #:$p<0.05$. vs. the same treatment in WT, ¶:$p<0.05$ vs. the same group without IL-33 treatment.

Following TAC, ST2−/− mice had increased gene expression of atrial and B-type natriuretic peptides (ANP and BNP) (FIGS. 15B and 15C), genes commonly induced by hypertrophic stimuli. Treatment with IL-33 markedly attenuated induction of both genes in WT but not in ST2−/− mice. Quantitative gene expression analysis confirmed that deletion of ST2 signaling enhanced the induction of BNP by TAC and that treatment with IL-33 effectively reversed the induction of these hypertrophic genes in WT mice with TAC, but not in ST2−/− mice (FIG. 15C). Consistent with in vitro experiments described above, TAC-enhanced NF-κB nuclear binding activity was prominently observed in left ventricular myocardium of both WT mice and ST2−/− littermates. IL-33 inhibited NF-κB induction only in WT mice and not in ST2−/− mice (FIG. 15D). Reports showed regional myocardial infiltration of inflammatory cells in experimental studies with mice under pressure overload (19, 20); macrophage infiltration within myocardium after 1-week of treatment in both phenotypes was evaluated. As shown in FIG. 16A, IL-33 did not significantly increase macrophage infiltration in either WT or ST2−/− mice, including perivascular regions. However, mice with TAC showed significant increases in macrophage infiltration and this infiltration was decreased by co-treatment with IL-33 in WT mice. Furthermore, to investigate the mechanism of cardiac histological and functional changes, the presence of apoptosis within myocardium after 4-week of operation with or without IL-33 treatment was evaluated. There was an increase in the percentage of TUNEL positive stained nuclei in mice that underwent TAC (FIG. 16A), as reported (21, 22). The percentage of TUNEL positive cells was not changed by treatment with IL-33 or by genetic deletion of ST2 (FIG. 16A). These data suggest that changes in apoptosis do not directly cause the changes in cardiac fibrosis.

Figure 16B:
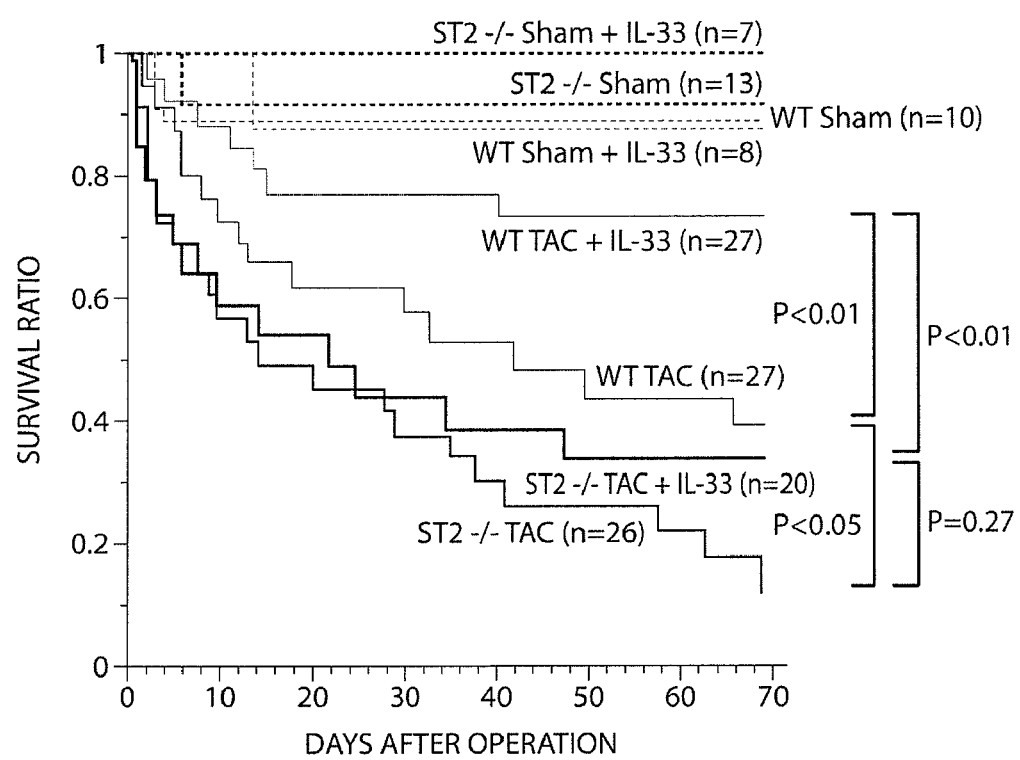
FIG. 16 shows that IL-33 improves survival after TAC and reduces TAC-induced macrophage infiltration but not apoptosis. Transverse Aortic Constriction (TAC) was performed on littermates using mice with genetic deletion of ST2 vs. WT.
Figure 16C:
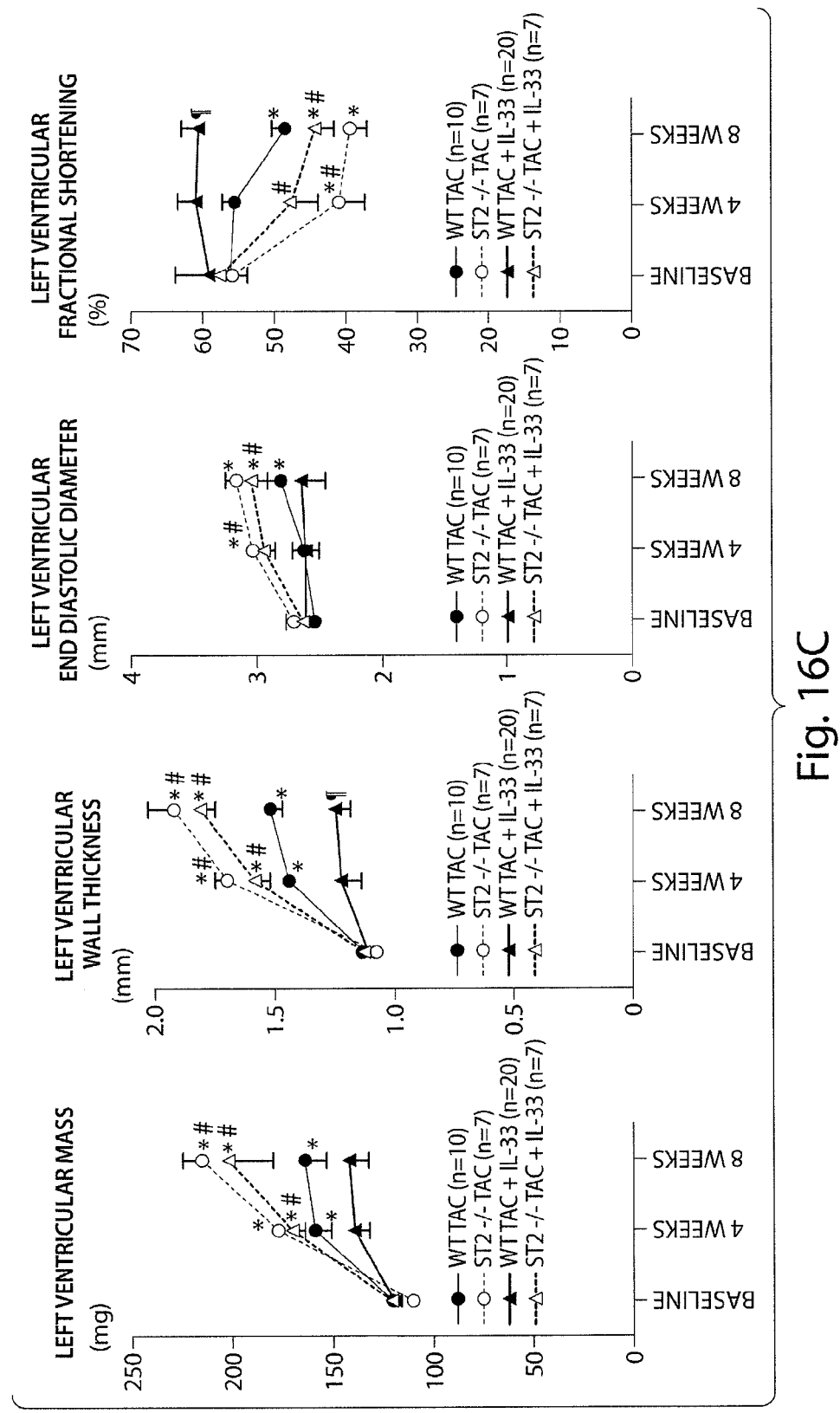

In a separate blinded and randomized experiment, the role of IL-33/ST2 signaling in mortality after TAC was studied. Deletion of ST2 increased mortality after TAC (n=26) compared with WT littermates (n=27) (FIG. 16B). Furthermore, IL-33 significantly improved survival in WT mice after TAC (n=27), but not in ST2−/− littermates (n=20). Echocardiographic studies were also performed on each mouse, and these data on mice that survived for 8 weeks after TAC indicated that ST2−/− mice (n=10) had a greater increase in left ventricular mass, wall thickness and ventricular chamber size as well as impaired contractile function compared with WT littermates (n=7) (FIG. 16C). IL-33 treatment reduced wall thickness and increased fractional shortening in WT mice (n=20), but not in ST2−/− littermates (n=7) (FIG. 16C). In this experiment, all deaths were spontaneous, and no mouse required euthanasia due to signs of discomfort as determined by veterinary staff.

Figure 17:
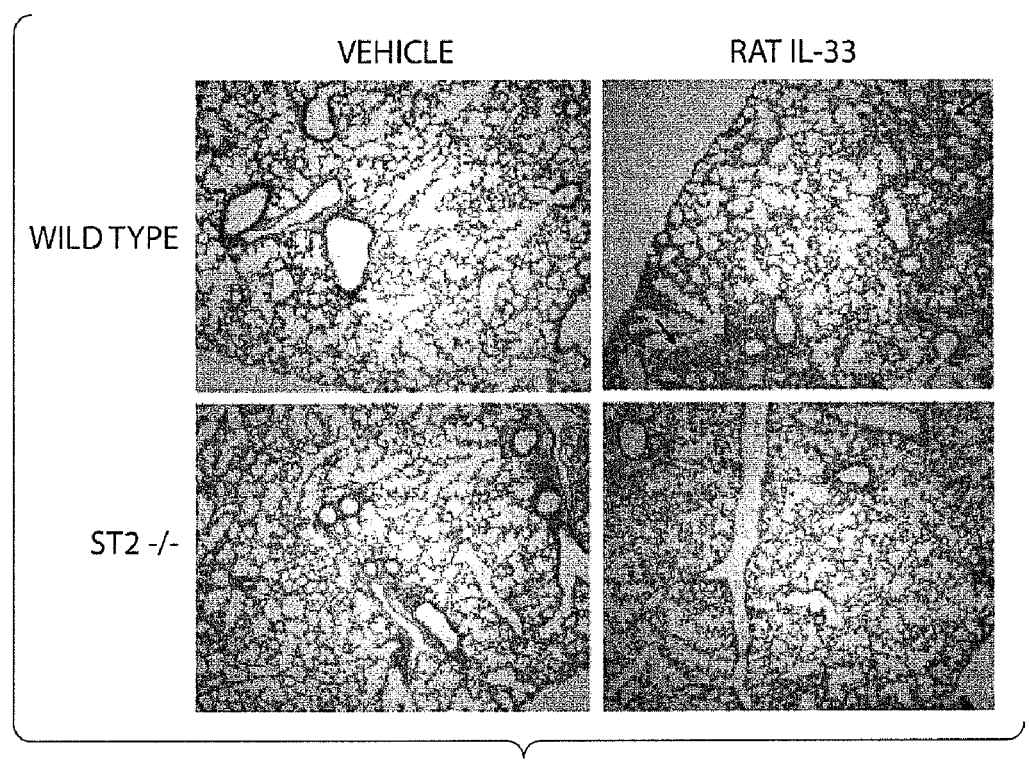
FIG. 17 shows that IL-33 treatment causes focal pulmonary inflammation. Representative specimens of lung (Hematoxylin-Eosin stain, ×100) from mice 1 week after sham-operation with or without 7-day treatment with 2 µg/day rat IL-33. In the pulmonary parenchyma of WT mice, IL-33 treatment (top right) led to mild focal infiltrations of inflammatory cells (arrows) within and adjacent to vessels. This was not seen in vehicle-treated mice (top left). These changes were not observed in ST2–/– mice with (bottom right) or without (bottom left) IL-33 treatment.

Finally, inflammatory effects of recombinant IL-33 was shown, histological changes in lungs from Sham-operated mice that underwent recombinant IL-33 treatment were studied. Mild infiltration of inflammatory cells within vessel walls and adjacent to the vessels was observed in the lungs of WT mice with 2 µg/day rat IL-33 treatment for 7 days compared with vehicle-treated mice (FIG. 17). The inflammatory changes were more focal compared to those described (12). Furthermore, the epithelial lining of the airways remained unchanged. None of these changes were observed in ST2−/− mice either with or without IL-33 treatment (FIG. 7), suggesting that the mild pulmonary inflammation is due to IL-33/ST2 signaling.

Discussion

Although ST2 is a biomarker in heart diseases such as heart failure (8) and myocardial infarction (9), the pathophysiological role of ST2 in the myocardium has been unclear, partly due to the lack of a known ligand for ST2. Using a structural bioinformatics approach, a novel IL-1-related sequence from a dog brain library was identified (12). This protein (IL-33) proved to be a functional ligand of ST2L capable of activating NF-κB, the common signaling pathway of Toll/IL-1 receptors (12). Here it is shown that the ligand IL-33 is synthesized by cardiac fibroblasts and abrogates angiotensin-II- and phenylephrine-induced hypertrophy in cardiomyocytes in vitro. Furthermore, targeted deletion of ST2 in mice enhanced cardiac hypertrophy and fibrosis following mechanical overload, accompanied by impaired contractility and survival, while administration of purified recombinant IL-33 improved pathological changes and survival in WT mice, but not in ST2−/− mice. Therefore, these data demonstrate that IL-33/ST2 signaling protects the myocardium under mechanical overload.

IL-1R/TLR superfamily receptors share similar downstream signaling pathways (23), including binding with adaptor proteins such as myeloid differentiation primary-response protein-88 (MyD88) or its variant Mal, recruiting TNF receptor-associated factor-6 (TRAF-6), activating apoptosis signal-regulated kinase-1 (MEKKK to activate p38MAPK) (24) and NF-κB-inducing kinase-1 (NIK-1; to activate I-κB kinases) (25) as well as TGF-β-activated kinase-1 (TAK-1), leading to activation of p38MAPK (26), JNK (25) or NF-κB (25, 26). NF-κB plays a pivotal role in cardiomyocyte hypertrophy in vitro (27, 28) and in vivo (28, 29), and the activation of NF-κB under both basal and stimulated conditions was studied. IL-33 mildly activated NF-κB in basal conditions, but IL-33 markedly attenuated angiotensin-II or phenylephrine-induced NF-κB activation in cardiac myocytes.

Regulation of NF-κB activation may explain the antihypertrophic effect of IL-33. The mechanisms by which IL-33 may dampen NF-κB activation are unclear. The experiments suggest that IL-33 can suppress ROS generation by angiotensin-II or phenylephrine, and ROS generation has been implicated in NF-κB activation (17). Alternatively, feedback inhibition (30) and oscillation (31) are commonly found with NF-κB activation, so that other mechanisms for the IL-33 antihypertrophic effect are also plausible. Angiotensin-II (28, 32) as well as other GPCR ligands (33) promote cardiac hypertrophy induced by mechanical pressure overload (26, 28, 29, 32, 34). Interestingly, evidence suggests a relationship between GPCR (especially angiotensin-II)-induced and IL-1R/TLR superfamily-induced signals in activating NF-κB and MAPKs in cardiomyocytes. For example, the small GTPase Rac-1 (35, 36), which is translocated to the cytoplasmic membrane and activated through angiotensin-II receptors (35), subsequently activates NADPH oxidases that produce ROS (36) that regulate further downstream kinases. Li et al. (37) reported that Rac-1 facilitates the recruitment of NADPH oxidases into active endosomal MyD88/IL-1R1 complexes and subsequent redox-dependent recruitment of TRAF6 to the MyD88/IL-1R1 complex. Furthermore, depletion of TLR-4 (29) or inactivation of MyD88 (34) decreases cardiac hypertrophy induced by TAC.

Using a higher dose and also a more prolonged dosing protocol, reduced pulmonary inflammation was observed compared with the description of IL-33 by Schmitz et al. (12). While IL-33 has pro-inflammatory effects in the lung, increased macrophage or eosinophil infiltration in myocardium after IL-33 treatment was not observed. However, IL-33 reduced macrophage infiltration after TAC in WT mice, suggesting that IL-33 may be anti-inflammatory and anti-fibrotic in myocardium through a primary effect on cardiomyocytes or other cardiac cells. In the study, purified mature rat IL-33 protein was used in mice, while the other study used the recombinant human protein in mice. The mature mouse IL-33 amino acid sequence (GenBank™ accession number AY905582) is 90% identical to rat IL-33 (GenBank™ accession number BC081993), but only 57% identical to human IL-33 (GenBank™ accession number AY905581), so differences in inflammation may also be due to differences between the human and rat IL-33 proteins or differences in the preparations. Furthermore, genetic background of mice could affect these results.

Fibrosis is a hallmark of long-standing myocardial overload. Recent reports suggest that cardiac fibrosis might be regulated by signaling upstream of NF-κB (such as TAK-1) in cardiac myocytes (26, 34) or by cross-talk with cardiac myocytes through cytokines (38). Patients with increased sST2 appear to be inhibiting endogenous IL-33/ST2 cardioprotection through the binding of myocardial IL-33 to sST2, thereby preventing signaling through ST2L. There was a trend toward increased amino acid uptake due to sST2 in cardiomyocytes also treated with angiotensin II or phenylephrine. This could be due to a direct effect of sST2, as has been suggested (39). Alternatively, in these experiments, it could be due to reduced endogenous IL-33 signaling due to sST2. Although cardiomyocytes appear to synthesize less IL-33 compared with cardiac fibroblasts, it is possible that endogenous IL-33 suppresses angiotensin-II- or phenylephrine-induced amino acid uptake. This concept is supported by the trend toward increasing leucine uptake by the anti-ST2 antibody in the presence of angiotensin-II. In addition, it was observed that PMA caused a dose-dependent robust induction in both sST2 and IL-33 protein expression, with a dose-dependent decrease in free IL-33 level. This further supports the concept of sST2-bound sequestration of IL-33 decreases physiological activity of IL-33 on cells through a "decoy" action of sST2. Although the data are consistent with cardioprotective IL-33 signaling, and inhibition of cardioprotection by sST2 as a decoy receptor. It is also possible that sST2 may serve as a reservoir for IL-33. Such a scenario was described for soluble IL-6 receptor (40). Thus, sST2 may function as more than an inhibitor of ST2L signaling. A detailed characterization of the relative binding affinities of native sST2 and ST2L for IL-33 will further the understanding of the role of specific levels of sST2 as a decoy receptor. Soluble interleukin receptors can have substantially lower affinity to the same ligand compared with membrane-bound isoforms (41), and thus excess of sST2 may be necessary to inhibit IL-33 signaling through ST2L.

There was a modest increase in NF-κB binding in the ventricles of ST2−/− mice treated with IL-33. Although the data support no effect of IL-33 in the absence of ST2, there is the possibility that there is another function of IL-33 other than binding to ST2. Finally, sST2 appears to be not only a biomarker for poor outcome, but also a true pathophysiological mediator of disease progression.

References for Example 2

1. Sadoshima, J., and Izumo, S. 1997. The cellular and molecular response of cardiac myocytes to mechanical stress. *Annu Rev Physiol* 59:551-571.
2. McKinsey, T. A., and Olson, E. N. 2005. Toward transcriptional therapies for the failing heart: chemical screens to modulate genes. *J Clin Invest*. 115:538-546.
3. Diez, J., Gonzalez, A., Lopez, B., and Querejeta, R. 2005. Mechanisms of disease: pathologic structural remodeling is more than adaptive hypertrophy in hypertensive heart disease. *Nat Clin Pract Cardiovasc Med*. 2:209-216.
4. Baudino, T., Carver, W., Giles, W. R., and Borg, T. K. 2006. Cardiac Fibroblasts: friend or foe? *Am J Physiol Heart Circ Physiol*. 291:H1015-1026.
5. Grossman, W., Jones, D., and McLaurin, L. P. 1975. Wall stress and patterns of hypertrophy in the human left ventricle. *J Clin Invest* 56:56-64.
6. Weinberg, E. O., Shimpo, M., De Keulenaer, G. W., MacGillivray, C., Tominaga, S., Solomon, S. D., Rouleau, J. L., and Lee, R. T. 2002. Expression and regulation of ST2, an interleukin-1 receptor family member, in cardiomyocytes and myocardial infarction. *Circulation* 106:2961-2966.
7. Iwahana, H., Yanagisawa, K., Ito-Kosaka, A., Kuroiwa, K., Tago, K., Komatsu, N., Katashima, R., Itakura, M., and Tominaga, S. 1999. Different promoter usage and multiple transcription initiation sites of the interleukin-1-receptor-related human ST2 gene in UT-7 and TM12 cells. *Eur J Biochem* 264:397-406.
8. Weinberg, E. O., Shimpo, M., Hurwitz, S., Tominaga, S., Rouleau, J. L., and Lee, R. T. 2003. Identification of serum soluble ST2 receptor as a novel heart failure biomarker. *Circulation* 107:721-726.
9. Shimpo, M., Morrow, D. A., Weinberg, E. O., Sabatine, M. S., Murphy, S. A., Antman, E. M., and Lee, R. T. 2004. Serum levels of the interleukin-1 receptor family member ST2 predict mortality and clinical outcome in acute myocardial infarction. *Circulation* 109:2186-2190.
10. Kumar, S., Minnich, M. D., and Young, P. R. 1995. ST2/T1 protein functionally binds to two secreted proteins from Balb/c 3T3 and human umbilical vein endothelial cells but does not bind interleukin 1. *J Biol Chem* 270:27905-27913.
11. Gayle, M. A., Slack, J. L., Bonnert, T. P., Renshaw, B. R., Sonoda, G., Taguchi, T., Testa, J. R., Dower, S. K., and Sims, J. E. 1996. Cloning of a putative ligand for the T1/ST2 receptor. *J Biol Chem* 271:5784-5789.
12. Schmitz, J., Owyang, A., Oldham, E., Song, Y., Murphy, E., McClanahan, T. K., Zurawski, G., Moshrefi, M., Qin, J., Li, X., et al. 2005. IL-33, an interleukin-1-like cytokine that signals via the IL-1 receptor-related protein ST2 and induces T helper type 2-associated cytokines. *Immunity* 23:479-490.
13. Manabe, I., Shindo, T., and Nagai, R. 2002. Gene expression in fibroblasts and fibrosis: involvement in cardiac hypertrophy. *Circ Res*. 91:1103-1113.
14. Marian, A. J. 2000. Pathogenesis of diverse clinical and pathological phenotypes in hypertrophic cardiomyopathy. *Lancet* 355:58-60.
15. Goldsmith, E. C., Hoffman, A., Morales, M. O., Potts, J. D., Price, R. L., McFadden, A., Rice, M., and Borg, T. K. 2004. Organization of fibroblasts in the heart. *Dev Dyn*. 230:787-794.
16. Kawano, S., Kubota, T., Monden, Y., Kawamura, N., Tsutsui, H., Takeshita, A., and Sunagawa, K. 2005. Blockade of NF-kappaB ameliorates myocardial hypertrophy in response to chronic infusion of angiotensin II. *Cardiovasc Res* 67:689-698.
17. Hirotani, S., Otsu, K., Nishida, K., Higuchi, Y., Morita, T., Nakayama, H., Yamaguchi, O., Mano, T., Matsumura, Y., Ueno, H., et al. 2002. Involvement of nuclear factor-kappaB and apoptosis signal-regulating kinase 1 in G-protein-coupled receptor agonist-induced cardiomyocyte hypertrophy. *Circulation*. 105:509-515.
18. Townsend, M. J., Fallon, P. G., Matthews, D. J., Jolin, H. E., and McKenzie, A. N. 2000. T1/ST2-deficient mice demonstrate the importance of T1/ST2 in developing primary T helper cell type 2 responses. *J Exp Med* 191:1069-1076.
19. Kuster, G. M., Kotlyar, E., Rude, M. K., Siwik, D. A., Liao, R., Colucci, W. S., and Sam, F. 2005. Mineralocorticoid receptor inhibition ameliorates the transition to myocardial failure and decreases oxidative stress and inflammation in mice with chronic pressure overload. *Circulation* 111:420-427.
20. Shioi, T., Matsumori, A., Kihara, Y., Inoko, M., Ono, K., Iwanaga, Y., Yamada, T., Iwasaki, A., Matsushima, K., and Sasayama, S. 1997. Increased expression of interleukin-1 beta and monocyte chemotactic and activating factor/monocyte chemoattractant protein-1 in the hypertrophied and failing heart with pressure overload. *Circ Res*. 81:664-671.
21. Okada, K., Minamino, T., Tsukamoto, Y., Liao, Y., Tsukamoto, O., Takashima, S., Hirata, A., Fujita, M., Nagamachi, Y., Nakatani, T., et al. 2004. Prolonged endoplasmic reticulum stress in hypertrophic and failing heart after aortic constriction: possible contribution of endoplasmic reticulum stress to cardiac myocyte apoptosis. *Circulation* 110:705-712.
22. Yang, G., Meguro, T., Hong, C., Asai, K., Takagi, G., Karoor, V. L., Sadoshima, J., Vatner, D. E., Bishop, S. P., and Vatner, S. F. 2001. Cyclosporine reduces left ventricular mass with chronic aortic banding in mice, which could be due to apoptosis and fibrosis. *J Mol Cell Cardiol*. 33:1505-1514.
23. Dunne, A., and O'Neill, L. A. 2003. The interleukin-1 receptor/Toll-like receptor superfamily: signal transduction during inflammation and host defense. *Sci STKE* 2003:re3.
24. Matsuzawa, A., Saegusa, K., Noguchi, T., Sadamitsu, C., Nishitoh, H., Nagai, S., Koyasu, S., Matsumoto, K., Takeda, K., and Ichijo, H. 2005. ROS-dependent activation of the TRAF6-ASK1-p38 pathway is selectively required for TLR4-mediated innate immunity. *Nat Immunol*. 6:587-592.
25. Ninomiya-Tsuji, J., Kishimoto, K., Hiyama, A., Inoue, J., Cao, Z., and Matsumoto, K. 1999. The kinase TAK1 can activate the NIK-I kappaB as well as the MAP kinase cascade in the IL-1 signalling pathway. *Nature* 398:252-256.
26. Zhang, D., Gaussin, V., Taffet, G. E., Belaguli, N. S., Yamada, M., Schwartz, R. J., Michael, L. H., Overbeek, P. A., and Schneider, M. D. 2000. TAK1 is activated in the myocardium after pressure overload and is sufficient to provoke heart failure in transgenic mice. Nat Med. 6:556-563.

27. Purcell, N. H., Tang, G., Yu, C., Mercurio, F., DiDonato, J. A., and Lin, A. 2001. Activation of NF-kappa B is required for hypertrophic growth of primary rat neonatal ventricular cardiomyocytes. *Proc Natl Acad Sci USA* 98:6668-6673.
28. Freund, C., Schmidt-Ullrich, R., Baurand, A., Dunger, S., Schneider, W., Loser, P., El-Jamali, A., Dietz, R., Scheidereit, C., and Bergmann, M. W. 2005. Requirement of nuclear factor-kappaB in angiotensin II- and isoproterenol-induced cardiac hypertrophy in vivo. *Circulation* 111:2319-2325.
29. Ha, T., Li, Y., Hua, F., Ma, J., Gao, X., Kelley, J., Zhao, A., Haddad, G. E., Williams, D. L., Browder, I. W., et al. 2005. Reduced cardiac hypertrophy in toll-like receptor 4-deficient mice following pressure overload. *Cardiovasc Res.* 68:224-234.
30. Hoffmann, A., and Baltimore, D. 2006. Circuitry of nuclear factor kappaB signaling. *Immunol Rev* 210:171-186.
31. Nelson, D. E., Ihekwaba, A. E., Elliott, M., Johnson, J. R., Gibney, C. A., Foreman, B. E., Nelson, G., See, V., Horton, C. A., Spiller, D. G., et al. 2004. Oscillations in NF-kappaB signaling control the dynamics of gene expression. *Science* 306:704-708.
32. Rockman, H. A., Wachhorst, S. P., Mao, L., and Ross, J. J. 1994. ANG II receptor blockade prevents ventricular hypertrophy and ANF gene expression with pressure overload in mice. *Am J Physiol.* 266:H2468-2475.
33. Rapacciuolo, A., Esposito, G., Caron, K., Mao, L., Thomas, S. A., and Rockman, H. A. 2001. Important role of endogenous norepinephrine and epinephrine in the development of in vivo pressure-overload cardiac hypertrophy. *J Am Coll Cardiol.* 38:876-882.
34. Ha, T., Hua, F., Li, Y., Ma, J., Gao, X., Kelley, J., Zhao, A., Haddad, G. E., Williams, D. L., Browder, I. W., et al. 2006. Blockade of MyD88 attenuates cardiac hypertrophy and decreases cardiac myocyte apoptosis in pressure overload-induced cardiac hypertrophy in vivo. *Am J Physiol Heart Circ Physiol.* 290:H985-994.
35. Hingtgen, S. D., Tian, X., Yang, J., Dunlay, S. M., Peek, A. S., Wu, Y., Sharma, R. V., Engelhardt, J. F., and Davisson, R. L. 2006. Nox2-Containing NADPH Oxidase and Akt Activation Play a Key Role in Angiotensin II-Induced Cardiomyocyte Hypertrophy. *Physiol Genomics.* 26:180-191.
36. Nishida, M., Tanabe, S., Maruyama, Y., Mangmool, S., Urayama, K., Nagamatsu, Y, Takagahara, S., Turner, J. H., Kozasa, T., Kobayashi, H., et al. 2005. G alpha 12/13- and reactive oxygen species-dependent activation of c-Jun NH2-terminal kinase and p38 mitogen-activated protein kinase by angiotensin receptor stimulation in rat neonatal cardiomyocytes. *J Biol Chem.* 280:18434-18441.
37. Li, Q., Harraz, M. M., Zhou, W., Zhang, L. N., Ding, W., Zhang, Y., Eggleston, T., Yeaman, C., Banfi, B., and Engelhardt, J. F. 2006. Nox2 and Rac1 regulate H2O2-dependent recruitment of TRAF6 to endosomal interleukin-1 receptor complexes. *Mol Cell Biol.* 26:140-154.
38. Sarkar, S., Vellaichamy, E., Young, D., and Sen, S. 2004. Influence of cytokines and growth factors in ANG II-mediated collagen upregulation by fibroblasts in rats: role of myocytes. *Am J Physiol Heart Circ Physiol.* 287:H107-117.
39. Saccani, S., Polentarutti, N., Penton-Rol, G., Sims, J. E., and Mantovani, A. 1998. Divergent effects of LPS on expression of IL-1 receptor family members in mononuclear phagocytes in vitro and in vivo. *Cytokine* 10:773-780.
40. May, L. T., Ndubuisi, M. I., Patel, K., and Garcia, D. 1995. Interleukin-6 chaperones in blood. *Ann NY Acad Sci.* 762:120-128.
41. Economides, A X, Carpenter, L. R., Rudge, J. S., Wong, V., Koehler-Stec, E. M., Hartnett, C., Pyles, E. A., Xu, X., Daly, T. J., Young, M. R., et al. 2003. Cytokine traps: multi-component, high-affinity blockers of cytokine action. *Nat Med.* 9:47-52.
42. Hsieh, P. C., Davis, M. E., Gannon, J., MacGillivray, C., and Lee, R. T. 2006. Controlled delivery of PDGF-BB for myocardial protection using injectable self-assembling peptide nanofibers. *J Clin Invest.* 116:237-248.
43. Yokoyama, T., Sekiguchi, K., Tanaka, T., Tomaru, K., Arai, M., Suzuki, T., and Nagai, R. 1999. Angiotensin II and mechanical stretch induce production of tumor necrosis factor in cardiac fibroblasts. *Am J Physiol* 276:H1968-1976.
44. Yamamoto, K., Dang, Q. N., Kennedy, S. P., Osathanondh, R., Kelly, R. A., and Lee, R. T. 1999. Induction of tenascin-C in cardiac myocytes by mechanical deformation. Role of reactive oxygen species. *J Biol Chem.* 274:21840-21846.
45. Hakuno, D., Takahashi, T., Lammerding, J., and Lee, R. T. 2005. Focal adhesion kinase signaling regulates cardiogenesis of embryonic stem cells. *J Biol Chem.* 280:39534-39544.
46. Yamamoto, K., Ohki, R., Lee, R. T., Ikeda, U., and Shimada, K. 2001. Peroxisome proliferator-activated receptor gamma activators inhibit cardiac hypertrophy in cardiac myocytes. *Circulation* 104:1670-1675.
47. Frantz, S., Kobzik, L., Kim, Y. D., Fukazawa, R., Medzhitov, R., Lee, R. T., and Kelly, R. A. 1999. Toll4 (TLR4) expression in cardiac myocytes in normal and failing myocardium. *J Clin Invest.* 104:271-280.
48. Schulze, P. C., Yoshioka, J., Takahashi, T., He, Z., King, G. L., and Lee, R. T. 2004. Hyperglycemia promotes oxidative stress through inhibition of thioredoxin function by thioredoxin-interacting protein. *J Biol Chem.* 279:30369-30374.
49. Rockman, H. A., Ross, R. S., Harris, A. N., Knowlton, K. U., Steinhelper, M. E., Field, L. J., Ross, J. J., and Chien, K. R. 1991. Segregation of atrial-specific and inducible expression of an atrial natriuretic factor transgene in an in vivo murine model of cardiac hypertrophy. *Proc Natl Acad Sci USA* 88:8277-8281.
50. Tanaka, N., Dalton, N., Mao, L., Rockman, H. A., Peterson, K. L., Gottshall, K. R., Hunter, J. J., Chien, K. R., and Ross, J. J. 1996. Transthoracic echocardiography in models of cardiac disease in the mouse. *Circulation* 94:1109-1117.
51. Collins, K. A., Korcarz, C. E., Shroff, S. G., Bednarz, J. E., Fentzke, R. C., Lin, H., Leiden, J. M., and Lang, R. M. 2001. Accuracy of echocardiographic estimates of left ventricular mass in mice. *Am J Physiol Heart Circ Physiol* 280:H1954-1962.
52. Takemoto, M., Egashira, K., Usui, M., Numaguchi, K., Tomita, H., Tsutsui, H., Shimokawa, H., Sueishi, K., and Takeshita, A. 1997. Important role of tissue angiotensin-converting enzyme activity in the pathogenesis of coronary vascular and myocardial structural changes induced by long-term blockade of nitric oxide synthesis in rats. *J Clin Invest* 99:278-287.

Example 3

86 mice with wild-type (WT) or ST2 knockout (ST2KO) genotypes were randomized into 4 subgroups, Sham or MI operated, and with or without IL-33 treatment. Experimental myocardial infraction operation was done by permanent occlusion of the left anterior coronary artery via open-chest approach under deep anesthesia. IL-33 treatment was done by a single 2 microgram/kg on each day, intraperitoneal, of recombinant rat IL-33 protein, from the day of operation up to 4 weeks.

Figure 18:
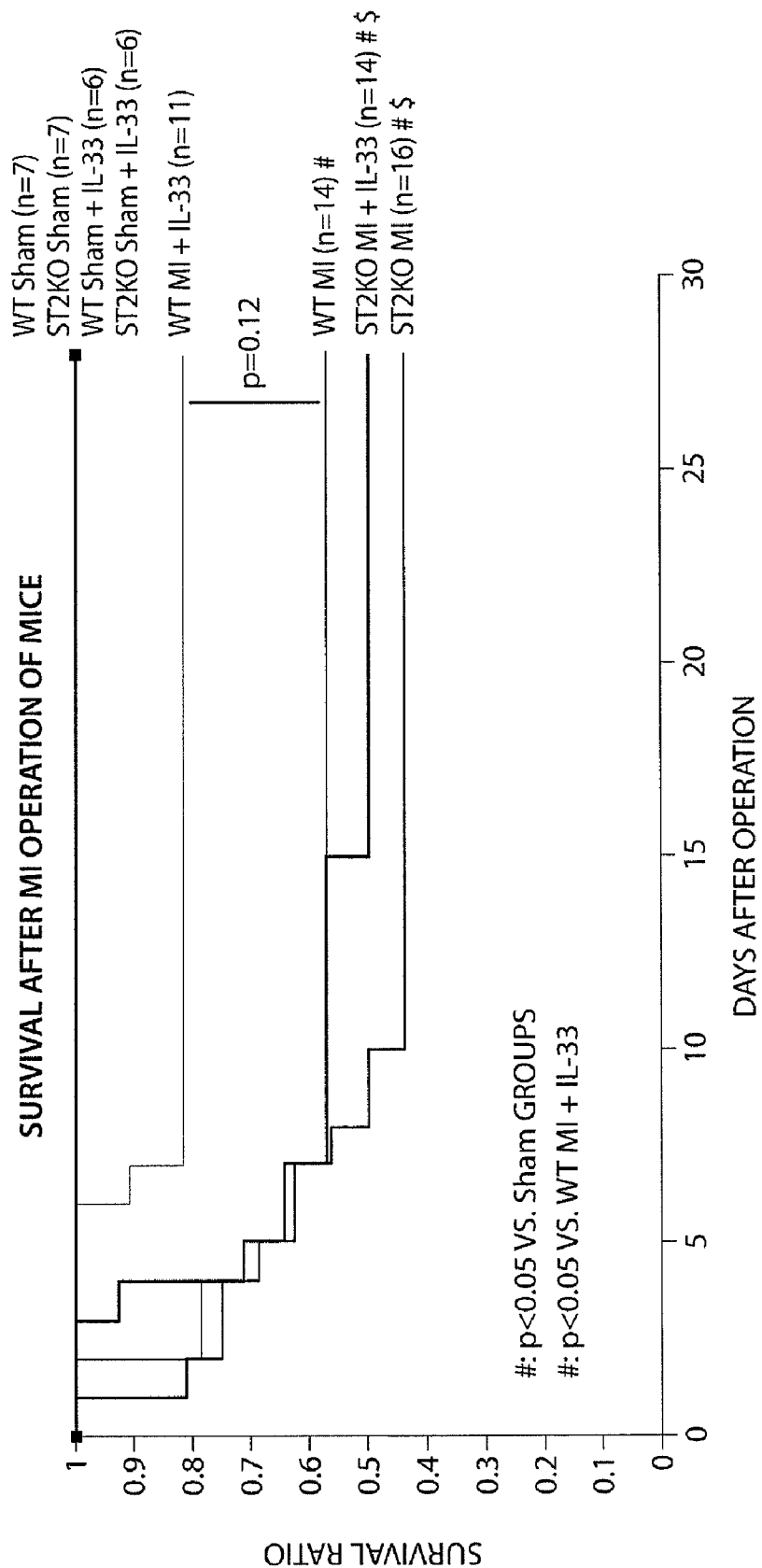
FIG. 18 provides the survival ratio of mice after experimental MI. This indicates that IL-33 improves survival after infarction and that deletion of the receptor for IL-33 (ST2) eliminates this benefit.

The results show that IL-33 improves survival after infarction and that deletion of the receptor for IL-33 (ST2) eliminates this benefit (FIG. 18).

Example 4

Materials and Methods

Cell Culture

Hearts from 1-3 day-old Sprague-Dawley rat neonates (Charles River) were digested and plated on non-coated culture dishes for 1.5 hrs. Attached cells were further cultured with Dulbecco's Modified Essential Medium (GIBCO) containing 10% fetal bovine serum (GIBCO) and used as cardiac fibroblasts after 2 passages. Non-attached cells were re-plated on 0.1% gelatin-precoated dishes and further cultured with 7% fetal bovine serum as cardiomyocytes. Cells were serum-starved for 24 hrs prior to experiments.

Cardiomyocyte Apoptosis Assays

Figure 19:
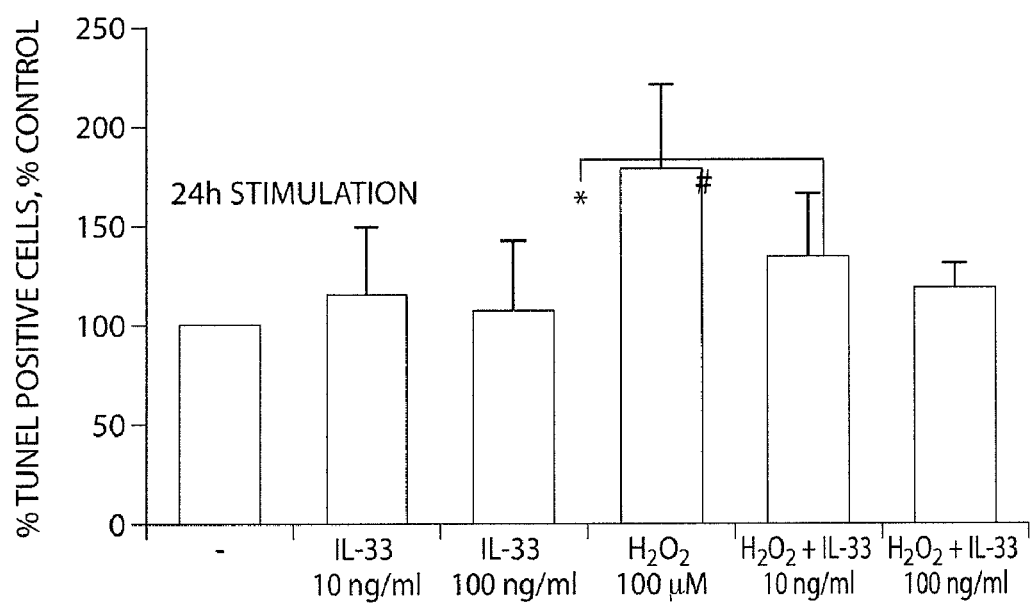
FIG. 19 shows results from TUNEL staining on rat neonatal cardiomyocytes. This assay for apoptosis suggests that IL-33 can prevent apoptosis in cardiac myocytes. The apoptotic stimulus was $H_2O_2$, a standard method of inducing cardiomyocyte apoptosis.

For cardiomyocyte apoptosis assays, cardiomyocytes were plated overnight, cultured serum-free for 24 hours, and then subjected to 0.1 mM $H_2O_2$ for another 24 hours with or without treatment with purified rat mature IL-33 protein. TUNEL staining (FIG. 19) was performed using a TUNEL staining kit (Roche Diagnostics Corp., Indianapolis, Ind.). For DNA fragmentation experiments (FIGS. 19 and 20), cells were trypsinized, fixed with ethanol, incubated in RNase, stained with propidium iodide, and then subjected to flow cytometry (Cytomics FC 500; Beckman Coulter).

Western Blot Analysis

Figure 20A:
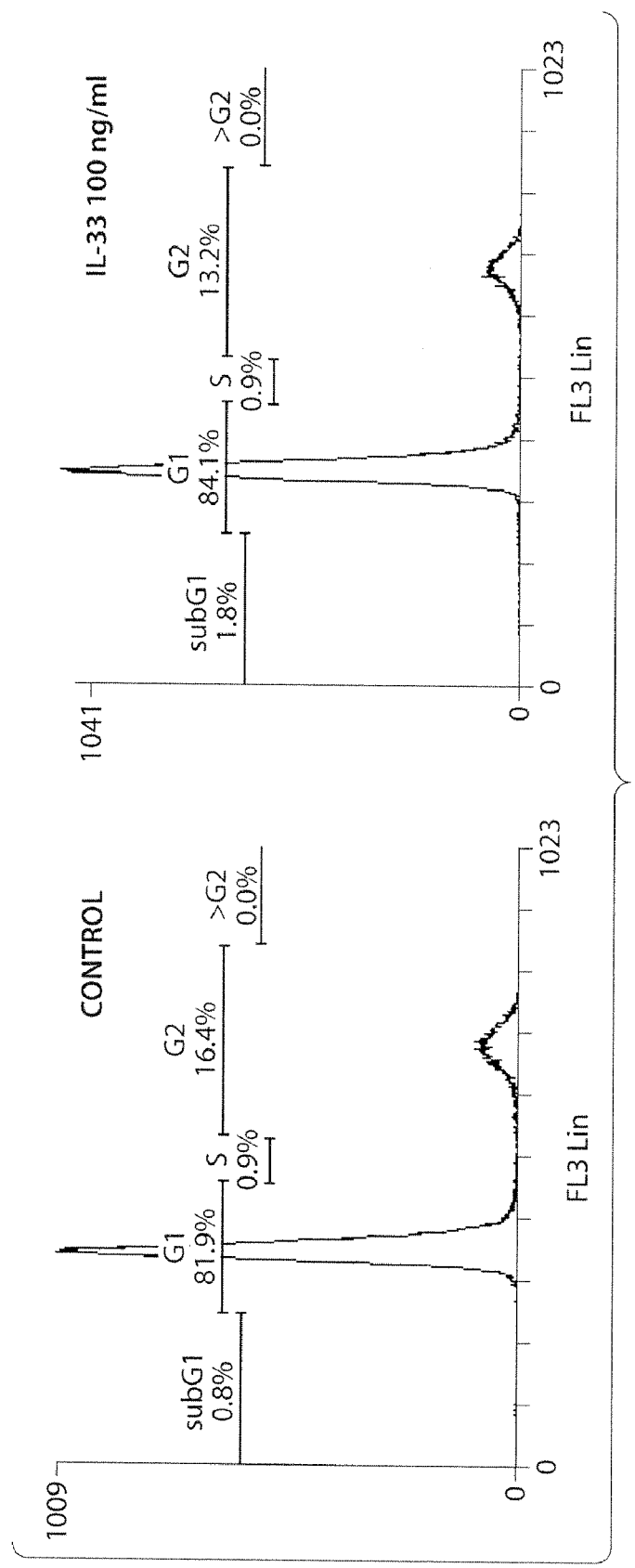
FIGS. 20A, 20B and 20C show results from flow cytometry after propidium iodide staining of rat neonatal cardiomyocytes. This assay for appoptosis confirmed that IL-33 can prevent apoptosis in cardiac myocytes. The apoptotic stimulus was $H_2O_2$.
Figure 20B:
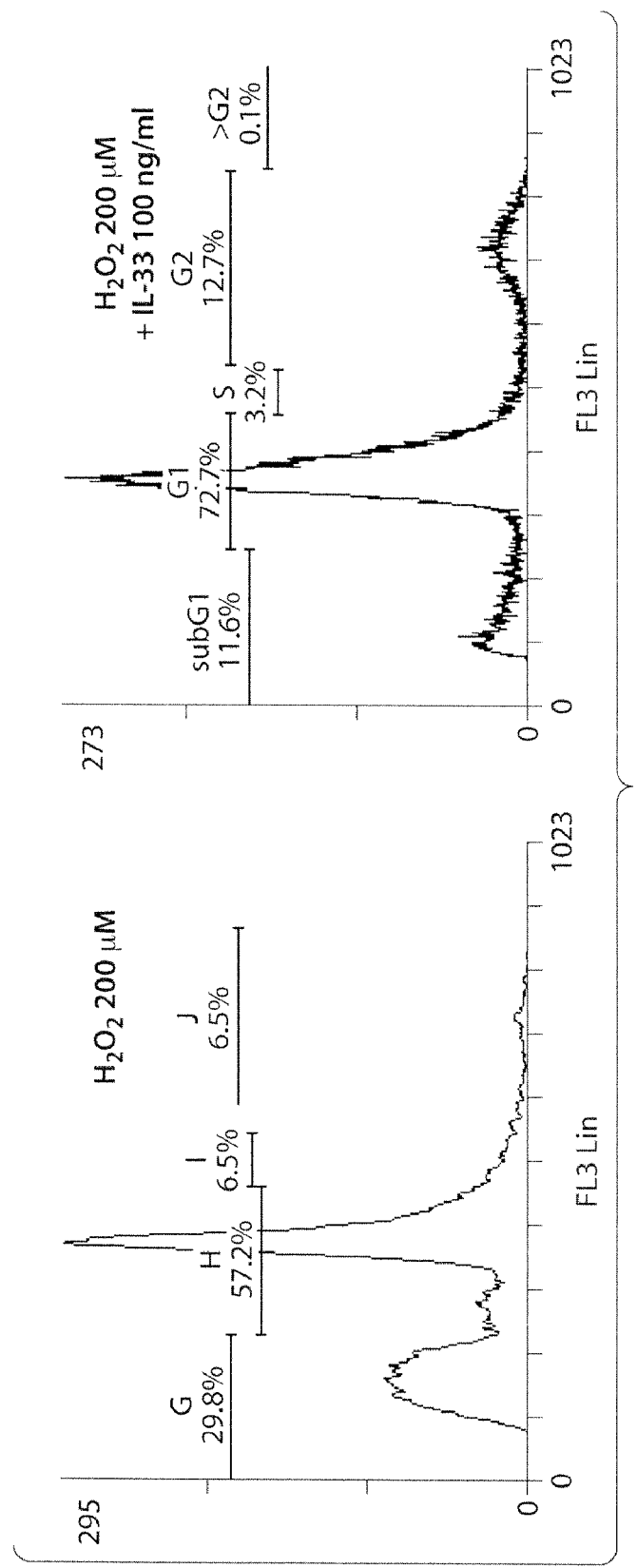
Figure 20C:
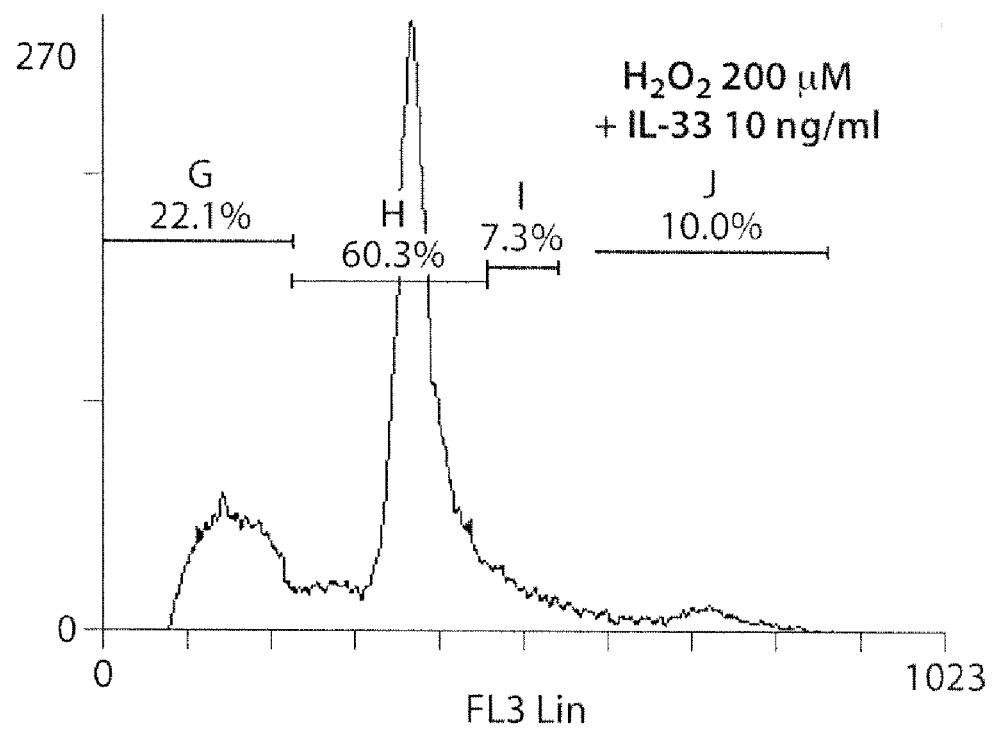

Membranes (PVDF, PerkinElmer) were incubated with primary antibodies overnight (anti-cleaved caspase-3, 1:1000; from Cell Signaling Technology) at 4° C., detected with horseradish peroxidase-conjugated antibodies (Bio-Rad) and enhanced chemiluminescence (FIG. 20).

Myocardial Infarction and Treatment with IL-33 Protein

Figure 21:
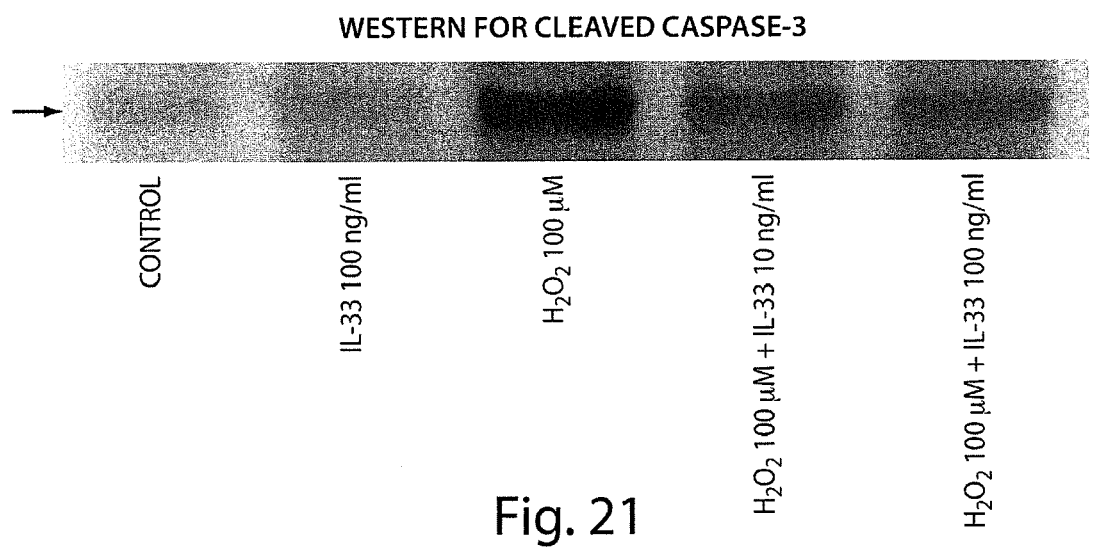
FIG. 21 shows results from an evaluation of caspase-3 activation of rat neonatal cardiomyocytes. This assay is a highly specific assay for an important molecular event of apoptosis and also shows that IL-33 can prevent apoptosis in cardiac myocytes. The apoptotic stimulus was $H_2O_2$.

Targeted ST2−/− mice and their WT littermates were employed for the experiments. MI was produced on 8-10 week old mice. A single operator with over 20 years rodent cardiac surgery experience who was blinded to genotype and the randomized treatment assignment performed all operative procedures. Following the procedure, each mouse received daily i.p. injection of recombinant rat IL-33 (2 μg) or vehicle from the day after MI operation for 4 weeks (FIG. 21).

Results

In order to determine the effects on apoptosis, multiple methods were employed (TUNEL staining, flow cytometry and caspase-3 evaluation). The apoptotic stimulus was $H_2O_2$. The results from the various apoptosis experiments show that IL-33 can prevent apoptosis in cardiac myocytes.

The listing of the references herein is not intended to be an admission that any of the references is a prior art reference.

Each of the foregoing patents, patent applications and references that are recited in this application are herein incorporated in their entirety by reference. Having described the presently, preferred embodiments, and in accordance with the present invention, it is believed that other modifications, variations and changes will be suggested to those skilled in the art in view of the teachings set forth herein. It is, therefore, to be understood that all such variations, modifications and changes are believed to fall within the scope of the present invention as defined by the appended claims.

I/We claim:

1. A method for treating a subject that has cardiac fibrosis or cardiomyocyte hypertrophy comprising:
   administering an effective amount of IL-33 to a subject in need of such a treatment to treat the subject.

2. The method of claim 1, wherein the subject is otherwise free of indications other than a cardiac disease or disorder.

3. The method of claim 1 or 2, wherein the subject has or has had a myocardial infarction, a stroke, arteriosclerosis or heart failure.

4. The method of claim 1 or 2, wherein the IL-33 is administered orally, sublingually, intravenously, intramuscularly or subcutaneously.

5. The method of claim 1 or 2, further comprising administering a second agent to the subject.

6. The method of claim 5, wherein the second agent is a soluble ST2 inhibiting agent, an anti-lipemic agent, an anti-inflammatory agent, an anti-thrombotic agent, a fibrinolytic agent, an anti-platelet agent, a direct thrombin inhibitor, a glycoprotein IIb/IIIa receptor inhibitor, an alpha-adrenergic blocker, a beta-adrenergic blocker, a cyclooxygenase-2 inhibitor, an angiotensin system inhibitor, an anti-arrhythmic, a calcium channel blocker, a diuretic, an inotropic agent, a vasodilator, a vasopressor, a thiazolidinedione or a cannabinoid-1 receptor blocker.

7. The method of claim 1 or 2, wherein the subject is otherwise free of indications other than the cardiac fibrosis or cardiomyocyte hypertrophy.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 1
tcgcacctgt gactgaaatc                                              20

<210> SEQ ID NO 2
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 2
acacagcatg ccacaaacat                                              20

<210> SEQ ID NO 3
<211> LENGTH: 20
<212> TYPE: DNA
<213> ORGANISM: Artificial sequence
<220> FEATURE:
<223> OTHER INFORMATION: synthetic oligonucleotide
```

-continued

```
<400> SEQUENCE: 3
atacagtgcg gtgtccaaca                                              20

<210> SEQ ID NO 4
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 4
cgagagcacc tccatctctc                                              20

<210> SEQ ID NO 5
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 5
ggaaatggct cagagacagc                                              20

<210> SEQ ID NO 6
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 6
cgatccggtc tatcttctgc                                              20

<210> SEQ ID NO 7
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 7
ttgaccctaa ccaaggatgc                                              20

<210> SEQ ID NO 8
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 8
caccccttct gcgttgtatt                                              20

<210> SEQ ID NO 9
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 9
gacagatgct ggtgctgaga                                              20

<210> SEQ ID NO 10
<211> LENGTH: 20
<212> TYPE: DNA
```

<213> ORGANISM: Artificial sequence
<220> FEATURE:
<223> OTHER INFORMATION: synthetic oligonucleotide

<400> SEQUENCE: 10
gcctgatcca tgtaggcaat                                        20

<210> SEQ ID NO 11
<211> LENGTH: 24
<212> TYPE: DNA
<213> ORGANISM: Artificial sequence
<220> FEATURE:
<223> OTHER INFORMATION: synthetic oligonucleotide

<400> SEQUENCE: 11
agtatccaag gaacttcact gcta                                   24

<210> SEQ ID NO 12
<211> LENGTH: 27
<212> TYPE: DNA
<213> ORGANISM: Artificial sequence
<220> FEATURE:
<223> OTHER INFORMATION: synthetic oligonucleotide

<400> SEQUENCE: 12
ttacatctta gagagcttaa acatgat                                27

<210> SEQ ID NO 13
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 13
ttacccagcc aggatgtttc                                        20

<210> SEQ ID NO 14
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 14 ctagggggctt ggcttctctt                                       20

<210> SEQ ID NO 15
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 15
agttgagggg actttcccag gc                                     22

<210> SEQ ID NO 16
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 16
cagctcttga aggaccaagg                                        20

```
<210> SEQ ID NO 17
<211> LENGTH: 20
<212> TYPE: DNA
<213> ORGANISM: Artificial sequence
<220> FEATURE:
<223> OTHER INFORMATION: synthetic oligonucleotide

<400> SEQUENCE: 17
agacccaggc agagtcagaa                                            20

<210> SEQ ID NO 18
<211> LENGTH: 22
<212> TYPE: DNA
<213> ORGANISM: Artificial sequence
<220> FEATURE:
<223> OTHER INFORMATION: synthetic oligonucleotide

<400> SEQUENCE: 18
gcctgggaaa gtcccctcaa ct                                         22
```